(12) United States Patent
Jounaidi et al.

(10) Patent No.: US 12,202,856 B2
(45) Date of Patent: Jan. 21, 2025

(54) TETHERED INTERLEUKIN-2 TO ITS RECEPTOR IL-2RBETA, A PLATFORM TO ENHANCE NATURAL KILLER AND REGULATORY T CELL ACTIVITY

(71) Applicant: The General Hospital Corporation, Boston, MA (US)

(72) Inventors: Youssef Jounaidi, Boston, MA (US); Stuart Forman, Arlington, MA (US); Keith Miller, Lincoln, MA (US); Joseph F. Cotten, Northborough, MA (US)

(73) Assignee: The General Hospital Corporation, Boston, MA (US)

(*) Notice: Subject to any disclaimer, the term of this patent is extended or adjusted under 35 U.S.C. 154(b) by 54 days.

(21) Appl. No.: 16/302,001

(22) PCT Filed: May 19, 2017

(86) PCT No.: PCT/US2017/033585
§ 371 (c)(1),
(2) Date: Nov. 15, 2018

(87) PCT Pub. No.: WO2017/201432
PCT Pub. Date: Nov. 23, 2017

(65) Prior Publication Data
US 2020/0316118 A1    Oct. 8, 2020

Related U.S. Application Data

(60) Provisional application No. 62/471,456, filed on Mar. 15, 2017, provisional application No. 62/338,757, filed on May 19, 2016.

(51) Int. Cl.
| | |
|---|---|
| C07K 16/46 | (2006.01) |
| A61K 39/00 | (2006.01) |
| C07K 14/55 | (2006.01) |
| C07K 14/705 | (2006.01) |
| C07K 14/715 | (2006.01) |
| C07K 19/00 | (2006.01) |
| C12N 5/00 | (2006.01) |
| C12N 5/0783 | (2010.01) |
| C12N 15/00 | (2006.01) |
| A61K 9/00 | (2006.01) |
| A61K 38/00 | (2006.01) |
| A61K 45/06 | (2006.01) |

(52) U.S. Cl.
CPC .......... *C07K 14/55* (2013.01); *A61K 39/4613* (2023.05); *A61K 39/464406* (2023.05); *A61K 39/464493* (2023.05); *C07K 14/70521* (2013.01); *C07K 14/7155* (2013.01); *C12N 5/0646* (2013.01); *A61K 9/0019* (2013.01); *A61K 38/00* (2013.01); *A61K 45/06* (2013.01); *A61K 2239/31* (2023.05); *A61K 2239/38* (2023.05); *A61K 2239/47* (2023.05); *A61K 2239/58* (2023.05); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,747,292 | A | 5/1998 | Greenberg et al. |
| 5,811,097 | A | 9/1998 | Allison et al. |
| 5,855,887 | A | 1/1999 | Allison et al. |
| 6,051,227 | A | 4/2000 | Allison et al. |
| 6,682,736 | B1 | 1/2004 | Hanson et al. |
| 6,984,720 | B1 | 1/2006 | Korman et al. |
| 7,605,238 | B2 | 10/2009 | Korman et al. |
| 7,618,817 | B2 | 11/2009 | Campbell |
| 7,741,345 | B2 | 6/2010 | Cannizzaro et al. |
| 8,008,449 | B2 | 8/2011 | Korman et al. |
| 8,034,332 | B2 | 10/2011 | Klingemann |
| 8,313,943 | B2 | 11/2012 | Campbell |
| 8,552,156 | B2 | 10/2013 | Takayanagi et al. |
| 8,591,900 | B2 | 11/2013 | Barrett et al. |
| 9,073,994 | B2 | 7/2015 | Honjo et al. |
| 2002/0068044 | A1 | 6/2002 | Klingemann |
| 2003/0165499 | A1 | 1/2003 | McCall et al. |

(Continued)

FOREIGN PATENT DOCUMENTS

| | | |
|---|---|---|
| CN | 1626554 | 6/2005 |
| CN | 101319247 | 12/2008 |

(Continued)

OTHER PUBLICATIONS

Jiang et al. Transfection of chimeric anti-CD138 gene enhances natural killer cell activation and killing of multiple myeloma cells. Molecular Oncology vol. 8:297-310; 2014 (available online Dec. 12, 2013). (Year: 2014).*

(Continued)

*Primary Examiner* — Elizabeth C. Kemmerer
*Assistant Examiner* — Regina M DeBerry
(74) *Attorney, Agent, or Firm* — Fish & Richardson P.C.

(57) ABSTRACT

Fusion proteins comprising IL2 and IL2Rβ (e.g., CIRB), IL2, IL2Rβ and IL21R (e.g., CIRB21), and/or comprising IL2, IL2Rβ, and CD28 (e.g., CIRB28); natural killer (NK) cells that express the fusion proteins and methods of use thereof, e.g., to treat subjects with cancer; and regulatory T cells (T-regs) that express a fusion protein comprising IL2, IL2Rβ, and CD28 and methods of use thereof, e.g., to treat subjects with autoimmune disease or GVHD.

7 Claims, 22 Drawing Sheets
Specification includes a Sequence Listing.

(56) References Cited

U.S. PATENT DOCUMENTS

| | | | |
|---|---|---|---|
| 2004/0120948 | A1 | 6/2004 | Mikayama et al. |
| 2005/0095223 | A1 | 5/2005 | Sivakumar et al. |
| 2005/0273869 | A1 | 12/2005 | Court et al. |
| 2007/0148163 | A1 | 6/2007 | Takahashi et al. |
| 2009/0025274 | A1 | 1/2009 | Lail |
| 2011/0009291 | A1 | 1/2011 | Chen et al. |
| 2011/0271358 | A1 | 11/2011 | Freeman et al. |
| 2013/0011405 | A1 | 1/2013 | Long et al. |
| 2013/0022623 | A1 | 1/2013 | Karsunky et al. |
| 2015/0086574 | A1 | 3/2015 | Karsunky et al. |
| 2015/0368360 | A1 | 12/2015 | Liang et al. |
| 2016/0257749 | A1 | 9/2016 | Lifke et al. |
| 2016/0257758 | A1 | 9/2016 | Gray et al. |
| 2016/0303124 | A1 | 10/2016 | Webster et al. |
| 2017/0022273 | A1 | 1/2017 | Zhou et al. |
| 2017/0058033 | A1 | 3/2017 | Ludwig et al. |
| 2017/0101472 | A1 | 4/2017 | Ullman et al. |
| 2017/0114135 | A1 | 4/2017 | Codarri-Deak et al. |
| 2017/0233448 | A1* | 8/2017 | Malek .............. C07K 14/55 424/85.2 |
| 2017/0290914 | A1 | 10/2017 | Liang et al. |
| 2017/0313783 | A1 | 11/2017 | Karsunky et al. |
| 2017/0334995 | A1 | 11/2017 | Zettl et al. |
| 2018/0016336 | A1 | 1/2018 | Schebye et al. |
| 2018/0072804 | A1 | 3/2018 | Lifke et al. |
| 2018/0230431 | A1 | 8/2018 | Bi et al. |
| 2018/0251549 | A1 | 9/2018 | Gray et al. |
| 2018/0251767 | A1 | 9/2018 | Schroff et al. |
| 2018/0298097 | A1 | 10/2018 | Schebye et al. |
| 2018/0326054 | A1 | 11/2018 | Codarri Deak et al. |
| 2019/0127435 | A1* | 5/2019 | Schmitt .............. C07K 16/30 |
| 2019/0359685 | A1* | 11/2019 | Tanaka .............. A61P 35/00 |
| 2020/0040082 | A1 | 2/2020 | Piasecki et al. |
| 2020/0062859 | A1 | 2/2020 | Piasecki et al. |

FOREIGN PATENT DOCUMENTS

| | | |
|---|---|---|
| EP | 1212422 | 6/2002 |
| WO | WO 1998/049268 | 11/1998 |
| WO | WO 1999/045128 | 9/1999 |
| WO | WO 2002/088186 | 11/2002 |
| WO | WO 2002/088346 | 11/2002 |
| WO | WO 2006/023148 | 3/2006 |
| WO | WO 2007/124299 | 11/2007 |
| WO | WO 2010/020766 | 2/2010 |
| WO | WO 2011/123489 | 10/2011 |
| WO | WO 2011/123683 | 10/2011 |
| WO | WO 2012/111762 | 8/2012 |
| WO | WO 2012/149356 | 11/2012 |
| WO | WO 2013/079174 | 6/2013 |
| WO | WO 2013/177187 | 1/2014 |
| WO | WO 2014/070934 | 5/2014 |
| WO | WO 2014/195852 | 12/2014 |
| WO | WO 2015/193411 | 12/2015 |
| WO | WO 2016/007235 | 1/2016 |
| WO | WO 2016/022671 | 2/2016 |
| WO | WO 2016/061142 | 4/2016 |
| WO | WO 2016/071448 | 5/2016 |
| WO | WO 2016/160602 | 10/2016 |
| WO | WO 2019/051424 | 3/2019 |
| WO | WO 2022/232796 | 11/2022 |

OTHER PUBLICATIONS

Hashmi et al. Interleukin-21: updated review of Phase I and II clinical trials in metastatic renal cell carcinoma, metastatic melanoma and relapsed/refractory indolent non-Hodgkin's lymphoma. Expert Opinion on Biological Therapy vol. 10/5:807-817 (published online Apr. 12, 2010). (Year: 2010).*

Hassanpou et al. Review of cancer from perspective of molecular. Journal of Cancer Research and Practice. vol. 4:127-129; (available Jul. 2017). (Year: 2017).*

Tai et a. PC3 is a cell line characteristic of prostatic small cell carcinoma. Prostate. vol. 71(15): 1668-1679 (Nov. 2011). (Year: 2011).*

Haddad et al. Mouse models of glioblastoma for the evaluation of novel therapeutic strategies. Neuro-Oncology Advances 3(1), 1-16, (2021). (Year: 2021).*

Justice et al. Using the mouse to model human disease: increasing validity and reproducibility, Disease, Models & Mechanisms 9: 101-103, (2016). (Year: 2016).*

Algarra et al., "The HLA crossroad in tumor immunology," Hum. Immunol., Jan. 2000, 61(1):65-73.

Arai et al., "Infusion of the allogeneic cell line NK-92 in patients with advanced renal cell cancer or melanoma: a phase I trial," Cytotherapy, 2008, 10(6):625-632.

Ardizzoni et al., "Biologic and clinical effects of continuous infusion interleukin-2 in patients with non-small cell lung cancer," Cancer, Mar. 1994, 73(5):1353-1360.

Asao et al., "Cutting edge: the common gamma-chain is an indispensable subunit of the IL-21 receptor complex," J. Immunol., Jul. 2001, 167(1):1-5.

Barnes, "Anti-inflammatory actions of glucocorticoids: molecular mechanisms," Clin. Sci., (Lond), Jun. 1998, 94(6):557-572.

Bell et al., "Sustained in vivo signaling by long-lived IL-2 induces prolonged increases of regulatory T cells," J. Autoimmun., Jan. 2015, 56:66-80.

Beres et al., "CD8+ Foxp3+ regulatory T cells are induced during graft-versus-host disease and mitigate disease severity," J. Immunol. Jul. 2012, 189(1):464-474.

Bernsen et al., "On the biological relevance of MHC class II and B7 expression by tumour cells in melanoma metastases," Br. J. Cancer, Feb. 2003, 88(3):424-431.

Bluestone & Abbas., "Natural versus adaptive regulatory T cells," Nat. Rev. Immunol., Mar. 2003, 3(3):253-257.

Boumpas et al., "Dexamethasone inhibits human interleukin 2 but not interleukin 2 receptor gene expression in vitro at the level of nuclear transcription," J. Clin. Invest., May 1991, 87(5):1739-1747.

Bromberg et al., "Stat3 as an oncogene," Cell, Aug. 1999, 98(3):295-303.

Bromberg, "Stat proteins and oncogenesis," J. Clin. Invest., May 2002, 109(9):1139-1142.

Brunstein et al., "Infusion of ex vivo expanded T regulatory cells in adults transplanted with umbilical cord blood: safety profile and detection kinetics," Blood, Jan. 2011, 117(3):1061-1070.

Caligiuri et al., "Functional consequences of interleukin 2 receptor expression on resting human lymphocytes. Identification of a novel natural killer cell subset with high affinity receptors," J. Exp. Med., May 1990, 171(5):1509-1526.

Caligiuri, "Human natural killer cells," Blood, Aug. 2008, 112(3):461-469.

Chakraborty et al., "Robust and cost effective expansion of human regulatory T cells highly functional in a xenograft model of graft-versus-host disease," Haematologica, Apr. 2013, 98(4):533-537.

Chen et al., "IL-2 controls the stability of Foxp3 expression in TGF-β-induced Foxp3+ T cells in vivo," J. Immunol., Jun. 2011, 186(11):6329-6337.

Chin et al., "Cell growth arrest and induction of cyclin-dependent kinase inhibitor p21 WAF1/CIP1 mediated by STAT1," Science, Apr. 1996, 272(5262):719-722.

Clayton et al., "Human tumor-derived exosomes down-modulate NKG2D expression," J. Immunol., Jun. 2008, 180(11):7249-7258.

Clayton et al., "Human tumor-derived exosomes selectively impair lymphocyte responses to interleukin-2," Cancer. Res., Aug. 2007, 67(15):7458-7466.

Cohney et al., "SOCS-3 is tyrosine phosphorylated in response to interleukin-2 and suppresses STAT5 phosphorylation and lymphocyte proliferation," Mol. Cell. Biol., Jul. 1999, 19(7):4980-4988.

Dahlberg et al., "Natural Killer Cell-Based Therapies Targeting Cancer: Possible Strategies to Gain and Sustain Anti-Tumor Activity," Frontiers in Immunology, Nov. 2015, 6(605), 19 pages.

Dieckmann et al., "Ex vivo isolation and characterization of CD4+ CD25+ T cells with regulatory properties from human blood," Journal of Experimental Medicine, Jun. 2001, 193(11):1303-1310.

(56) References Cited

OTHER PUBLICATIONS

Donatelli et al., "TGF-beta-inducible microRNA-183 silences tumor-associated natural killer cells," Proc. Natl. Acad. Sci., Mar. 2014, 111(11):4203-4208.
Donohue & Rosenberg., "The fate of interleukin-2 after in vivo administration," J. Immunol., May 1983, 130(5):2203-2208.
Endo et al., "A new protein containing an SH2 domain that inhibits JAK kinases," Nature, Jun. 1997, 387(6636):921-924.
EP Extended European Search Report in European Appln. No. 17800257.2, dated Dec. 17, 2019, 11 pages.
Esensten et al., "CD28 Costimulation: From Mechanism to Therapy," Immunity, Cell Press, May 2016, 44(5):973-988.
Feng et al., "Interleukin-12 converts Foxp3+ regulatory T cells to interferon-γ-producing Foxp3+ T cells that inhibit colitis," Gastroenterology, Jun. 2011, 140(7):2031-2043.
Fujii et al., "Activation of Stat5 by interleukin 2 requires a carboxyl-terminal region of the interleukin 2 receptor beta chain but is not essential for the proliferative signal transmission," Proc. Natl. Acad. Sci., Jun. 1995, 92(12):5482-5486.
Gasteiger et al., "Foxp3+ Regulatory T-cells and IL-2: The Moirai of T-cell Fates?" Front Immunol, 2012, 3:179, 4 pages.
Geller et al., "A phase II study of allogeneic natural killer cell therapy to treat patients with recurrent ovarian and breast cancer," Cytotherapy, Jan. 2011, 13(1):98-107.
Ghiringhelli et al., "CD4+CD25+ regulatory T cells inhibit natural killer cell functions in a transforming growth factor-beta-dependent manner," J. Exp. Med., Oct. 2005, 202(8):1075-1085.
Glauser et al., "Review: Cardiopulmonary toxicity of adoptive immunotherapy," Am. J. Med. Sci., Dec. 1988, 296(6):406-412.
Glienke et al., "Advantages and applications of CAR-expressing natural killer cells," Front Pharmacol., Feb. 2015, 6:21.
Gong et al., "Characterization of a human cell line (NK-92) with phenotypical and functional characteristics of activated natural killer cells," Leukemia, Apr. 1994, 8(4):652-658.
Hall et al., "Specific unresponsiveness in rats with prolonged cardiac allograft survival after treatment with cyclosporine. III. Further characterization of the CD4+ suppressor cell and its mechanisms of action," J. Exp. Med., Jan. 1990, 171(1):141-157.
Hallett et al., "Positive and negative regulation of Natural Killer cells: Therapeutic implications," Seminars in Cancer Biology, Oct. 2006, 16(5):367-382.
Hatakeyama et al., "Interleukin-2 receptor beta chain gene: generation of three receptor forms by cloned human alpha and beta chain cDNA's," Science 1989, 244(4904):551-556.
Hersey et al., "Expression of the co-stimulatory molecule B7 on melanoma cells," Int. J. Cancer, Aug. 1994, 58(4):527-532.
Hippen et al., "Massive ex vivo expansion of human natural regulatory T cells (Tregs) with minimal loss of in vivo functional activity," Sci. Transl. Med., May 2011, 3(83), 16 pages.
Hsu et al., "The immunostimulatory effect of lenalidomide on NK-cell function is profoundly inhibited by concurrent dexamethasone therapy," Blood, Feb. 2011, 117(5):1605-1613.
Kaighn et al., "Establishment and characterization of a human prostatic carcinoma cell line (PC-3)," Invest. Urol., Jun. 1979, 17(1):16-23.
Kaplan et al., "Demonstration of an interferon gamma-dependent tumor surveillance system in immunocompetent mice," Proc. Natl. Acad. Sci., Jun. 1998, 95(13):7556-7561.
Ke et al., "VEGF(121), VEGF(165) overexpression enhances tumorigenicity in U251 MG but not in NG-1 glioma cells," Cancer. Res., Mar. 2002, 62(6):1854-1861.
Klingemann et al., "Natural Killer Cells for Immunotherapy—Advantages of the NK-92 Cell Line over Blood NK Cells," Frontiers in Immunology, Mar. 2016, 7(91), 7 pages.
Kochan et al., "Role of non-classical MHC class I molecules in cancer immunosuppression," Oncoimmunology, Nov. 2013, 2(11):e26491.
Konstantinidis et al., "Targeting IL-2 to the endoplasmic reticulum confines autocrine growth stimulation to NK-92 cells," Exp. Hematol., Feb. 2005, 33(2):159-164.

Leonard et al., "Molecular cloning and expression of cDNAs for the human interleukin-2 receptor," Nature, Oct. 1984, 311(5987):626-631.
Levin et al., "Exploiting a natural conformational switch to engineer an interleukin-2 'superkine'," Nature, Apr. 2012, 484(7395):529-533.
Levy et al., "Natural Killer Cells in Human Cancer: From Biological Functions to Clinical Applications," Journal of Biomedicine and Biotechnology, 2011, 11 pages.
Li et al., "Cancer-expanded myeloid-derived suppressor cells induce anergy of NK cells through membrane-bound TGF-beta 1," J. Immunol., Jan. 2009, 182(1):240-249.
Lin et al., "HLA-G expression in human ovarian carcinoma counteracts NK cell function," Ann. Oncol., Sep. 2007, 18(11):1804-1809.
Luznik and Fuchs, "High-dose, post-transplantation cyclophosphamide to promote graft-host tolerance after allogeneic hematopoietic stem cell transplantation," Immunol. Res., Jul. 2010, 47(1-3):65-77.
Löhr et al., "Transforming growth factor-beta1 induces desmoplasia in an experimental model of human pancreatic carcinoma, " Cancer. Res., Jan. 2001, 61(2):550-555.
Maas et al., "Interleukin-2 in cancer treatment: disappointing or (still) promising? A review," Cancer Immunol. Immunother., May 1993, 36(3):141-148.
Malek, "The biology of interleukin-2," Annu. Rev. Immunol., Apr. 2008, 26:453-479.
Mao et al., "Inhibition of tumor-derived prostaglandin-e2 blocks the induction of myeloid-derived suppressor cells and recovers natural killer cell activity," Clin. Cancer. Res., Aug. 2014, 20(15):4096-4106.
Miller et al., "Successful adoptive transfer and in vivo expansion of human haploidentical NK cells in patients with cancer," Blood, Apr. 2005, 105(8):3051-3057.
Monteleone et al., "Interleukin-21 as a new therapeutic target for immune-mediated diseases," Trends in Pharmacological Sciences, Aug. 2009, 30(8):441-447.
Nagashima et al., "Stable transduction of the interleukin-2 gene into human natural killer cell lines and their phenotypic and functional characterization in vitro and in vivo," Blood, May 1998, 91(10):3850-3861.
Nagler et al., "The effects of IL-4 on human natural killer cells. A potent regulator of IL-2 activation and proliferation, " J. Immunol., Oct. 1988, 141(7):2349-2351.
Nair et al., "DNA Demethylation of the Foxp3 Enhancer Is Maintained through Modulation of Ten-Eleven-Translocation and DNA Methyltransferases," Mol. and Cells, Dec. 2016, 39(12):888-897.
Olson et al., "NK cells mediate reduction of GVHD by inhibiting activated, alloreactive T cells while retaining GVT effects," Blood, May 2010, 115(21):4293-4301.
Orr & Lanier., "Natural killer cell education and tolerance," Cell, Sep. 2010, 142(6):847-856.
Parkhurst et al., "Adoptive transfer of autologous natural killer cells leads to high levels of circulating natural killer cells but does not mediate tumor regression," Clin. Cancer. Res., Oct. 2011, 17(19):6287-6297.
Parrish-Novak et al., "Interleukin 21 and its receptor are involved in NK cell expansion and regulation of lymphocyte function," Nature, Nov. 2000, 408(6808):57-63.
PCT International Preliminary Report on Patentability in International Application No. PCT/US17/33585, mailed on Nov. 20, 2018, 8 pages.
PCT International Search Report and Written Opinion in Application No. PCT/US17/33585, mailed on Nov. 28, 2017, 16 pages.
Pegram et al., "Adoptive transfer of gene-modified primary NK cells can specifically inhibit tumor progression in vivo," J. Immunol., Sep. 2008, 181(5):3449-3455.
Puskas et al., "Development of an attenuated interleukin-2 fusion protein that can be activated by tumour-expressed proteases," Immunology, Jun. 2011, 133(2):206-220.
Qing & Stark., "Alternative activation of STAT1 and STAT3 in response to interferon-gamma," J. Biol. Chem., Oct. 2004, 279(40):41679-41685.

(56) References Cited

OTHER PUBLICATIONS

Rickert et al., "The structure of interleukin-2 complexed with its alpha receptor," Science, Jun. 2005, 308(5727):1477-1480.
Roncador et al., "Analysis of FOXP3 protein expression in human CD4+CD25+ regulatory T cells at the single-cell level," Eur J Immunol 2005;35(6): 1681-1691.
Rubnitz et al., "NKAML: a pilot study to determine the safety and feasibility of haploidentical natural killer cell transplantation in childhood acute myeloid leukemia," J. Clin. Oncol., Feb. 2010, 28(6):955-959.
Shahinian et al., "Differential T cell costimulatory requirements in CD28-deficient mice," Science, Jul. 1993, 261(5121):609-612.
Sharma et al., "Reprogrammed Foxp3+ regulatory T cells provide essential help to support cross-presentation and CD8+ T cell priming in naive mice," Immunity, Dec. 2010, 33(6):942-954.
Shevach, "Regulatory T cells in autoimmunity*," Annu. Rev. Immunol., 2000, 18:423-449.
Smigiel et al., "CCR7 provides localized access to IL-2 and defines homeostatically distinct regulatory T cell subsets," J. Exp. Med., Jan. 2014, 211(1):121-136.
Spolski, "Interleukin-21: a double-edged sword with therapeutic potential," Nat. Rev. Drug. Discov., May 2014, 13(5):379-395.
Stauber et al., "Crystal structure of the IL-2 signaling complex: paradigm for a heterotrimeric cytokine receptor," Proc. Natl. Acad. Sci., Feb. 2006, 103(8):2788-2793.
Storb et al., "Should methotrexate plus calcineurin inhibitors be considered standard of care for prophylaxis of acute graft-versus-host disease?" Biol. Blood Marrow Transplant, Jan. 2010, 16(1 Suppl):S18-27.
Strengell et al., "IL-21 in synergy with IL-15 or IL-18 enhances IFN-gamma production in human NK and T cells," J. Immunol., Jun. 2003, 170(11):5464-5469.
Strengell et al., "IL-21 up-regulates the expression of genes associated with innate immunity and Th1 response," J. Immunol., Oct. 2002, 169(7):3600-3605.
Suck et al., "NK-92: an 'off-the-shelf therapeutic' for adoptive natural killer cell-based cancer immunotherapy," Cancer Immunol. Immunother., Apr. 2016, 65(4):485-492.
Suerth et al., "Genetic modification of lymphocytes by retrovirus-based vectors," Curr. Opin. Immunol., Oct. 2012, 24(5):598-608.
Sung & Chao., "Concise Review: Acute Graft-Versus-Host Disease: Immunobiology, Prevention, and Treatment," Stem Cells Translational Medicine, Jan. 2013, 2(1):25-32.
Tai et al., "Anti-CS1 humanized monoclonal antibody HuLuc63 inhibits myeloma cell adhesion and induces antibody-dependent cellular cytotoxicity in the bone marrow milieu," Blood, Aug. 2008, 112(4):1329-1337.
Takahashi et al., "SOCS1 is essential for regulatory T cell functions by preventing loss of Foxp3 expression as well as IFN-{ gamma} and IL-17A production," J. Exp. Med., Sep. 2011, 208(10):2055-2067.
Takeshita et al., "Cloning of the gamma chain of the human IL-2 receptor," Science, Jun. 1992, 257(5068):379-382.
Tam et al., "Characterization of Genetically Altered, Interleukin 2-Independent Natural Killer Cell Lines Suitable for Adoptive Cellular Immunotherapy," Human Gene Therapy, May 1999, 10(8):1359-1373.
Tang & Bluestone, "Regulatory T-cell physiology and application to treat autoimmunity: Qizhi Tang Jeffrey A. Bluestone," Immunol. Rev., Aug. 2006, 212(1):217-237.
Taylor et al., "The infusion of ex vivo activated and expanded CD4+ CD25+ immune regulatory cells inhibits graft-versus-host disease lethality," Blood, May 2002, 99(10):3493-3499.
Terme et al., "Natural killer cell-directed therapies: moving from unexpected results to successful strategies," Nat. Immunol., May 2008, 9(5):486-494.
Tirapu et al., "Low surface expression of B7-1 (CD80) is an immunoescape mechanism of colon carcinoma." Cancer. Res., Feb. 2006, 66(4):2442-2450.

Tonn et al., "Treatment of patients with advanced cancer with the natural killer cell line NK-92," Cytotherapy, Sep. 2013, 15(12):1563-1570.
Tortorella et al., "Viral subversion of the immune system," Annu. Rev. Immunol., Apr. 2000, 18:861-892.
Townsend et al., "Tumor rejection after direct costimulation of CD8+ T cells by B7-transfected melanoma cells," Science, Jan. 1993, 259(5093):368-370.
Valés-Gómez et al., "Kinetics of interaction of HLA-C ligands with natural killer cell inhibitory receptors," Immunity, Sep. 1998, 9(3):337-344.
Vidal et al., "Natural killer cell responses during viral infections: flexibility and conditioning of innate immunity by experience," Curr. Opin. Virol., 2011;1(6):497-512.
Vihinen et al., "Accuracy of protein flexibility predictions," Proteins, Jun. 1994, 19(2):141-149.
Vihinen, "Relationship of protein flexibility to thermostability," Protein Eng., Nov. 1987, 1(6):477-480.
Voss et al., "Characterization of the interleukin 2 receptors (IL-2R) expressed on human natural killer cells activated in vivo by IL-2: association of the p64 IL-2R gamma chain with the IL-2R beta chain in functional intermediate-affinity IL-2R," J. Exp. Med., Jul. 1992, 176(2):531-541.
Wang et al., "Regulation of surface and intracellular expression of CTLA-4 on human peripheral T cells," Scand. J. Immunol., Nov. 2001, 54(5):453-458.
Yang et al., "Molecular antagonism and plasticity of regulatory and inflammatory T cell programs," Immunity, Jul. 2008, 29(1):44-56.
Zeng et al., "The molecular basis of IL-21-mediated proliferation," Blood, May 2007, 109(10):4135-4142.
Zhang et al., "Activation and functional specialization of regulatory T cells lead to the generation of Foxp3 instability," J. Immunol., Apr. 2017, 198(7):2612-2625.
EP Office Action in European Appln. No. 17800257.2, dated Oct. 1, 2020, 3 pages.
Eicher et al., "IL-2Ra on One Cell Can Present IL-2 to IL-2Rb/gc on Another Cell to Augment IL-2 Signaling, " J Immunol., 1998, 161:5430-5437.
Office Action in Chinese Appln. No. 201780044474.8, dated Oct. 9, 2021, 21 pages (with English translation).
Office Action in Japanese Appln. No. 2018-560491, dated Feb. 8, 2022, 6 pages (with English translation).
Andrews et al., "LAG3 (CD223) as a cancer immunotherapy target," HHS Public Access Author Manuscript, doi: 10.1111/imr.12519, published online Mar. 1, 2018; published in final edited form as: Immunol Rev., Mar. 2017, 276(1):80-96, 34 pages.
Antonia et al., "Immunotherapy: Beyond Anti-PD-1 and Anti-PD-L1 Therapies," Am Soc Clin Oncol Educ Book, May 2016, 36:e450-8.
Brusko et al., "Functional defects and the influence of age on the frequency of CD4+ CD25+ T-cells in type 1 diabetes," Diabetes, May 2005, 54(5):1407-14.
Chabannon et al., "Manufacturing Natural Killer Cells as Medicinal Products," Front Immunol, Nov. 2016, 7:504, 9 pages.
Chen et al., "Abstract 761: Il2 and Il21 Chimeric Signaling in Nk92Cirb21 Enhances Anti-Tumor Activity and Safety of Live Nk92 Cells for Cancer Immunotherapy," Abstract, Presented at Proceedings of the ASGCT 23rd Annual Meeting, Virtual, May 12-15, 2020; Mol Ther, Apr. 28, 2020, 28(4S1):333-334.
Cheng et al., "Establishment, characterization, and successful adaptive therapy against human tumors of NKG cell, a new human NK cell line," Cell Transplant, 2011, 20(11-12):1731-46, 22 pages.
Cheng et al., "NK cell-based immunotherapy for malignant diseases," Cellular & Molecular Immunology, May 2013, 10(3):230-252.
Davis et al., "Natural Killer Cell Adoptive Transfer Therapy: Exploiting the First Line of Defense Against Cancer," HHS Public Access Author Manuscript, doi: 10.1097/PPO.0000000000000156, published online Feb. 23, 2016; published in final edited form as: Cancer J., Nov.-Dec. 2015, 21(6):486-491, 13 pages.
Fletcher et al., "CD39+Foxp3+ regulatory T Cells suppress pathogenic Th17 cells and are impaired in multiple sclerosis," J Immunol., Dec. 2009, 183(11):7602-10.

(56) References Cited

OTHER PUBLICATIONS

Granucci et al., "A contribution of mouse dendritic cell-derived IL-2 for NK cell activation," J Exp Med., Aug. 2004, 200(3):287-95.
Grinberg-Bleyer et al., "IL-2 reverses established type 1 diabetes in NOD mice by a local effect on pancreatic regulatory T cells," J Exp Med., Aug. 2010, 207(9):1871-8.
Harjunpää and Guillerey, "TIGIT as an emerging immune checkpoint," Clin Exp Immunol., Dec. 2019, 200(2):108-119.
Harnack et al., "Natural Killer Cell Line YT Exerts Cytotoxicity Against CD86+ Myeloma Cells," Anticancer Research, Feb. 2011, 31(2):475-479.
International Preliminary Report on Patentability in International Appln. No. PCT/US2022/071948, mailed Nov. 9, 2023, 7 pages.
International Search Report and Written Opinion in International Appln. No. PCT/US2022/071948, mailed Sep. 1, 2022, 9 pages.
Jounaidi et al., "Tethering IL2 to Its Receptor IL2Rβ Enhances Antitumor Activity and Expansion of Natural Killer NK92 Cells," HHS Public Access Author Manuscript, doi: 10.1158/0008-5472. CAN-17-1007, published online Oct. 28, 2018; published in final edited form as: Cancer Research, Nov. 2017, 77(21):5938-51, 29 pages.
Kasaian et al., "IL-21 limits NK cell responses and promotes antigen-specific T cell activation: a mediator of the transition from innate to adaptive immunity," Immunity, Apr. 2002, 16(4):559-69.
Klingermann et al., "Natural Killer Cells for Immunotherapy— Advantages of the NK-92 Cell Line over Blood NK Cells," Front. Immunol., Mar. 2016, 7:91, 7 pages.
Koka et al., "Cutting edge: murine dendritic cells require IL-15Rα to prime NK cells," J Immunol., Sep. 2004, 173(6):3594-8.
Kuppusamykrishnan et al., "Analysis of 58 Families of Holins Using a Novel Program, PhyST," J Mol Microbioi Biotechnology, 2016, 26(6):381-388.
Ljunggren and Malmberg, "Prospects for the use of NK cells in immunotherapy of human cancer," Nat Rev Immunol., May 2007, 7(5):329-39.
Löhr et al., Transforming Growth Factor-β1 Induces Desmoplasia in an Experimental Model of Human Pancreatic Carcinoma, Cancer Res., Jan. 2001, 61(2):550-5.
Lyssuk et al., "Reduced number and function of CD4+ CD25$^{high}$FoxP3+ regulatory T cells in patients with systemic lupus erythematosus," Adv Exp Med Biol., 2007, 601:113-9.
Marek-Trzonkowska et al., "Administration of CD4+CD25$^{high}$CD127- regulatory T cells preserves β-cell function in type 1 diabetes in children," Diabetes Care, Sep. 2012, 35(9):1817-1820.
Needleman and Wunsch, "A general method applicable to the search for similarities in the amino acid sequence of two proteins," J. Mol. Biol., Mar. 1970, 48(3):444-453.
Riley et al., "Human T regulatory cell therapy: take a billion or so and call me in the morning," Immunity, May 2009, 30(5):656-665.
Ross et al., "Anticancer antibodies," Am J Clin Pathol., Apr. 2003, 119(4):472-485.
Singer et al., "Regulatory T cells as immunotherapy," Front Immunol., Feb. 2014, 5:46, 10 pages.
Storz, "Intellectual property issues of immune checkpoint inhibitors," Mabs, Jan. 2016, 8(1):10-26.
Sugiyama et al., "Dysfunctional blood and target tissue CD4+ CD25$^{high}$ regulatory T cells in psoriasis: mechanism underlying unrestrained pathogenic effector T cell proliferation," J Immunol., Jan. 2005, 174(1):164-73.
Tang et al., "Central role of defective interleukin-2 production in the triggering of islet autoimmune destruction," Immunity, May 2008, 28(5):687-97.
Tarhini and Iqbal, "CTLA-4 blockade: therapeutic potential in cancer treatments," Onco Targets Ther., Jun. 2010, 3:15-25.
Tonn et al., "Cellular immunotherapy of malignancies using the clonal natural killer cell line NK-92," J Hematother Stem Cell Res., Aug. 2001, 10(4):535-44.
Tsuchiyama et al., "Characterization of a novel human natural killer-cell line (NK-YS) established from natural killer cell lymphoma/ leukemia associated with Epstein-Barr virus infection," Blood, Aug. 1998, 92(4):1374-83.
Yagita et al., "A novel natural killer cell line (KHYG-1) from a patient with aggressive natural killer cell leukemia carrying a p53 point mutation," Leukemia, Apr. 2000, 14:922-930.
Yan et al., "Antileukemia activity of a natural killer cell line against human leukemias," Clin Cancer Res., Nov. 1998, 4(11):2859-68.
Yodoi et al., "TCGF (IL 2)-receptor inducing factor(s). I. Regulation of IL 2 receptor on a natural killer-like cell line (YT cells)," J Immunol., Mar. 1985, 134(3):1623-1630.

* cited by examiner

TETHERED INTERLEUKIN-2 TO ITS RECEPTOR IL-2RBETA, A PLATFORM TO ENHANCE NATURAL KILLER AND REGULATORY T CELL ACTIVITY

CLAIM OF PRIORITY

This application is a § 371 National Stage Application of PCT/US2017/033585, filed May 19, 2017, which claims the benefit of U.S. Provisional Application Serial Nos. 62/338,757, filed on May 19, 2016, and 62/471,456, filed on Mar. 15, 2017. The entire contents of the foregoing are incorporated herein by reference.

STATEMENT OF FEDERALLY SPONSORED RESEARCH

This invention was made with government support under Grant No. GM058448 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 15, 2018, is named 29539-0282US1_SL.txt and is 44,627 bytes in size.

TECHNICAL FIELD

Described herein are Natural killer (NK) cells that express chimeric proteins comprising IL2, IL2Rβ and IL21R (e.g., CIRB21); and/or a chimera comprising IL2, IL2Rβ, and CD28 (e.g., CIRB28), and methods of use thereof, e.g., to treat subjects with cancer, GVHD, and autoimmune diseases.

BACKGROUND

Natural killer (NK) cells are lymphocytes endowed with the innate ability to attack malignant and virus infected cells without prior exposure to specific antigens(1-3). Several interleukins, and in particular IL2, activate and expand critical immune cells such as T-cells and NK cells(4). Systemic IL2 supplementation could therefore enhance immunity in a variety of diseases ranging from cancer to viral infection. However, in cancer patients, tumor cells and their microenvironment (TME) often repress NK cells anti-tumor activity by orchestrating a multitude of escape mechanisms (5).

Clinical trials using high dose IL2 infusions have met limited success due to severe side effects that mimic sepsis (6-8), while low-dose IL2 efficacy is limited by the short half-life (less than 10 min) of IL2 in vivo(9), and due to depletion of low IL2 doses by T-regs and other lymphoid cells(10). A number of strategies based on IL2 have aimed to enhance NK cytotoxicity while reducing toxicity in patients, with limited efficacy. Cultured ex-vivo NK cells can be activated and induced to proliferate by exposure to IL2 before transfer in vivo. Ex-vivo activated autologous NK cells display less anti-tumor efficacy(11) than NK cells from allogeneic donors(12), because self class I HLA signaling suppresses NK cytotoxicity and cytokine release(13). However, in order for allogeneic donor NK cells to be effective, pre-transfer lymphodepletion to reduce competition for growth factors and cytokines is required(14,15). Moreover, systemic IL2 administration is needed to sustain NK cytotoxicity after in vivo transfer, exposing patients to systemic side effects.

Past therapeutic efforts to express endogenous IL2 in NK cells showed limited success with micro metastatic models and were not as efficacious as NK cells stimulated with exogenous IL2(16). Similarly, effort to express membrane-bound endogenous IL2 did not show any advantage above parental NK92 cells(17). The limited success of several immunotherapy strategies using NK cells could be explained by the failure of activated NK cells to outcompete T-regs for cytokines in the host and the immunosuppressive effect of the TME, which includes myeloid derived suppressor cells (MDSCs). Both MDSCs and T-regs mediate NK cell functions suppression either by direct contact or by secretion of TGFβ1(18,19).

SUMMARY

Interleukin-2 (IL2) is an immunostimulatory cytokine for key immune cells including T cells and natural killer (NK) cells. Systemic IL2 supplementation could enhance NK-mediated immunity in a variety of diseases ranging from neoplasms to viral infection. However, its systemic use is restricted by its serious side effects and its efficacy may be limited by activation of T-regulatory (T-regs) cells. IL2 signaling is mediated through interactions with a high affinity multi-subunit receptor complex containing IL2Rα, IL2Rβ and IL2Rγ. Adult NK cells may express only IL2Rβ and IL2Ry subunits and are therefore relatively insensitive to IL2. To overcome these limitations, we created a novel chimeric IL2-IL2Rβ (CIRB) fusion protein of IL2 and its receptor IL2Rβ joined via a peptide linker. NK92 cells expressing CIRB (NK92$^{CIRB}$) are highly activated and expand indefinitely without exogenous IL2. They are highly cytotoxic, and were resistant to TGF-β1 and dexamethasone. Furthermore, CIRB induced substantial expression of natural cytotoxicity receptors NKP44, NKP46 and NKP30 as well as CD16, which enhanced NK cytotoxicity with Trastuzumab via antibody dependent pathways against HER2 positive cells. When compared to an IL2 secreting NK92 cell line (NK92$^{IL2}$), NK92$^{CIRB}$ cells display superior in vivo anti-tumor effect and survival in mice (at least 3 weeks). This novel chimera eliminates the need for both IL2Ra and IL2Rβ expression and offers an alternative to exogenous IL2 stimulation. Collectively, the present data show that tethering IL2 to its receptor IL2Rβ offers a new platform that may be useful in selectively activating and enhancing immune therapy.

Thus, provided herein are fusion proteins comprising interleukin 2 (IL2) fused to the N-terminus of interleukin 2 receptor beta (IL2R), with an intervening linker therebetween. In some embodiments, the IL2 comprises SEQ ID NO:34, and/or the IL2Rβ comprises amino acids 27-551 of SEQ ID NO:35. In some embodiments, the intervening linker between IL2 and the N-terminus of IL2Rβ comprises an extracellular domain of IL2Rα. In some embodiments, the extracellular domain of IL2Rα comprises SEQ ID NO:28.

In some embodiments, the fusion protein also includes a cytoplasmic domain of IL21R at the C-terminus of IL2Rβ, optionally with an intervening linker therebetween. In some embodiments, the cytoplasmic domain of IL21R comprises amino acids 254-538 of SEQ ID NO:36.

In some embodiments, the fusion protein also includes an activation domain of CD28 at the C-terminus of the IL2Rβ portion, optionally with an intervening linker therebetween.

In some embodiments, the activation domain of CD28 comprises amino acids 180 to 220 of SEQ ID NO:38.

Also provided herein are nucleic acids encoding the fusion proteins described herein, as well as expression vectors comprising the nucleic acids, preferably with one or more regulatory regions for expression of a fusion protein described herein.

Further, provided herein are isolated natural killer (NK) cells (e.g., CD3-CD56+ lymphocytes) expressing a fusion protein as described herein, preferably wherein the NK cell is CD3-CD56+ lymphocyte also expresses CD16 and optionally NKP44, NKP46 and NKP30, and the use thereof in treating cancer.

Also provided are Regulatory T cells (T-regs) expressing fusion proteins comprising interleukin 2 (IL2) fused to the N-terminus of interleukin 2 receptor beta (IL2R), with an intervening linker therebetween, and an activation domain of CD28 at the C-terminus of the IL2Rβ portion, optionally with an intervening linker therebetween. Preferably the Tregs are CD4+CD25+, e.g., CD4+CD25+CD127- Tregs (e.g., CD4+CD25highCD127-ICOS+ for atopy Tregs or CD4+CD25+CD127- CD62L+ for GVHD), and are optionally FOXP3+ as well. Also provided is the use thereof in treating GVHD and autoimmune disease, e.g., for depleting alloreactive T cells.

Further, provided herein are methods for treating a subject, preferably a human subject, who has cancer (e.g., who has been diagnosed with cancer), comprising administering a therapeutically effective amount of natural killer (NK) cells expressing a fusion protein as described herein, preferably wherein the NK cells are CD3-CD56+ lymphocyte also expresses CD16 and optionally NKP44, NKP46 and NKP30. The NK cells can be formulated and/or administered in a physiologically acceptable composition, e.g., as described herein, e.g., formulated to be administered intravenously.

In some embodiments, the subject has a solid tumor.

In some embodiments, the methods include administering one or more of an anti-tumor monoclonal antibody or a checkpoint inhibitor.

In some embodiments, the NK cells are administered intravenously.

In some embodiments, the NK cells are subjected to 500 to 1000 cGy of gamma irradiation prior to being administered.

Also provided herein are methods for treating a subject who has GVHD or an autoimmune disease, comprising administering a therapeutically effective amount of regulatory T (T-reg) cells expressing fusion proteins comprising interleukin 2 (IL2) fused to the N-terminus of interleukin 2 receptor beta (IL2R), with an intervening linker therebetween, and an activation domain of CD28 at the C-terminus of the IL2Rβ portion, optionally with an intervening linker therebetween. Preferably the Tregs are CD4+CD25+, e.g., CD4+CD25+CD127- Tregs (e.g., CD4+CD25highCD127-ICOS+ for atopy Tregs or CD4+CD25+CD127-CD62L+ for GVHD), and are optionally FOXP3+ as well.

In some embodiments, the T-reg cells are administered intravenously.

In some embodiments, the NK cells are subjected to 500 to 1000 cGy of gamma irradiation prior to being administered.

Also provided are NK cells expressing a fusion protein as described herein, for use in treating a subject, preferably a human subject, who has cancer, e.g., a solid tumor. In some embodiments the subject is also administered one or more of an anti-tumor monoclonal antibody or a checkpoint inhibitor. In some embodiments, the NK cells are formulated to be administered intravenously. In some embodiments, the NK cells are subjected to 500 to 1000 cGy of gamma irradiation prior to being administered.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
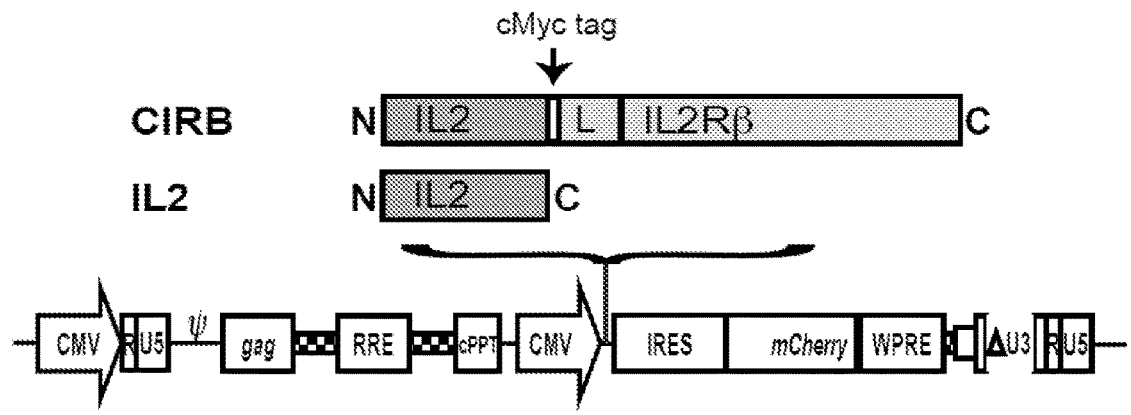
FIG. 1—Diagrams of the Human IL2 and the chimera IL2 fused with receptor IL2Rβ (CIRB) in lentiviral constructs. A Linker (L) composed of the cMyc tag (EQKLISEEDL SEQ ID NO: 29) and a fragment of the extracellular domain of IL2 receptor alpha (EMETSQFPGEEKPQASPEGRPE-SETSC SEQ ID NO: 28), joins IL2 and its receptor IL2Rβ.

The present compositions and methods selectively activate and expand NK cells without exogenous IL2, while maintaining NK cytotoxicity and proliferation both in vitro and in vivo, circumvent the requirement of IL2Rα and its lack of expression in NK cells, thus avoiding IL2 off-target effects, cytokine competition, and activation of down-regulating lymphoid cells like T-regs.

IL2 will bind to either low affinity receptor IL2Rα (CD25) (21) or to intermediary affinity receptor IL2Rβ (CD122) with the common IL2Rγ chain (CD132) (22,23) and to all, to form a high affinity quaternary complex(24). Adult NK cells may express only IL2Rβ and IL2Rγ subunits (25) and are, therefore, relatively insensitive to low doses of IL2, but acquire sensitivity upon IL2Rα expression(26). A recently developed IL2 "superkine" (27) that bypasses IL2Rα by binding directly and with high affinity to IL2Rβ produced better antitumor effects than wild type IL2 in mice. However, it still causes some form of pulmonary edema.

The novel chimera CIRB described herein comprises IL2 and its receptor IL2Rβ, joined by a peptide linker derived from the extracellular domain of IL2Rα. The linker was computationally determined as reasonably flexible, without adversely affecting the chimera stability which is generally inversely correlated to flexibility(28). When introduced in NK92 cells, CIRB induces indefinite cell expansion and conferred an in vitro cytotoxicity similar or higher than that elicited by IL2 expression. In vivo, the anticancer activity of NK92$^{CIRB}$ against mid-size solid tumors was substantially superior to that elicited by NK92$^{IL2}$. Additionally, CIRB confers, in contrast to IL2, substantial resilience to TGFβ1, dexamethasone as well as IL4. This advantage could be crucial in the TME where TGFβ1 is secreted by a variety of cells including cancer associated fibroblasts(29), and exists in a membrane bound form on T-regs to induce anergy of NK cells(30), or by MDSCs to inhibit NKG2D expression, and IFN-γ production in NK cells(31). Cancer cells also regularly shed tumor-derived exosomes (TDEs) containing a membrane bound form of TGFβ1 resulting in the down regulation of NKG2D(32), and the inhibition of IL2 signaling(33). TGFβ1 mediates NK inhibition by an induced microRNA (miR)-183 which represses the co-activator/adapter DAP12 expression, thus destabilizing several activation signals in NK cells(34). CIRB expression in NK92$^{CIRB}$ cells also provides resistance to dex while NK92$^{IL2}$ cells were eliminated. Dex impairs the function of lymphocytes in part by suppressing IL2 production from CD4+ T cells, and reducing the activation receptors NKG2D and Nkp46 in NK cells (35). Glucocorticoid hormones can interfere with macrophage activation and antigen presentation, repress the transcription of several pro-inflammatory cytokines, chemokines, cell adhesion molecules and other enzymes involved in the inflammatory response(36). The extreme sensitivity of NK92$^{IL2}$ to dex, could be explained by the previously reported destabilization of IL2 RNA(37). This RNA destabilization could potentially occur in NK92$^{IL2}$ cells but not when it is fused with IL2Rβ RNA as in NK92$^{CIRB}$ cells.

Figure 5A:
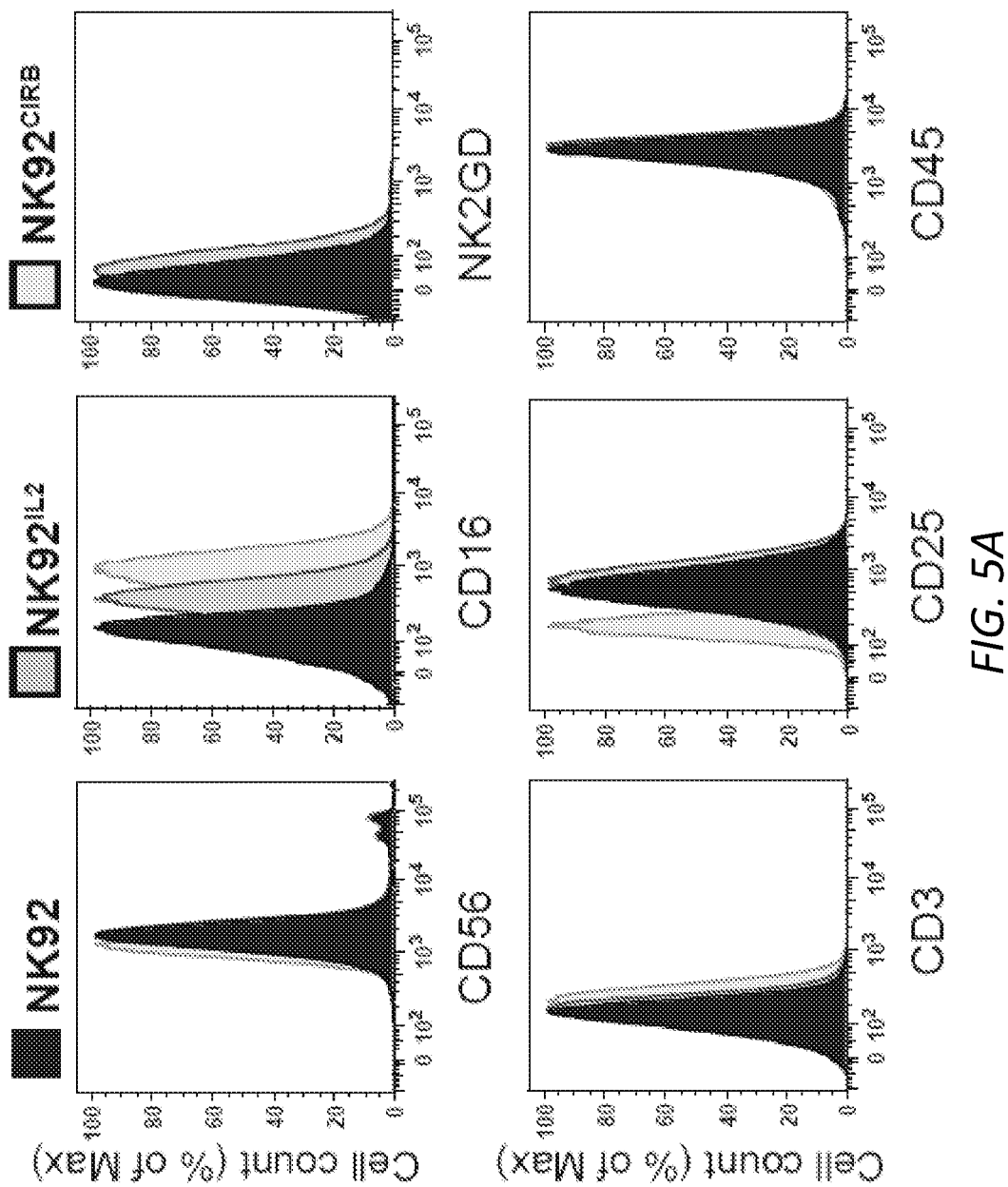
FIGS. 5A-D—NK92, NK92$^{IL2}$ and NK92$^{CIRB}$ cell lines phenotype. A, Flow cytometry shows the increased cell surface density of CD16 in NK92$^{IL2}$ and NK92$^{CIRB}$ and the low expression of CD25 in NK92$^{CIRB}$, Human primary NK cells (hNK) phenotypic expression of NKG2D, CD25 and CD16 in comparison to NK92, NK92$^{IL2}$ and NK92$^{CIRB}$. C, direct cytotoxicity and ADCC activity mediated by effector NK92, NK92$^{IL2}$ and NK92$^{CIRB}$ cells against HER2 positive BT474 cell line at E/T ratio of 2:1 when incubated with Trastuzumab (1 ug/ml). Data are presented as cell number percentage relative to NK cells-free controls, mean+SE values for triplicate samples. Statistical differences were determined by one-way Anova test ((*P<0.05). D, expression profiles of NKP30, NKP44, NKP46, Granzyme-B, Perforin-1, TNF-α, and INF-γ in NK cells lines. Data are presented as mean+SE values for triplicate samples. Two tails t-test analysis was used to evaluate statistical differences.

CIRB and to a lesser degree the stable expression of IL2 allowed substantial CD16 expression in NK92 cell line. However, exogenous recombinant IL2 was not able to mediate such expression. Similarly, NK92-MI cell line which produces and secretes IL2 was found deficient in CD16, as previously reported(38). When combined with Trastuzumab, CD16 expression further enhanced NK92$^{CIRB}$ and NK92$^{IL2}$ cytotoxicity by ADCC. CIRB induced substantial expression of NCRs, NKP44 (9 fold), NKP46 (1.4 fold) and NKP30 (1.7 fold) as well as a modest but significant increase in INFγ. Finally, Granzyme-B expression declined substantially in NK92$^{IL2}$. Interestingly, CD25 expression declined dramatically in NK92$^{CIRB}$, as it is unnecessary in the presence of the chimera CIRB (FIG. 5A).

Figure 9:
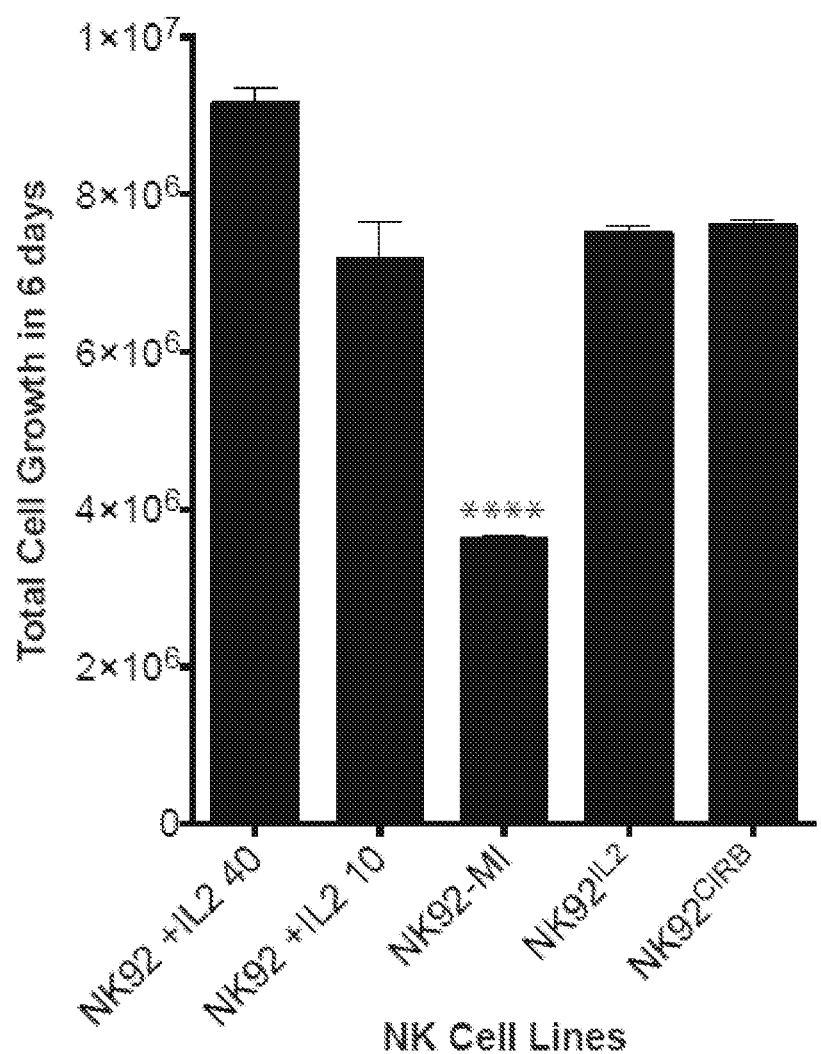
FIG. 9—Cell growth of NK92$^{IL2}$ and NK92$^{CIRB}$ cell lines—NK92$^{IL2}$ and NK92$^{CIRB}$ cell lines showed fast recovery after freezing and excellent survival after subjection to multiple freezing and plating in tissue culture. NK92. NK92$^{IL2}$, NK92$^{CIRB}$ and IL2-activated NK92 (10 IU/ml), growths were similar after six days and slightly higher for NK92 at 401 U/ml. NK92-MI cells showed the slowest growth during the same period.

Current genetic modifications introducing CD16 in NK cells were shown to increase NK cell mediated ADCC against multiple myeloma when combined with Elotuzumab (39). The fact that CD16 was induced only in NK92$^{CIRB}$ and NK92$^{IL2}$ but not in NK92-MI or NK92 stimulated with IL2 could be possibly explained by the persistent IL2 signaling that somehow translates into stronger activation and growth NK92$^{CIRB}$ and NK92$^{IL2}$. In fact, the growth rates of both NK92$^{CIRB}$ and NK92$^{IL2}$ were 2-fold that of NK92-MI (FIG. 9), suggesting a higher level of activation. Another indication of higher activation of NK92$^{CIRB}$ and NK92$^{IL2}$ is the dramatic induction of NKP44, compared to parental NK92 stimulated with IL2 for 48 hours.

Additionally, NK92$^{CIRB}$ can proliferate in vivo far longer and also have a better survival after irradiation than NK92$^{IL2}$ cells. They also surpass that of NK92-MI when exposed to similar conditions (38). In vitro, NK92$^{IL2}$ cells secrete sufficient IL2 to sustain their activation and proliferation. However, they may not be able to produce enough IL2 extracellular concentrations to sustain activation and proliferation in vivo. This could be compounded by the competition for IL2 by T-regs and other immune cells in an immune competent animal.

Thus the novel chimeras described herein comprising CIRB endow NK92 cells with very useful attributes that improve immune therapy of cancer and potentially viral infections.

Cellular immunotherapy using donor NK cells is an emerging field that could achieve significant anti-cancer effects, safely and without the risk of inducing graft-versus-host disease (GVHD). This safety feature as well as the off tumor/on target toxicity are currently hindering the success of CAR-T technology(40). Several NK cell lines (Khyg-1, NKL, NKG, NK-YS, YT, YTS and HANK-1 cells) are currently used in preclinical studies. However, only the NK92 cell line has been extensively evaluated for its safety and efficacy in clinical settings(41,42). NK92 cells are CD56+, CD3− and CD16− and require IL2 for growth and activation(43). Unlike primary NK cells, NK92 cells and other NK cell lines constitute a stable and homogenous population. They are amenable to genetic modification by lentiviruses, a gene transfer platform that has shown a good safety profile for lymphocytes(44). Many encouraging advances have been achieved in NK cell-directed immunotherapy(45). However, the increasing demand for NK cells expansion ex-vivo requires both highly activated cells and reduced costs of cell expansion. Moreover, infused cells must have higher activation potential and possess favorable characteristics against immunosuppressors found in the TME.

The present strategy includes fusing interleukins to their receptors in the CIRB, CIRB28, and CIRB21 chimeras achieves better cytokine activation, with specificity, and without systemic toxicity or competition by other cellular components of the immune system. Self-activation of NK cells provides several distinguishing features such as resilience to TGFβ1 or glucocorticoid hormones, substantial expression of CD16, higher survival after irradiation and a superior antitumor activity in vivo.

Chimeric Proteins

The present disclosure provides chimeras as described herein, e.g., a chimera comprising IL2 and IL2Rβ (e.g., CIRB); a chimera comprising IL2, IL2Rβ and IL21R (e.g., CIRB21); and/or a chimera comprising IL2, IL2Rβ, and CD28 (e.g., CIRB28). All of the fusion proteins described herein can be generated using standard molecular biological procedures, e.g., for manipulating and expressing recombinant DNA. See, e.g., *Current Protocols in Molecular Biology*, Ausubel, F. M. et al. (eds.) John Wiley & Sons (1995), and Green and Sambrook, *Molecular Cloning: A Laboratory Manual* (Fourth Edition), Cold Spring Harbor Laboratory Press (Jun. 15, 2012) and supplements thereof, and other standard laboratory manuals. The chimeras can be expressed, e.g., stably expressed, in an NK cell, e.g., a primary or cultured NK cell. The cells are then infused into a subject, e.g., a subject who has (e.g., has been diagnosed with) cancer.

Provided hereinbelow are exemplary sequences for the various domains that make up the chimeras described herein. In some embodiments, the sequences used are at least 80% identical to the exemplary sequence as defined herein. In some embodiments, the sequences are at least 85%, 90%, 95%, 99% or 100% identical.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

IL2-IL2Rβ (CIRB)

The fusion proteins described herein include, inter alia, IL2 and IL2Rβ fused together with an intervening linker. Sequences for IL2 are known in the art; an exemplary human IL2 precursor sequence is shown in SEQ ID NO:34.

```
                                                           (SEQ ID NO: 34)
  1 MYRMQLLSCI ALSLALVTNS APTSSSTKKT QLQLEHLLLD LQMILNGINN YKNPKLTRML

61 TFKFYMPKKA TELKHLQCLE EELKPLEEVL NLAQSKNFHL RPRDLISNIN VIVLELKGSE

121 TTFMCEYADE TATIVEFLNR WITFCQSIIS TLT
```

Amino acids 1-20 are a signal sequence, and so can be replaced by other signal sequences if desired. An exemplary nucleic acid sequence for human IL2 is Linker sequences known in the art can be used between the various domains of the fusion protein; for example, one, two, three, four, five or more GGGS sequences can be used. In preferred embodiments, the linker between IL2 and the N-terminus of IL2Rβ comprises the extracellular domain of IL2Rα (EMETSQFPGEEKPQASPEGRPESETSC (SEQ ID NO:28). A tag, e.g., a cMyc tag (EQKLISEEDL (SEQ ID NO:29)), can also be added, e.g., between IL2 and the linker. An exemplary nucleic acid sequence encoding IL2 is available in GenBank at Acc. No. NM_000586.3.

Sequences for IL2Rβ are also known in the art; an exemplary human IL2Rβ precursor sequence is shown in SEQ ID NO:35.

IL2-IL2Rβ-IL-21 (CIRB21)

Figure 11:
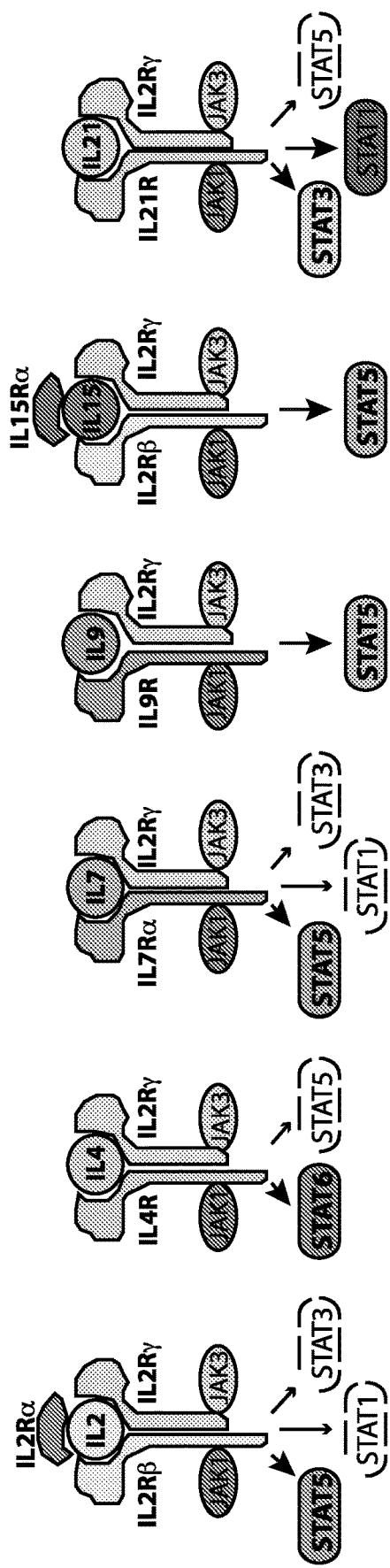
FIG. 11. A schematic illustration showing signaling through JAK-STAT pathway using common signaling chain IL2Rg.
Figure 13:
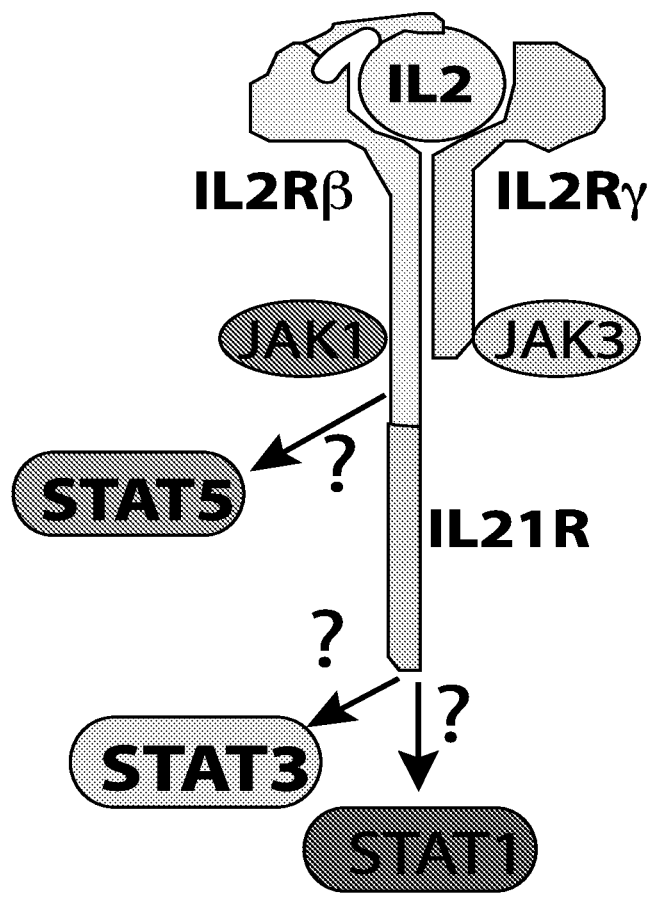
FIG. 13. Exemplary schematic of an IL2-IL2Rβ-IL21 chimera (CIRB21).

Interleukins IL4, IL7, IL9, IL15 and IL21 belong to the same family as IL2, and use the same common IL2Rg. They all have their own private receptors, except for IL2 and IL15, which use IL2Rβ in addition to their own alpha receptors (FIG. 11). When soluble IL2, IL4, IL7, or IL21 were added to NK92 cells expressing the chimera NK92$^{CIRB}$, only IL21 dramatically enhance cytotoxicity against PC-3 cells. Thus the entire cytoplasmic domain of IL21R was cloned then added Head-to-Tail to the C-terminal of IL2Rβ in the chimera CIRB. This resulted in a novel IL2-IL2Rβ-IL21R chimera (called CIRB21, exemplified in FIG. 13). As shown herein, it was possible to emulate the activation signals from multiple cytokines that activate NK cells via different receptors by using only one ligand and a hybrid receptor.

```
                                                           (SEQ ID NO: 35)
  1 MAAPALSWRL PLLILLLPLA TSWASAAVNG TSQFTCFYNS RANISCVWSQ DGALQDTSCQ

61 VHAWPDRRRW NQTCELLPVS QASWACNLIL GAPDSQKLTT VDIVTLRVLC REGVRWRVMA

121 IQDFKPFENL RLMAPISLQV VHVETHRCNI SWEISQASHY FERHLEFEAR TLSPGHTWEE

181 APLLTLKQKQ EWICLETLTP DTQYEFQVRV KPLQGEFTTW SPWSQPLAFR TKPAALGKDT

241 IPWLGHLLVG LSGAFGFIIL VYLLINCRNT GPWLKKVLKC NTPDPSKFFS QLSSEHGGDV

301 QKWLSSPFPS SSFSPGGLAP EISPLEVLER DKVTQLLLQQ DKVPEPASLS SNHSLTSCFT

361 NQGYFFFHLP DALEIEACQV YFTYDPYSEE DPDEGVAGAP TGSSPQPLQP LSGEDDAYCT

421 FPSRDDLLLF SPSLLGGPSP PSTAPGGSGA GEERMPPSLQ ERVPRDWDPQ PLGPPTPGVP

481 DLVDFQPPPE LVLREAGEEV PDAGPREGVS FPWSRPPGQG EFRALNARLP LNTDAYLSLQ

541 ELQGQDPTHL V
```

Amino acids 1-26 are a signal sequence, and are preferably deleted in the present constructs, e.g., the sequence comprises amino acids 27-551 of SEQ ID NO:35. Exemplary nucleic acid sequences encoding IL2Rβ are available in GenBank at Acc. No. NM_000878.4 (Var. 1), NM_001346222.1 (Var. 2); and NM_001346223.1 (Var. 3). Variants 1, 2 and 3 encode the same protein.

In some embodiments, the present constructs include the cytoplasmic domain of IL21R at the C-terminus of the IL2Rβ portion (optionally with an intervening linker therebetween). Sequences for IL21R are also known in the art; an exemplary human IL21R precursor sequence is shown in SEQ ID NO:36.

```
                                                           (SEQ ID NO: 36)
  1 MPRGWAAPLL LLLLQGGWGC PDLVCYTDYL QTVICILEMW NLHPSTLTLT WQDQYEELKD

61 EATSCSLHRS AHNATHATYT CHMDVFHFMA DDIFSVNITD QSGNYSQECG SFLLAESIKP

121 APPFNVTVTF SGQYNISWRS DYEDPAFYML KGKLQYELQY RNRGDPWAVS PRRKLISVDS

181 RSVSLLPLEF RKDSSYELQV RAGMPMPGSSY QGTWSEWSDP VIFQTQSEEL KEGWNPHLLL

241 LLLLVIVFIP AFWSLKTHPL WRLWKKIWAV PSPERFFMPL YKGCSGDFKK WVGAPFTGSS

301 LELGPWSPEV PSTLEVYSCH PPRSPAKRLQ LTELQEPAEL VESDGVPKPS FWPTAQNSGG

361 SAYSEERDRP YGLVSIDTVT VLDAEGPCTW PCSCEDDGYP ALDLDAGLEP SPGLEDPLLD

421 AGTTVLSCGC VSAGSPGLGG PLGSLLDRLK PPLADGEDWA GGLPWGGRSP GGVSESEAGS

481 PLAGLDMDTF DSGFVGSDCS SPVECDFTSP GDEGPPRSYL RQWVVIPPPL SSPGPQAS
```

Preferably, in these embodiments the IL21R-derived domain comprises amino acids 254-538 of SEQ ID NO:36. An exemplary nucleic acid sequences encoding IL21R is available in GenBank at Acc. No. NM_021798.3.

IL2-IL2Rβ-CD28 (CIRB28) in NK Cells

NK cells (and others) are activated when MHC-1 molecule expression is down regulated in transformed cells (Algarra et al., Hum Immunol 2000; 61(1):65-73) and during viral infection (Tortorella et al., Annu Rev Immunol 2000; 18:861-92). However, the acquisition of resistance phenotype by tumor cells is often caused by the expression of inhibitory signals from MHC-1 (Kochan et al., Oncoimmunology 2013; 2(11):e26491). HLA-G in particular is known to inhibit NK92 mediated tumor cell lysis (Lin et al., Ann Oncol 2007; 18(11):1804-9). One potential solution to this problem could be the use of multiple activating signals to offset these inhibitory signals. Among the most effective co-stimulatory molecules used for T-cells are CD28 and 4-1BB. CD28 activation requires CD80 and CD86 stimulatory ligand expression on tumor cells. As a result, CD80 expression in tumors was shown to lead to their rejection (Townsend et al., Science 1993; 259(5093):368-70), conversely, in CD28$^{-/-}$ mice, cellular and T cell-dependent immunity are quite deficient (Shahinian et al., Science 1993; 261(5121):609-12). Therefore, low levels of CD80 are considered an escape mechanism for tumors in several cancers (Tirapu et al., Cancer Res 2006; 66(4):2442-50; Hersey et al., Int J Cancer 1994; 58(4):527-32; Bemsen et al., Br J Cancer 2003; 88(3):424-31). For example, the use of a CD28 activation domain in an anti erbB2 chimeric receptor allowed the inhibition of tumor progression in vivo of a MHC-1$^+$ lymphoma Pegram et al., J Immunol 2008; 181(5):3449-55). Although CD28 is expressed by NK92 cells (Gong et al., Leukemia 1994; 8(4):652-8), its activation is not mediated by all cancers.

In some embodiments, the present constructs include the activation domain of CD28 at the C-terminus of the IL2Rβ portion (optionally with an intervening linker therebetween). Sequences for CD28 are also known in the art; an exemplary human CD28 precursor sequence is shown in SEQ ID NO:38.

```
                                                       (SEQ ID NO: 38)
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

Preferably, in these embodiments the CD28-derived domain comprises the intracellular domain, e.g., amino acids 180 to 220 of SEQ ID NO:38, i.e., RSKRSRLLHSDYMNMT-PRRPGPTRKHYQPYAPPRDFAAYRS (SEQ ID NO:39). An exemplary nucleic acid sequence encoding CD28 is available in GenBank at Acc. No. NM_006139.3.

IL2-IL2Rβ-CD28 (CIRB28) in Regulatory T cells (T-regs)

Patients with hematological malignancies greatly benefit from allogeneic hematopoietic stem cell transplant (AHSCT). In this strategy the donor immune system will attack the patient tumor cells with curative potential in a phenomena known as graft versus tumor. Unfortunately, the donor immune cells may also attack the recipient patient healthy tissue either immediately or in the 100 days that follows and cause GVHD. This could lead to death in 15% and/or morbidity in 40 to 60% of AHSCT. Immuno-suppression is currently the standard of care to manage GVHD (Luznik and Fuchs, Immunol Res 2010; 47(1-3):65-77; Storb et al., Biol Blood Marrow Transplant 2010; 16(1 Suppl):S18-27). However, T-regs cells expressing the transcription factor Forkhead box P3 (FOXP3) (Roncador et al., Eur J Immunol 2005; 35(6):1681-91; Hall et al., J Exp Med 1990; 171(1): 141-57) have been found to suppress or alleviate GVHD during AHSCT (Beres et al., J Immunol 2012; 189(1):464-74; Brunstein et al., Blood 2011; 117(3):1061-70). The persistence of FOXP3 expression is maintained by the epigenetic demethylation of 11 CpG motifs in the conserved non-coding sequence 2 (CNS2), located in its first intron. This demethylation pattern lasts for the life span of T-regs and is protected by Ten-Eleven-Translocation DNA dioxygenase, which is recruited to CNS2 by STAT5 activated by IL2 signaling (Nair et al., Mol Cells 2016; 39(12):888-97), to protect the CpG motifs in CNS2 from re-methylation by DNA methyltransferases. Similarly, CTLA-4, an important down regulator of T-cell activation is up regulated in T-regs and is also controlled by IL2 (Wang et al., Scand J Immunol 2001; 54(5):453-8; Bell et al., J Autoimmun 2015; 56:66-80; Gasteiger et al., Front Immunol 2012; 3:179). T-regs are extremely responsive to IL2, due to their massive CD25 expression (Dieckmann et al., Exp Med 2001; 193(11): 1303-10) and their ability to reach IL2 sources by chemokine receptor CCR7 (Smigiel et al., J Exp Med 2014; 211(1):121-36). However, activated T-regs have been shown to lower CD25 expression and change their IL2 signaling in favor of ICOS signaling pathway. This leads to instability of FOXP3 expression making the transition possible from an activated and not terminally differentiated T-regs (Sharma et al., Immunity 2010; 33(6):942-54) to a pro-inflammatory T-cell effector or develop into IFN-gamma-producing proinflammatory Th1 effector cells (Zhang et al., J Immunol 2017; 198(7):2612-25; Feng et al., Gastroenterology 2011; 140(7):2031-43; Takahashi et al., J Exp Med 2011; 208(10): 2055-67) or even Th17 (46). In short, T-regs long-term activation and demethylation of CNS2 as well as proliferation require both IL2 and CD28 co-stimulations (Tang and Bluestone, Immunol Rev 2006; 212:217-37; Chen et al., J Immunol 2011; 186(11):6329-37).

Figure 18:
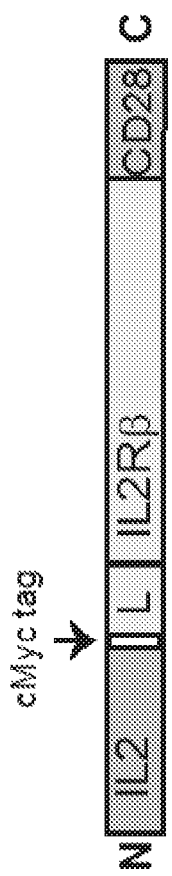
FIG. 18. Exemplary schematic of an IL2-IL2Rβ-CD28 chimera (CIRB28).

Thus the IL2-IL2Rβ-CD28 chimeras described herein could have a dual use: to help NK92 cells override inhibitory signals from MHC-1+ cancer cells, and separately, to activate T-regs for the purpose of treating GVHD. As described herein, without wishing to be bound by theory, addition of the activation domain of CD28 into a novel chimera, IL2-IL2Rβ-CD28 (FIG. 18), combining co-stimulatory signals from IL2 and CD28 will lead to a superior NK92 activation that could help override tumor escape via MHC-1+. This chimera could also lead to proliferation of T-regs cells with long-term FOXP3 expression. This strategy could bypass the use of artificial antigen presenting cells (aAPC), dendritic cells or anti-CD3 antibody required for T-regs activation and expansion.

Nucleic Acids and Expression Vectors

The compositions described herein can include nucleic acid molecules encoding a chimera as described herein.

Nucleic acid molecules comprising expression vectors can be used for expression of the chimeras, e.g., in an NK or T-reg cell as described herein.

A nucleic acid encoding the selected chimera can be inserted in an expression vector, to make an expression construct. A number of suitable vectors are known in the art, e.g., viral vectors including recombinant retroviruses, adenovirus, adeno-associated virus, lentivirus, herpes simplex virus-1, adenovirus-derived vectors, or recombinant bacterial or eukaryotic plasmids. For example, the expression construct can include a coding region for the chimera and one or more regulatory regions, e.g., a promoter sequence, e.g., a promoter sequence that restricts expression to a selected cell type, a conditional promoter, or a strong general promoter; an enhancer sequence; untranslated regulatory sequences, e.g., a 5' untranslated region (UTR), a 3'UTR; a polyadenylation site; and/or an insulator sequence, that direct expression of the chimera. Such sequences are known in the art, and the skilled artisan would be able to select suitable sequences. See, e.g., *Current Protocols in Molecular Biology*, Ausubel, F. M. et al. (eds.) John Wiley & Sons (1995), and Green and Sambrook, *Molecular Cloning: A Laboratory Manual* (Fourth Edition), Cold Spring Harbor Laboratory Press (Jun. 15, 2012) and supplements thereof, and other standard laboratory manuals.

Expression constructs can be administered in any biologically effective carrier, e.g. any formulation or composition capable of effectively delivering the component gene to cells in vivo. Viral vectors transfect cells directly; plasmid DNA can be delivered with the help of, for example, cationic liposomes (e.g., Lipofectin) or derivatized (e.g. antibody conjugated), polylysine conjugates, gramicidin S, artificial viral envelopes or other such intracellular carriers, as well as direct injection of the gene construct or $CaPO_4$ precipitation. In some embodiments, the nucleic acid is applied "naked" to a cell, i.e., is applied in a simple buffer without the use of any additional agents to enhance uptake. See, e.g., Current Protocols in Molecular Biology, Ausubel, F. M. et al. (eds.) Greene Publishing Associates, (1989), Sections 9.10-9.14 and other standard laboratory manuals.

NK and T-Reg Cells

The present methods include expressing, either stably or transiently, a chimera described herein in an NK cell, e.g., a CD3-CD56+ lymphocyte; see Cheng et al., Cellular & Molecular Immunology (2013) 10, 230-252. The NK cell can be a primary cell, e.g., derived from the peripheral blood of a subject and proliferated ex vivo, or can be a cultured NK cell.

When primary cells are used, allogeneic NK cells are preferred, as they were not exposed to immunosuppression and should be fully active. In preferred embodiments, the cells are obtained by performing apheresis on haploidentical related donors to collect peripheral blood leukocytes, which are then depleted of CD3+ cells before optional expansion and administration. See, e.g., Davis et al., Cancer J. 2015 November-December; 21(6): 486-491. Alternatively, the cells can be obtained from peripheral or cord blood cells, stem cells or even induced pluripotent stem cells (iPSCs); see Cheng et al., Cellular & Molecular Immunology (2013) 10, 230-252.

Cultured NK cell lines are known in the art, e.g., including NK-92, KHYG-1, NKL, NKG, NK-YS, YT, YTS and haNK-1 cells, as are methods of making new NK cell lines. NK-92 is a cytolytic cancer cell line that was immortalized ex vivo from NK cells from the blood of a subject suffering from a non-Hodgkins lymphoma. NK-92 cells retain most of the activating receptors and cytolytic signaling pathways but lack the major inhibitory receptors displayed by normal NK cells, and do not express the Fc receptor CD16, and so cannot mediate antibody-dependent cellular cytotoxicity (ADCC). NK-92 cells are tumor-selective and non-immunogenic in humans. The NK-92 cell line is described in Gong et al., Leukemia. 8:652-8 (1994); Yan et al., Clin Cancer Res. 4:2859-68 (1998); WO1998/49268 and U.S. 2002/0068044. NK-92 cells have been evaluated for potential therapeutic use in cancers, including hematological malignancies; see, e.g., Ljunggren and Malmberg, Nat Rev Immunol. 2007 May; 7(5):329-39; Tonn et al., J Hemather Stem Cell Res. 2001 August; 10(4):535-44; Klingemann, Cytotherapy. 2005; 7(1):16-22; Malmberg et al., Cancer Immunol Immunother. 2008 October; 57(10):1541-52. haNK is an NK-92 variant cell line that expresses the high-affinity Fc receptor FcγRIIIa (158V), and is in clinical development to be combined with IgG1 monoclonal antibodies (mAbs). taNKs are targeted NK-92 cells that have been transfected with a gene that expresses a chimeric antigen receptor for a given tumor antigen. KHYG-1 cells were developed the blood of a patient with aggressive NK leukemia (Yagita et al., Leukemia (2000) 14, 922-930) that is IL-2 dependent and produces granzyme M. NKL cells were established from the peripheral blood of a patient with CD3-CD16+CD56+ large granular lymphocyte (LGL) leukemia (Robertson et al., Exp Hematol. 1996 February; 24(3):406-15). NKG cells were established from the peripheral blood of a patient with rapidly progressive non-Hodgkin's lymphoma (Cheng et al., Cell Transplant. 2011; 20(11-12):1731-46). NK-YS cells were established from a patient with a leukemic-state nasal angiocentric natural killer (NK) cell lymphoma with systemic skin infiltration (Tsuchiyama et al., Blood. 1998 Aug. 15; 92(4):1374-83). YT cells, a human NK-like leukaemia cell line, was established from cells in the pericardial fluid of a patient with acute lymphoblastic lymphoma (ALL) and thymoma (Yodoi et al., J Immunol 134: 1623-1630 (1985)); Hamack et al., Anticancer Research 31(2):475-479 (2011)). YTS is a sub-clone of the NK cell leukemia line YT. All of these cell lines are commercially available. For additional information on NK cell lines, Klingermann et al., Front. Immunol. 7:91 (2016); Dahlberg et al., Front. Immunol. 6:605 (2015). The cells can be used as is, or modified, e.g., genetically modified as described in U.S. Pat. Nos. 7,618,817; 8,034,332 (NK-92 cells secreting cytokines including IL2); U.S. Pat. No. 8,313,943 (NK-92 cells expressing CD16); WO 2015193411 (CAR-expressing nk-92 cells); and WO2016160602 (NK-92 cells expressing FcR including CD16). Additional methods for generating and manufacturing cultured NK cells are known in the art; see, e.g., Chabannon et al., Front Immunol. 2016; 7: 504, which provides exemplary parameters for media, cytokines, and culture systems, inter alia.

The present methods also include expressing, either stably or transiently, a chimera described herein (e.g., IL2-IL2Rβ-CD28 chimera) in a T-reg cell, i.e., a CD4+/CD25+ T cell. The T-reg cell can be a primary cell, e.g., derived from the peripheral blood of a subject and proliferated ex vivo, or can be a cultured T-reg cell.

When primary T-reg cells are used, ex-vivo expanded donor T-reg cells, e.g., naturally occurring regulatory T cells (nT-regs) from peripheral blood, are preferred. In preferred embodiments, the cells are obtained from peripheral blood from a donor and expanded ex-vivo using methods known in the art; see, e.g., Dieckmann et al., J. Exp. Med. 193(11): 1303-1310 (2001) Chakraborty et al., Haematologica 98(4): 533-537 (2013); Hippen et al., Sci Transl Med. 2011 May 18; 3(83): 83ra41; and Taylor et al., Blood. 2002; 99:3493-3499. Alternatively, the cells can be obtained from umbilical cord blood (see, e.g., Brunstein et al., Blood. 2011 Jan. 20; 117(3): 1061-1070).

The NK and T-reg cells should be maintained according to good manufacturing practice (GMP) in GMP facilities.

In some embodiments, the NK or T-reg cells are engineered to include a suicide gene, e.g., that allows for the cells expressing the gene to be killed by introduction of a specific and selective agent, as a safety measure to guard against tumorigenesis. A number of suicide gene systems are known in the art, including the cytosine deaminase gene, the varicella-zoster virus thymidine kinase gene, the nitroreductase gene, the *Escherichia coli* gpt gene, the *E. coli* Deo gene (see, e.g., Yazawa et al., World J. Surg. 2002 July; 26(7):783-9), inducible caspase 9 (iCas9) (Di Stasi, N Engl J Med 365: 1673-1683 (2011) and Morgan, Molecular Therapy (2012); 20: 11-13), cytochrome P450, or the herpes simplex virus thymidine kinase (TK) gene, which can be wild-type or mutant TK gene (e.g., tk30, tk75, sr39tk). Cells expressing the TK protein can be killed using ganciclovir. See, e.g., WO 2016160602.

The NK or T-reg cells expressing a chimera as described herein, as well as any supplemental active agents for coadministration, can be incorporated into pharmaceutical compositions. Such compositions typically comprise the cells and a pharmaceutically acceptable carrier. A "pharmaceutically acceptable carrier" includes any and all solvents, antibacterial and antifungal agents, isotonic agents, and the like, compatible with pharmaceutical administration (Gennaro, 2000). Preferred examples of such carriers or diluents include, but are not limited to, water, saline, Ringer's solutions, dextrose solution, and 5% human serum albumin. Liposomes and non-aqueous vehicles such as fixed oils may also be used. Supplementary active compounds can also be incorporated into the compositions.

Sterile injectable solutions can be prepared by incorporating the active compound (e.g., NK or T-reg cells as described herein) in the required amount in an appropriate solvent with one or a combination of ingredients as required; preferably the solvent is already sterilized, or the formulation can be followed by sterilization. In some embodiments, the cells are cryopreserved.

Cancer Immunotherapy

The methods described herein include methods for the treatment of disorders associated with abnormal apoptotic or differentiative processes, e.g., cellular proliferative disorders or cellular differentiative disorders, e.g., cancer, including both solid tumors and hematopoietic cancers. In some embodiments, the disorder is a solid tumor, e.g., breast, prostate, pancreatic, brain, hepatic, lung, kidney, skin, or colon cancer. Generally, the methods include administering a therapeutically effective amount of NK cells expressing a chimera as described herein, to a subject who is in need of, or who has been determined to be in need of, such treatment.

As used in this context, to "treat" means to ameliorate at least one symptom of the disorder associated with abnormal apoptotic or differentiative processes. For example, a treatment can result in a reduction in tumor size or growth rate.

Administration of a therapeutically effective amount of a compound described herein for the treatment of a condition associated with abnormal apoptotic or differentiative processes will result in a reduction in tumor size or decreased growth rate, a reduction in risk or frequency of reoccurrence, a delay in reoccurrence, a reduction in metastasis, increased survival, and/or decreased morbidity and mortality, inter alia.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol. Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

GVHD and Autoimmune Disease

The methods described herein include methods the treatment of disorders associated with abnormal immune response, e.g., graft-versus-host disease or GVHD or autoimmune disease. The methods can include administering T-regulatory cells expressing a IL2-IL2Rβ-CD28 chimera as described herein to a subject who is in need thereof.

Allogeneic bone marrow transplantation (BMT) has been shown to be effective in hematologic malignancies and some solid tumors, but the high incidence of GVHD has limited the effectiveness and use of BMT. T-regs cells have shown efficacy in suppressing GVHD; see Olson et al., Blood. 2010 May 27; 115(21):4293-301; Sung and Chao, STEM CELLS TRANSLATIONAL MEDICINE, 2013; 2:25-32; Dieckmann et al., J. Exp. Med. 193(11):1303-1310 (2001) Chakraborty et al., Haematologica 98(4):533-537 (2013); Hippen et al., Sci Transl Med. 2011 May 18; 3(83): 83ra41; Taylor et al., Blood. 2002; 99:3493-3499; and Brunstein et al., Blood. 2011; 117(3): 1061-1070).

Impairment of T-regs functions or resistance of effector T cells to T-regs has been reported in many autoimmune diseases such as type-1 diabetes (T1D) (Brusko et al., Diabetes 2005; 54(5):1407-14), rheumatoid arthritis (van Amelsfort et al., Arthritis Rheum 2004; 50(9):2775-85), multiple sclerosis (Fletcher et al., J Immunol 2009; 183(11): 7602-10), systemic lupus erythematosus (Lyssuk et al., Adv Exp Med Biol 2007; 601:113-9) and psoriasis (Sugiyama et al., J Immunol 2005; 174(1):164-73), as well as atopic disease (Singer et al., Front Immunol. 2014; 5: 46). Elevated CD25 expression in T-regs makes them particularly responsive to IL2 and this was exploited for example in the case of T1D, where administration of low dose IL-2 promoted T-regs survival and protects NOD mice against diabetes (Tang et al., Immunity 2008; 28(5):687-9; Grinberg-Bleyer et al., J Exp Med 2010; 207(9):1871-8), and an infusion of T-regs preserved beta-cell function in type 1 diabetes in children (Marek-Trzonkowska et al., Diabetes Care (2012) 35:1817-2010).

T-regs, e.g., CD4+CD25+, e.g., CD4+CD25+CD127− Tregs (e.g., CD4+CD25$^{high}$CD127−ICOS+ for atopy Tregs or CD4+CD25+CD127−CD62L+ for GVHD), which are optionally FOXP3+ as well, expressing the IL2-IL2Rβ-CD28 chimeras can be used to reduce alloreactive T cells that are believed to mediate GVHD and autoimmunity and damage host tissues. In these embodiments, an effective amount of T-regs cells expressing a IL2-IL2Rβ-CD28 chimera as described herein is an amount sufficient to decrease numbers of alloreactive T cells and decrease the self-immune response, e.g., by reduction of donor T cell proliferation and increased T cell apoptosis. See, e.g., Singer et al., Front Immunol. 2014; 5: 46; Riley et al., Immunity. 2009 May; 30(5): 656-665.

Methods of Administration and Dosing

The methods include administration, preferably by intravenous infusion, of a therapeutically effective amount of the NK cells described herein. A therapeutically effective dose can be determined empirically, e.g., based on animal experiments and clinical studies. In some embodiments, the methods include one or more infusions of at least $10^4$ and up to $1\times10^6$, $5\times10^6$, $1\times10^7$, $5\times10^7$, $1\times10^8$, $3\times10^8$, $5\times10^8$, $1\times10^9$, or $5\times10^9$ cells per dose, e.g., between 1 billion and 3 billion cells, or any ranges between any two of the numbers, end points inclusive. The cells can be administered to a subject once or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive. See, e.g., Ljunggren and Malmberg, Nat Rev Immunol. 2007 May; 7(5):329-39; Tonn et al., J Hemather Stem Cell Res. 2001 August; 10(4):535-44; Klingemann, Cytotherapy. 2005; 7(1):16-22; Malmberg et al., Cancer Immunol Immunother. 2008 October; 57(10):1541-52; Cheng et al., Cellular & Molecular Immunology (2013) 10, 230-252.

In preferred embodiments, before being infused into a subject the cells are treated so that they are no longer capable of proliferating, but retain cytotoxic activity. One way of achieving this state is by γ irradiation, e.g., with 500 to 1000 cGy, or with 500, 1000, 2000, or 3000 cGy. Gamma irradiation of NK-92 cells at doses of between about 750 and 1000 Grays, e.g., 750, 800, 850, 900 and 950 Grays, is considered to be sufficient for this purpose. Additional forms of radiation, including, for example, ultraviolet radiation, may be employed. Suitable sources to use for this purpose include, for example, a 137Cs source (Cis-US, Bedford, Mass.; Gammacell 40, Atomic Energy of Canada Ltd., Canada). Alternatively, the cells may include a suicide gene as described above.

In some embodiments, before NK cell infusion, the subjects can be treated with a preparatory chemotherapy regimen, e.g., high cyclophosphamide and fludarabine (Hi-Cy [60 mg/kg×2 days]/Flu [25 mg/m$^2$×5 days]), low cyclophosphamide (750 mg/m$^2$) and methylprednisone (1000 mg/m$^2$) or fludarabine alone (25 mg/m$^2$×5 days), and or with total body irradiation, e.g., a dose of 200-500, e.g., 400 cGy, radiation.

Combination Therapies: Checkpoint Inhibitors and Anti-Tumor Monoclonal mAbs

In some embodiments, the chimera-expressing NK cells described herein are administered as part of a therapeutic regimen that includes administration of one or more checkpoint blocking agents and/or anti-tumor antibodies. The NK cells can be administered concurrently, e.g., substantially simultaneously or sequentially, with the checkpoint blocking agents and/or anti-tumor antibodies, e.g., within 48, 24, 12, 6, 5, 4, 3, 2, or 1 hour, or within 45, 30, 20, or 15 minutes of administration of the checkpoint blocking agents and/or anti-tumor antibodies.

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind antigen. Such fragments can be obtained commercially, or using methods known in the art. For example, F(ab)2 fragments can be generated by treating the antibody with an enzyme such as pepsin, a non-specific endopeptidase that normally produces one F(ab)2 fragment and numerous small peptides of the Fc portion. The resulting F(ab)2 fragment is composed of two disulfide-connected Fab units. The Fc fragment is extensively degraded and can be separated from the F(ab)2 by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, IL). In addition, commercially available services for generating antigen-binding fragments can be used, e.g., Bio Express, West Lebanon, NH.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. The antibody can be coupled to a toxin or imaging agent.

Therapeutic anti-tumor antibodies are also known in the art and include human, humanized and chimeric antibodies that bind to tumor antigens. The antibodies are typically monoclonal and can be, e.g., naked, conjugated, or bispecific. Specific examples include alemtuzumab, rituximab, trastuzumab, ibritumomab, gemtuzumab, brentuximab, ado-transtuzumab, blinatunomab, daratumumab and elotuzumab; abciximab; adalimumab; alefacept; basiliximab; belimumab; bezlotoxumab; canakinumab; certolizumab pegol; cetuximab; daclizumab; denosumab; efalizumab; elotuzumab; golimumab; inflectra; ipilimumab; ixekizumab; natalizumab; nivolumab; obinutuzumab; olaratumab; omalizumab; palivizumab; panitumumab; pembrolizumab; tocilizumab; secukinumab; and ustekinumab. A number of antibodies against cancer-related antigens are known; exemplary antibodies are described in Tables 2-3 (Ross et al., Am J Clin Pathol 119(4):472-485, 2003). The method can be used, e.g., to treat a subject who has a cancer that the anti-tumor antibody has been approved to treat (e.g., NK cells in combination with trastuzumab for a subject who has breast cancer, with berntuximab in a subject who has Hodgkin lymphoma, with daratumumab in a subject who has multiple myeloma, or with elotuzumab in a subject who has multiple myeloma).

Checkpoint blocking agents are known in the art and include antibodies directed to CTLA-4 (e.g., ipilimumab, tremelimumab); PD-1 (e.g., nivolumab, pembrolizumab, BGB-A317); PD-L1 (e.g., atezolizumab, avelumab and durvalumab).

EXAMPLES

The invention is further described in the following examples, which do not limit the scope of the invention described in the claims.

Materials and Methods

The following materials and methods were used in the Examples below.

Reagents—Dexamethasone (Dex), chloroquine and Matrigel (cat #126-2.5) and human glycosylated IL2 were from Sigma-Aldrich Co. Horse serum (HS), DMEM/F12 medium, Lipofectamine 2000 and TRIzol were from Life Technologies. Fetal bovine serum (FBS) was from Atlanta Biologicals. RPMI 1640 was from LONZA. Smartscribe and Blueprint Onestep RT-PCR Takara kit were from Clontech Laboratories; Platinum SYBR Green qPCR was from Invitrogen, PfuUltra DNA polymerase was from Stratagene. Human TGFβ1 was from Antigenix America Inc. IL2 was obtained from MGH-DF/HCC Recombinant Protein Core (Boston, MA). Human IL-4 was from Shenandoah Biotechnology Inc. Anti-HER2 (Trastuzumab), humanized Antibody was from BioVision Inc.

Plasmids—packaging plasmid pVSV was from Clontech Laboratories, pCMV-dR8.2 dvpr was from Addgene (plasmid #8455). Lentiviral vectors CSCW-GFP and CSCW-mCherry were from MGH Vector Core (Boston, MA).

Cells—HEK293T, NK92, NK92-MI U251, PC-3, HepG2, MDA-MB-231, Panc-1, U251, BT474 and U266 cells were from ATCC. U266-GFP-Luc and NK92-mCherry-Luc cells were generated by lentiviral transduction using CSCW-GFP and CSCW-mCherry lentiviral vectors, respectively. Tumor cell lines PC-3, U251, U266, Panc-1, BT474 and MDA-MB-231 were cultured in complete RPMI1640 medium. HEK293T and HepG2 cells were cultured in complete DMEM/F12. NK92 and derived cell lines were cultured in RPMI1640 with 10% heat-inactivated FBS, and 10% heat-inactivated horse serum, supplemented with 0.2 mM I-Inositol, 0.02 mM folic acid, 0.1 mM 2-β mercaptoethanol, 2 mM L-glutamine, add 100 IU/ml IL2. All cell lines and assay cultures were maintained at 37° C. and 5% CO2.

Chimera CIRB construction—IL2 cDNA was amplified from human brain total RNA by RTPCR using Forward primer 5'-TGCAGGATCCACTCACAGTAACCT-CAACTCC-3' (SEQ ID NO:1) and reverse primer 5'-TGCACTCGAGAGTGAAACCATTTTAGAGCC-3' (SEQ ID NO:2) and cloned in BamHI-XhoI in pCDNA4–TO. To build the CIRB chimera we first constructed a chimera from IL2 and the extracellular domain of its receptor IL2Rα, which was amplified by RT-PCR from NK92 total RNA using forward oligo 5'-GGATTACCTTTTGT-CAAAGCATCATCTCAACACTGACT-GAGCAGAAGCTC ATTTCGGAAGAAGACCTT-GAAATGGAGACCAGTCAGTTTCCAGG-3' (SEQ ID NO:3), bridging IL2 C-terminal (12 amino acids before the stop codon), and contains the cMyc Tag, the sequence between amino acids 187-194 of IL2Rα as well as and the non-coding 3' sequence of IL2 plasmid. This primer was used with reverse oligo 5'-CCTGATATGTTTTAAGTGG-GAAGCACTTAATTATCAGATTGT TCTTC-TACTCTTCCTCTGTCTCC-3' (SEQ ID NO:4). The amplified fragment was used, as an oligo to mutagenize IL2 wild type resulting in an IL2-IL2Rα chimera.

To build CIRB final chimera construct, the IL2 receptor alpha chimera was used to amplify IL2 with a C-terminal cMyc tag followed by only the extra cellular domain of IL2Rα then followed by the N-terminal fragment of IL2Rβ using Forward 5'-TGCAGGATCCACTCACAGTAACCT-CAACTCC-3' (SEQ ID NO:5) and reverse 5'-GG-GAAGTGCCATTCACCGCGCAGGAAGTCT-CACTCTCAGGA-3'(SEQ ID NO:6). This later introduces the N-terminal end of IL2Rβ. The product was then re-amplified using the same forward primer and reverse 5'-GGCTCTCGAGTTGTAG AAGCATGTGAACTGG-GAAGTGCC ATTCACCGC-3' (SEQ ID NO:7). An XbaI site in IL2 was first removed by mutagenesis using primers forward 5'-CATCTTCAGTGCCTAGAAGAAGAACTC-3' (SEQ ID NO:8) and reverse 5'-GAGTTCTTCTTCTAGGCACTGAAGATG-3' (SEQ ID NO: 9). IL2Rβ was then amplified using forward 5'-TTCCCAGTTCACATGCTTCTACAAGTCGA CAGC-CAACATCTCCTG-3' (SEQ ID NO:10) and reverse 5'-AGCTTCTAGACTC GAGTTATCACACCAAGT-GAGTTGGGTCCTGACCCTGG-3' (SEQ ID NO:11). Next the fragment IL2-cMyc-IL2Rα was open Xho-XbaI and IL2Rβ was added as SalI-XbaI fragment to form the final chimera CIRB. Both IL2 and CIRB were transferred from pcDNA4-TO using SpeI (blunt end) and XhoI to CSCW-mcherry lentiviral vector digested with BamHI (blunt end) and XhoI. All constructs were sequenced and verified for Lentivirus integrity.

Lentivirus production and transduction—HEK293T cells were transfected using Lipofectamine 2000 with 2.4 µg DNA of pVSV, pCMVdr8.2dvrp and the lentiviral construct CSCW-GFP or CSCW-mCherry vectors expressing either CIRB or IL2 constructs, using the ratios 1:0.4:1, respectively, with 25 uM chloroquine. 6 hours post-transfection media was changed and cells were incubated for 36 hours prior to collecting and filtering lentiviral supernatant through a 0.45 um syringe filter. Viral titers were determined by serial dilutions and counting of mCherry expressing HEK293T cells. NK92 cells were infected by spinoculation at 1800 g for 45 min at an optimal multiplicity of infection (MOI) of 46 lentiviral particles per cell in a 2 ml-Eppendorf tube containing $2\times10^5$ cells. Infected cells were then plated in a 6-well plate supplemented with 100 IU/ml of IL2. Two days later, media was changed but without IL2. NK92 cell lines expressing IL2 ($NK92^{IL2}$) or CIRB ($NK92^{CIRB}$) were then permanently weaned of exogenous IL2.

$NK92^{CIRB}$ growth was compared to $NK92^{IL2}$, parental NK92 and IL2-independent NK92-MI cell line. $60\times10^3$ cells were cultured in 6 well plates for 3 days after which 3 ml fresh media were added on top of old media for another 3 days. Viable cells were counted by Trypan blue exclusion using a Bio-Rad TC20™ automated cell counter. Protein expression was detected by western blot on total cell lysate obtained by sonication.

Flow cytometry—NK cell markers expression was verified using mouse anti-Human antibodies to CD45-APC-CY7, CD25-FITC, CD16-PE, CD3-PECY7, CD56-PAC BLUE and CD122-PE, purchased from BD Biosciences, San Jose, CA. Antibodies to NKG2D-APC were from BioLegend, DAPI from Invitrogen, mouse anti-cMyc: sureLight APC was from Columbia Biosciences. Cells were sorted at MGH Flow Cytometry Core facility using a BD 5 laser SORP FACS Vantage SE Diva system (BD Biosciences) using argon-ion laser excitation (633 nm and 35 mW for excitation). Intact cells were gated using the forward and sideward scatter from 488 nm excitation and 320 mW. Data acquisition was carried out by analyzing $10^5$ events/sample, using CellQuest Software (BD Biosciences). FACS data were analyzed using FlowJo Software (Tree Star, Inc.). Human primary NK cells were extracted from peripheral blood of healthy donors using the Rosetteseprm human enrichment kit (StemCell technologies), following the manufacturer protocol.

Cytotoxic activity of NK92, $NK92^{IL2}$ and $NK92^{CIRB}$ cells—To assess the cytolytic effects of $NK92^{IL2}$ and $NK92^{CIRB}$, compared to the parental NK92 cell line (pre-stimulated for 24 hours with IL2, 100 IU/ml). $8\times10^3$ U266GFP cells (selected for firm adherence), were plated in triplicate in 96 well plates. 24 hours later NK cells lines were added at effector/target cells ratios (E/T) of 1/8, 1/4, 1/2, 1/1 and 2/1. After two days of co-culture NK cells were suspended to allow further killing of U266GFP cells. After a total 4 days co-culture, U266GFP cell survival was evaluated using a SpectraMax® M2 Microplate fluorescence reader (Molecular Devices) with excitation at 485 nm and emission at 515 nm.

Another set of experiments evaluated the anti-cancer effect of NK92, $NK92^{IL2}$ and $NK92^{CIRB}$ on a panel of five cancer cell lines, U251GM, PC-3, Panc-1, MDA-MB-231 and HepG2 cells. $32\times10^3$ cells for each cancer cell line, were first plated in a 24-well plate for either 24 hours prior to adding NK92 (pre-stimulated with IL2, 100 IU/ml), $NK92^{IL2}$ or $NK92^{CIRB}$ at E/T ratio of 2/1 target cancer cell (FIG. 3B), or only 5 hours (FIG. 3C) before adding $NK92^{IL2}$ or $NK92^{CIRB}$ at E/T ratios of 0/1, 1/1, 2/1, and 3/1 for each cancer cell line. Co-cultured cells were then incubated for 4 days. Cell viability of cancer cells after this time was determined using a 0.1% crystal violet in a 10% alcohol solution followed by extraction using 70% ethanol and reading absorbance at 595 nm.

ADCC of $NK92^{IL2}$ and $NK92^{CIRB}$ Against Her2 Positive Breast Cancer Cell Line BT474—

Target Breast cancer BT474 ($8\times10^3$ cells) was plated in 96-well plates. 24 hours later cells were incubated for 20 min at room temperature with 1 ug/ml Trastuzumab before the addition of effector cells at an E/T ratio of 2:1. After 3 days of incubation, viability of cancer cells was determined using crystal violet/alcohol-extraction assay described earlier.

Impact of pre-exposure to immunosuppressors on NK cells cytotoxicity and viability—NK92, $NK92^{IL2}$ and $NK92^{CIRB}$ ($64\times10^3$ cells), were plated and exposed for 24 hours to TGFβ1 (20 ng/ml), Il-4 (20 ng/ml), or Dex (0.5 uM). During this time parental NK92 cells were incubated with IL2 at 201 U/ml. Cancer cells U251GM, PC-3, Panc-1, MDA-MB-231 and HepG2 cells ($32\times10^3$ cells) were then added to NK cells at an E/T ratio of 2:1. Co-cultured cells were then incubated for 4 days. Cell viability of cancer cells after this time was determined using crystal violet/alcohol-extraction assay.

To determine the impact of immunosuppressors TGFβ1, IL-4 and Dex on the growth of $NK92^{IL2}$ and $NK92^{CIRB}$ ($30\times10^3$ cells), were plated in triplicate in a 12-well plate, grown under TGFβ1 (10 ng/ml), IL-4 (10 ng/ml), or Dex (1 uM) for 3 days, then refreshed for another 3 days of growth under the same conditions for a total of six days. After that time cells viability was determined with Trypan blue.

Tumor Growth Delay Experiments—5 week-old (24-25 g) male NOD.Cg-Prkdcscid Il2rgtm1Wjl/SzJ immunodeficient mice were purchased from Jackson Laboratory and were housed in the MGH center for comparative medicine. These animals are devoid of B and T cells as well as NK cells, thus offer a suitable platform to evaluate the therapeutic efficacy of modified NK cells. U251 or PC-3 cells were suspended in serum-free RPMI containing 20% Matrigel and injected sub-cutaneously (s.c.) as $4\times10^6$ cells for PC-3 or $3\times10^6$ cells for U251 in a volume of 0.5 ml using a 0.5-inch 29-gauge needle and a 1 ml insulin syringe. Tumor areas (length×width) were measured twice a week using Vernier calipers (Manostat Corp., Switzerland) and tumor volumes were calculated based on: Volume=$\pi/6$ (length× width)$^{3/2}$. Treatment with $NK92^{CIRB}$ or $NK92^{IL2}$ was initiated when the average tumor volume reached ~200 mm$^3$ for PC-3 or ~160 mm$^3$ for U251. For animals bearing PC-3 tumors freshly prepared NK cells were suspended in PBS irradiated with 500 cGy and administered as 4 weekly injections ($15\times10^6$ cells in 200 ul per mouse), via the tail vein. For animals bearing U251 cells $NK92^{CIRB}$ or $NK92^{IL2}$ were not irradiated. Detection of $NK92^{CIRB}$ and $NK92^{IL2}$ in peripheral blood—U251MG tumor cells were grown s.c. in Nod/scid mice. When tumor size reached ~ 160 mm$^3$, non-irradiated $NK92^{IL2}$ and $NK92^{CIRB}$ cells ($10^7$ cells in 200 ul per mouse), were injected, via the tail vein. A second injection of non-irradiated NK cells ($5\times10^6$ cells) was carried out 4 days later. 17 days later, animals were killed and cardiac blood was collected from 3 animals in each group. Heparinized blood was processed and analyzed by flow cytometry using human specific anti-CD45 and mCherry fluorescent protein, which is exclusively co-expressed with IL2 or CIRB via an internal ribosome entry site.

Survival of irradiated NK92CIRB and NK92$^{IL2}$ cells— After irradiation at 10 Gy (0.83 Gy for 12 min), NK92CIRB and NK92$^{IL2}$ were then cultured and their survival was determined, using Trypan Blue every 24 hours for 3 days.

Expression profiles of cytotoxicity effectors in NK92, NK92$^{IL2}$ and NK92$^{CIRB}$—Expression profiles of natural cytotoxicity receptors NKP30, NKP44, NKP46, cytolytic enzymes Perforin-1 and Granzyme-B, and cytokines TNFα and IFN-γ were quantified by qRT-PCR using the primers listed in Table 1. Results were analyzed using comparative $C_T$ ($\Delta\Delta C_T$) method and are presented as RNA folds relative to NK92 parental cell line after normalization to the GAPDH RNA content of each sample

TABLE 1

Primers used for Expression profiles of cytotoxicity effectors in NK92, NK92$^{IL2}$ and NK92$^{CIRB}$

| Gene name | Forward primer sequence 5' to 3' | SEQ ID NO: | Reverse primer sequence 5' to 3' | SEQ ID NO: | Size bp |
|---|---|---|---|---|---|
| NKp30 | GCTGGTGGTGGAGAAAGAAC | 12 | GGACCTTTCCAGGTCAGACA | 13 | 144 |
| NKp44 | TCACAGCCACAGAACTCCAC | 14 | CCTGAGCTCCATCATGGTTT | 15 | 262 |
| NKp46 | TGCCGTCTAGACACTGCAAC | 16 | CCAAAACATCGGTATGTCCC | 17 | 146 |
| Perforin-1 | CGCCTACCTCAGGCTTATCTC | 18 | CCTCGACAGTCAGGCAGTC | 19 | 155 |
| Granzyme-B | CCCTGGGAAAACACTCACACA | 20 | CACAACTCAATGGTACTGTCGT | 21 | 108 |
| TNFalpha | CCCAGGGACCTCTCTCTAATCA | 22 | AGCTGCCCCTCAGCTTGAG | 23 | 115 |
| INFgamma | TCGGTAACTGACTTGAATGTCCA | 24 | TCCTTTTTCGCTTCCCTGTTTT | 25 | 100 |
| GAPDH | ATGGGGAAGGTGAAGGTCG | 26 | GGGGTCATTGATGGCAACAATA | 27 | 108 |

Statistical Analysis—Statistical significance of differences was determined by two-tailed Student's test, a one-way ANOVA, paired Tukey's Multiple Comparison test. All tests included comparisons to untreated samples or as indicated in the text. Statistical significance is indicated by *P<0.05, P<0.01, *P<0.001, ****P<0.001. Analyses were performed using Prism software version 6 (GraphPad Software).

Example 1. Design and Construction of the CIRB Chimera

The quaternary crystal structure of IL2 and its receptors complex (20) shows that the C-terminal end of IL2 and the N-terminal residue of IL2Rβ are separated by 41 Å. For a linker between IL2 and the N-terminus of IL2Rβ we choose the extracellular domain of IL2Rα (EMETSQFPGEEKPQASPEGRPESETSC (SEQ ID NO:28)). A cMyc tag (EQKLISEEDL (SEQ ID NO:29)) was added between IL2 and the linker. The fully mature receptor IL2Rβ protein coding sequence (without signal peptide) was placed after the linker to yield the full chimera CIRB (FIG. 1). Both CIRB and IL2 were cloned in a lentiviral vector co-expressing mCherry. The linker fold was predicted computationally to be a helix-dominated structure (FIGS. 5A-D). Linker flexibility was assessed using the computational method of Karplus and Shultz method (47) which, indicates better than average flexibility (1 or greater on a 0 to 2 scale) at all the peptide linkages.

The resulting sequences are shown below.

Nucleotide Sequence of IL2-IL2Rβ:
(SEQ ID NO: 30)
ATGTACAGGATGCAACTCCTGTCTTGCATTGCACTAAGTCTTGCACTTG

TCACAAACAGTGCACCTACTTCAAGTTCTACAAAGAAAACACAGCTACA

ACTGGAGCATTTACTGCTGGATTTACAGATGATTTTGAATGGAATTAAT

AATTACAAGAATCCCAAACTCACCAGGATGCTCACATTTAAGTTTTACA

TGCCCAAGAAGGCCACAGAACTGAAACATCTTCAGTGCCTAGAAGAAGA

ACTCAAACCTCTGGAGGAAGTGCTAAATTTAGCTCAAAGCAAAAACTTT

-continued

CACTTAAGACCCAGGGACTTAATCAGCAATATCAACGTAATAGTTCTGG

AACTAAAGGGATCTGAAACAACATTCATGTGTGAATATGCTGATGAGAC

AGCAACCATTGTAGAATTTCTGAACAGATGGATTACCTTTTGTCAAAGC

ATCATCTCAACACTGACTGAGCAGAAGCTCATTTCGGAAGAAACCTTGA

AATGGAGACCAGTCAGTTTCCAGGTGAAGAGAAGCCTCAGGCAAGCCCC

GAAGGCCGTCCTGAGAGTGAGACTTCCTGCGCGGTGAATGGCACTTCCC

AGTTCACATGCTTCTACAACTCGCGAGCCAACATCTCCTGTGTCTGGAG

CCAAGATGGGGCTCTGCAGGACACTTCCTGCCAAGTCCATGCCTGGCCG

GACAGACGGCGGTGGAACCAAACCTGTGAGCTGCTCCCCGTGAGTCAAG

CATCCTGGGCCTGCAACCTGATCCTCGGAGCCCCAGATTCTCAGAAACT

GACCACAGTTGACATCGTCACCCTGAGGGTGCTGTGTCGTGAGGGGGTG

CGATGGAGGGTGATGGCCATCCAGGACTTCAAGCCCTTTGAGAACCTTC

GCCTGATGGCCCCCATCTCCCTCCAAGTTGTCCACGTGGAGACCCACAG

ATGCAACATAAGCTGGGAAATCTCCCAAGCCTCCCACTACTTTGAAAGA

CACCTGGAGTTCGAGGCCCGGACGCTGTCCCCAGGCCACACCTGGGAGG

AGGCCCCCCTGCTGACTCTCAAGCAGAAGCAGGAATGGATCTGCCTGGA

GACGCTCACCCCAGACACCCAGTATGAGTTTCAGGTGCGGGTCAAGCCT

```
-continued
CTGCAAGGCGAGTTCACGACCTGGAGCCCTGGAGCCAGCCCCTGGCCT

TCAGGACAAAGCCTGCAGCCCTTGGGAAGGACACCATTCCGTGGCTCGG

CCACCTCCTCGTGGGTCTCAGCGGGCTTTTGGCTTCATCATCTTAGTG

TACTTGCTGATCAACTGCAGGAACACCGGGCCATGGCTGAAGAAGGTCC

TGAAGTGTAACACCCCAGACCCCTCGAAGTTCTTTTCCCAGCTGAGCTC

AGAGCATGGAGGAGACGTCCAGAAGTGGCTCTCTTCGCCCTTCCCCTCA

TCGTCCTTCAGCCCTGGCGGCCTGGCACCTGAGATCTCGCCACTAGAAG

TGCTGGAGAGGGACAAGGTGACGCAGCTGCTCCTGCAGCAGGACAAGGT

GCCTGAGCCCGCATCCTTAAGCAGCAACCACTCGCTGACCAGCTGCTTC

ACCAACCAGGGTTACTTCTTCTTCCACCTCCCGGATGCCTTGGAGATAG

AGGCCTGCCAGGTGTACTTTACTTACGACCCCTACTCAGAGGAAGACCC

TGATGAGGGTGTGGCCGGGGCACCCACAGGGTCTTCCCCCCAACCCCTG

CAGCCTCTGTCAGGGGAGGACGACGCCTACTGCACCTTCCCCTCCAGGG

ATGACCTGCTGCTCTTCTCCCCCAGTCTCCTCGGTGGCCCCAGCCCCCC

AAGCACTGCCCCTGGGGGCAGTGGGGCCGGTGAAGAGAGGATGCCCCCT

TCTTTGCAAGAAAGAGTCCCCAGAGACTGGGACCCCCAGCCCCTGGGGC

CTCCCACCCCAGGAGTCCCAGACCTGGTGGATTTTCAGCCACCCCCTGA

GCTGGTGCTGCGAGAGGCTGGGGAGGAGGTCCCTGACGCTGGCCCCAGG

GAGGGAGTCAGTTTCCCCTGGTCCAGGCCTCCTGGGCAGGGGGAGTTCA

GGGCCCTTAATGCTCGCCTGCCCCTGAACACTGATGCCTACTTGTCCCT

CCAAGAACTCCAGGGTCAGGACCCAACTCACTTGGTGTGA

Protein Sequence of IL2-IL2Rβ
                                    (SEQ ID NO: 31)
MYRMQLLSCIALSLALVTNSAPTSSSTKKTQLQLEHLLLDLQMILNGIN

NYKNPKLTRMLTFKFYMPKKATELKHLQCLEEELKPLEEVLNLAQSKNF

HLRPRDLISNINVIVLELKGSETTFMCEYADETATIVEFLNRWITFCQS

IISTLTEQKLISEEDLEMETSQFPGEEKPQASPEGRPESETSCAVNGTS

QFTCFYNSRANISCVWSQDGALQDTSCQVHAWPDRRRWNQTCELLPVSQ

ASWACNLILGAPDSQKLTTVDIVTLRVLCREGVRWRVMAIQDFKPFENL

RLMAPISLQVVHVETHRCNISWEISQASHYFERHLEFEARTLSPGHTWE

EAPLLTLKQKQEWICLETLTPDTQYEFQVRVKPLQFEFTTWSPWSQPLA

FRTKPAALGKDTIPWLGHLLVGLSGAFGFIILVYLLINCRNTGPWLKKV

LKCNTPDPSKFFSQLSSEHGGDVQKWLSSPFPSSSFSPGGLAPEISPLE

VLERDKVTQLLLQQDKVPEPASLSSNHSLTSCFTNQGYFFFHLPDALEI

EACQVYFTYDPYSEEDPDEGVAGAPTGSSPQPLQPLSGEDDAYCTFPSR

DDLLLFSPSLLGGPSPPSTAPGGSGAGEERMPPSLQERVPRDWDPQPLG

PPTPGVPDLVDFQPPPELVLREAGEEVPDAGPREGVSFPWSRPPGQGEF

RALNARLPLNTDAYLSLQELQGQDPTHLV*
```

Example 2. Cell Surface Expression of the Chimera CIRB

Figure 2A:
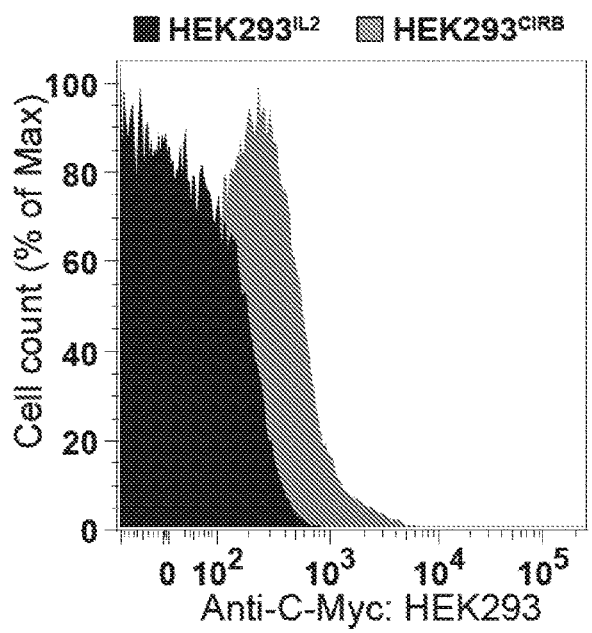
FIGS. 2A-D—Surface detection and expression of chimera CIRB. A, detection by anti-cMyc monoclonal antibody of CIRB expression at the surface of transiently transfected HEK293 cells and B, in lentivirus transduced NK92 cells. C, CD122 expression detected using an anti-CD122 monoclonal antibody, which recognizes the native IL2Rβ (CD122) as well as the chimera. CD122 is present in NK92$^{IL2}$ cells and as expected, much higher in NK92$^{CIRB}$ due to the additional expression of CIRB. Expression was higher than the background detected in the absence of antibody (Neg). D, CIRB was further detected by western blot using monoclonal anti-human IL2.
Figure 2B:
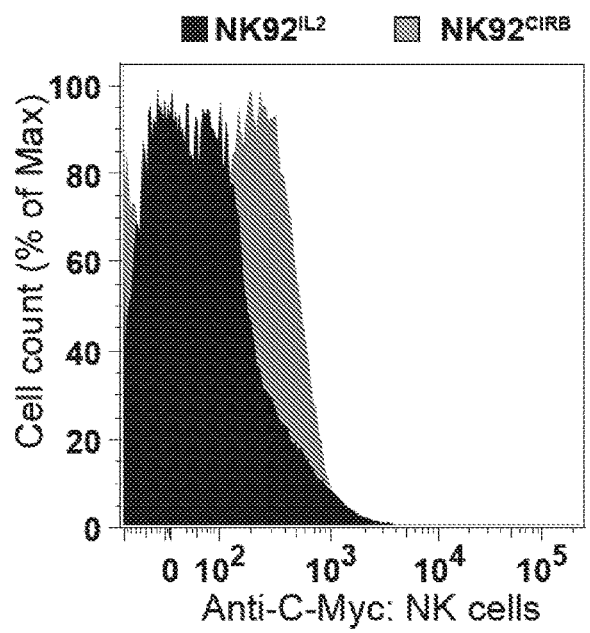
Figure 2C:
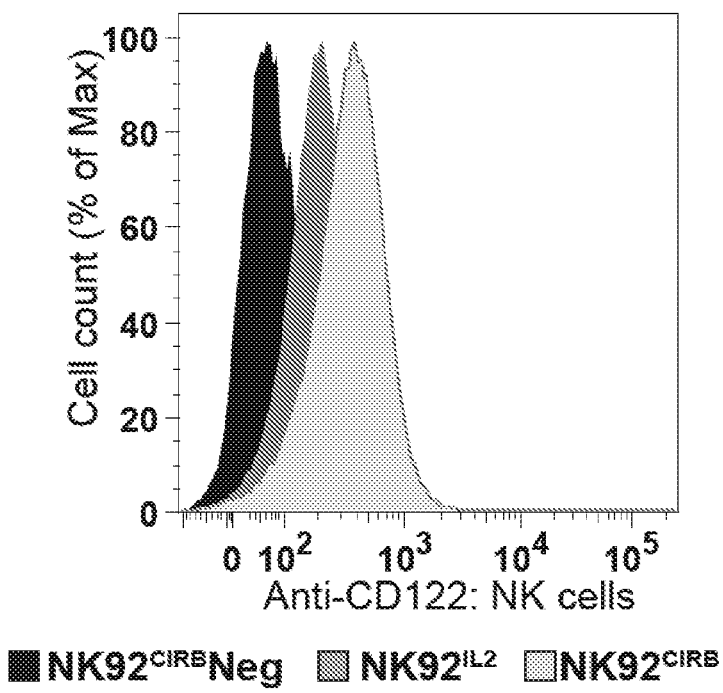
Figure 2D:

After Lentivirus-mediated stable expression with an identical MOI of 46, NK92$^{IL2}$ and NK92$^{CIRB}$ cell lines acquire IL2 independence and proliferate indefinitely. Both cell lines showed similar growth during a 6-days period and faster than NK92-MI another IL2-independent cell line (FIGS. 6A-B), with robust survival after subjection to multiple freezing and plating cycles in culture, comparatively to the parental NK92 cell line and NK92-MI. Using an anti-cMyc monoclonal antibody, we next examined the expression of CIRB at the cell surface of transiently transfected HEK293 cells (FIG. 2A) and stable NK92$^{CIRB}$ cells (FIG. 2B). We found clear evidence of the surface expression of cMyc in NK92$^{CIRB}$ but not in NK92$^{IL2}$ cells. CIRB expression was further confirmed using an anti-CD122 monoclonal antibody, which recognizes the native IL2Rβ as well as the chimera shows that the endogenous CD122 is present in NK92$^{IL2}$ cells, as expected, but at levels lower than in NK92$^{CIRB}$ cell line, which express both IL2Rβ and CIRB. The expression of the full-length chimera CIRB was further detected by western blot using monoclonal anti-human IL2. FIG. 2D shows a full-length size of 95 kDa, which is higher than the predicted size of 80 kDa and could be due to post-translational glycosylation.

Example 3. Cytotoxicity of Parental NK-92 and Modified Cell Lines

Figure 3A:
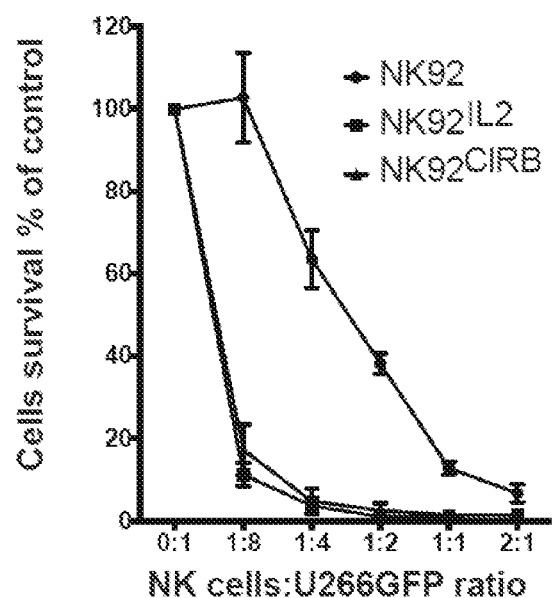
FIGS. 3A-C—A, cytotoxicity assays of NK92$^{IL2}$, NK92$^{CIRB}$, and parental NK92 cell lines against multiple myeloma U266GFP cells plated 24 hours prior to co-culture. Increased E/T ratios of NK cells induced more U266GFP cell death as quantified by GFP-emitted fluorescence. B, cytotoxicity assay against a panel of five human cancer cell lines: Cells were plated 24 hours prior to adding NK cell lines at E/T ratio of 2:1. While in C, cancer cells were plated only 5 hours prior to exposure to increasing E/T ratios of NK92$^{IL2}$ (●), or NK92$^{CIRB}$ (■) cells. Remaining cells after this time were determined using a crystal violet/alcohol-extraction assay. Data are presented as cell number relative to NK cells-free controls, mean+SE values for triplicate samples.
Figure 3B:
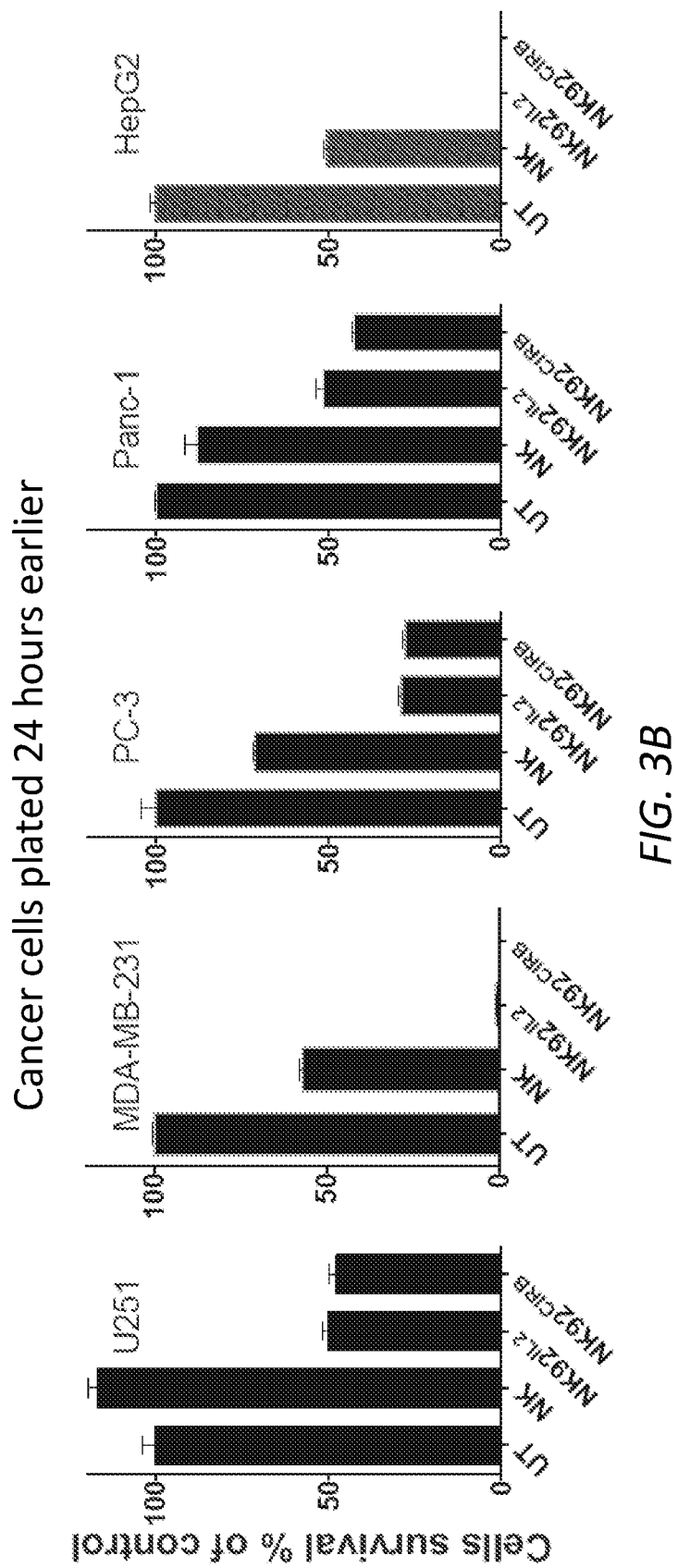
Figure 3C:
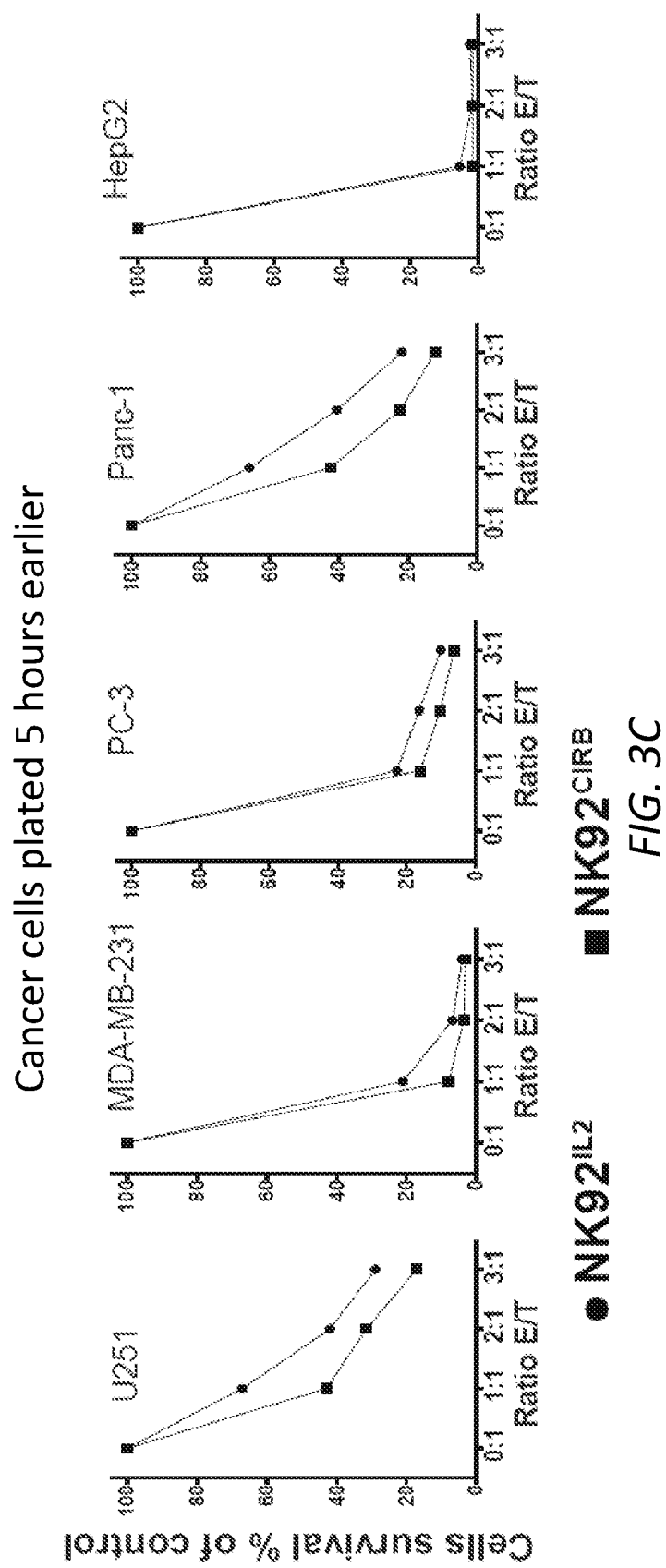

We compared cytotoxicity of NK92, NK92$^{IL2}$ and NK92$^{CIRB}$ cells against an adherent multiple myeloma cell line U266GFP. FIG. 3A shows that the parental NK92 cell line, although pre-stimulated with 100 IU/ml of IL2, was far less cytotoxic than NK92$^{IL2}$ or NK92$^{CIRB}$. Of note, IL2 was absent during the four days of co-culture. NK92$^{IL2}$ and NK92$^{CIRB}$ cells showed equivalent cytotoxicity toward U266GFP suggesting comparable levels of activation in vitro.

We further compared anti-cancer activity of NK92$^{IL2}$ and NK92$^{CIRB}$ cells in a panel of five human cancer cell lines. In one experiment (FIG. 3B) cells were plated 24 hours prior to adding NK cell lines. The cytotoxicity of NK92$^{IL2}$ and NK92$^{CIRB}$ cells were generally equivalent with a slight edge to NK92$^{CIRB}$. NK92 cell were inferior to the other two NK lines. In other experiments, cancer cells were plated only 5 hours prior to adding NK cells (FIG. 3C) the cytotoxicity of NK cell lines became more pronounced than at 24 hours post plating. Under these conditions, the cytotoxicity of all NK cell lines was greater than in cells plated for 24 hours and NK92$^{CIRB}$ showed more cytotoxicity than NK92$^{IL2}$ cells, at most E/T ratios. This difference was more evident with the most resistant cancer cell lines U251GM and Panc-1.

Figure 4A:
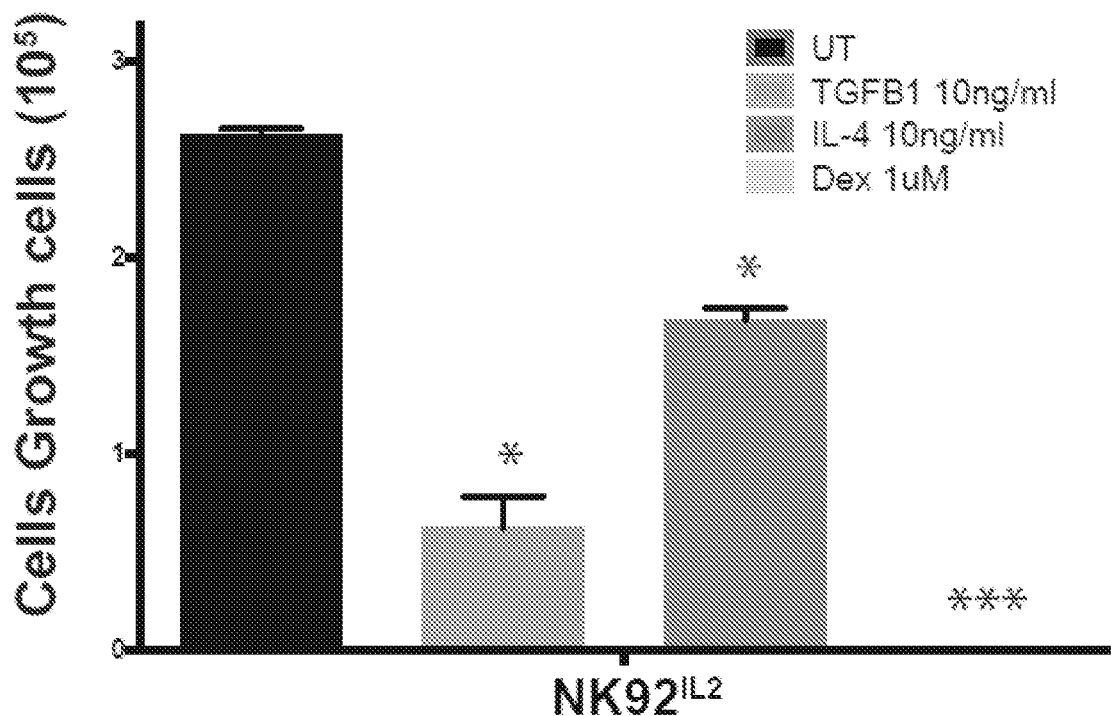
FIGS. 4A-C—impact of TGFβ1, IL-4 and Dexamethasone on NK cells viability. A, 64×10³ NK92$^{IL2}$ and B, NK92$^{CIRB}$ cells were plated with TGFβ1 (10 ng/ml), IL-4 (10 ng/ml), or Dex (1 uM) for 6 days of growth. Viable cells were counted using Trypan blue. Data are presented as final cell number (10⁵ cells/ml), mean+SE values for triplicate samples. C, NK92, NK92$^{IL2}$ and NK92$^{CIRB}$ cell lines exposed for 24 hours to TGFβ1 (20 ng/ml U), Dex (0.5 uM A), or no drug (UT U). Parental NK 92 cells were incubated with IL2 at 201 U/ml. Cancer cells (32×10³ cells), were then added to NK cells at E/T ratio of 2:1, then incubated for 4 days. Cancer cells viability was determined using a crystal violet extraction assay. Data are presented as mean percentage cell number relative to NK cells-free controls (UT).
Figure 4B:
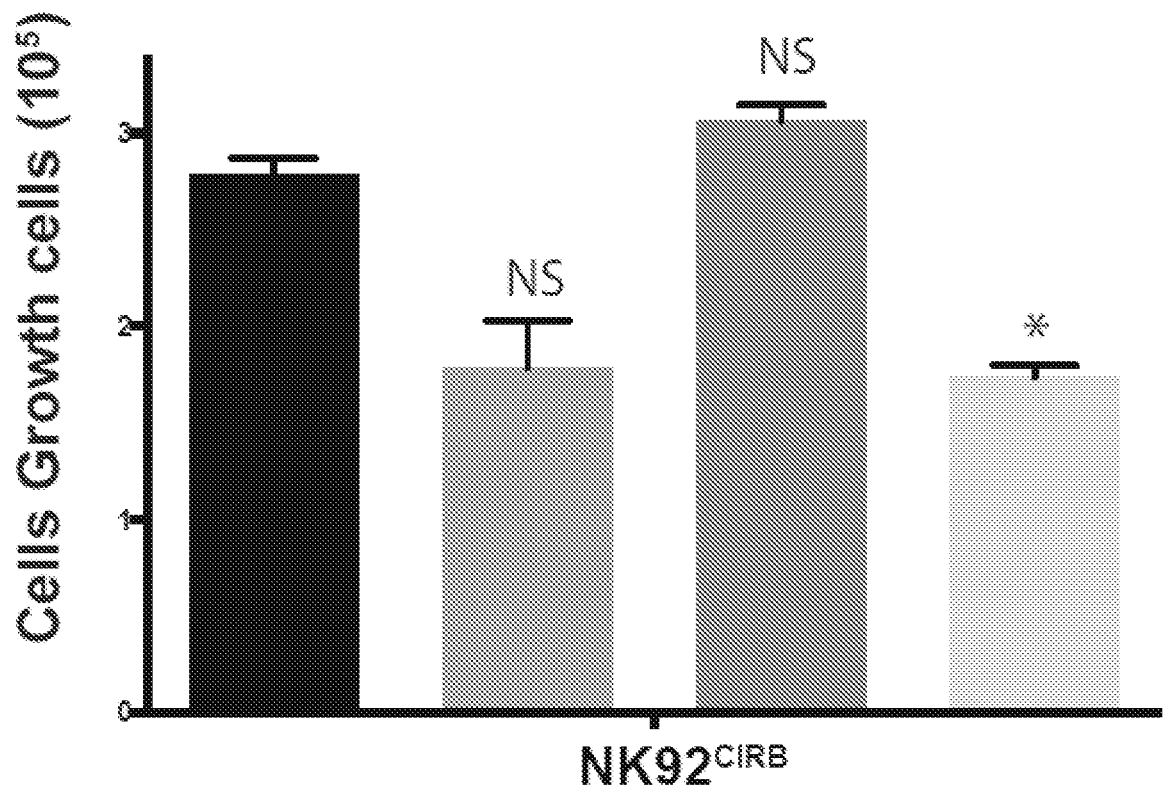

Example 4. NK92$^{CIRB}$ Resistance to TGFβ1, IL4 and Dexamethasone Immunosuppression Transforming growth factor TGFβ1 is an immunosuppressor overexpressed in the TME and is known to inhibit NK cells functions by destabilizing several activation signals in NK cells (34). The glucocorticoid dexamethasone impairs the function of lymphocytes in part by suppressing IL2 production from CD4+ T cells (35). IL-4 was reported to inhibit the proliferation of NK cells (48). We tested the effects of these immunosuppressors in both NK92$^{IL2}$ and NK92$^{CIRB}$ lines by culturing cells for 6 days in the presence of TGFβ1 (10 ng/ml), IL4 (10 ng/ml), or dex (1 uM). FIG. 4A shows that NK92$^{IL2}$ cells did not survive the exposure to dex, and their proliferation was inhibited strongly by TGFβ1 and to some extent by IL4. In contrast, the proliferation of NK92$^{CIRB}$ cells was not significantly affected by TGFβ1 or IL4 and was only weakly inhibited by dex (FIG. 4B).

Figure 4C:
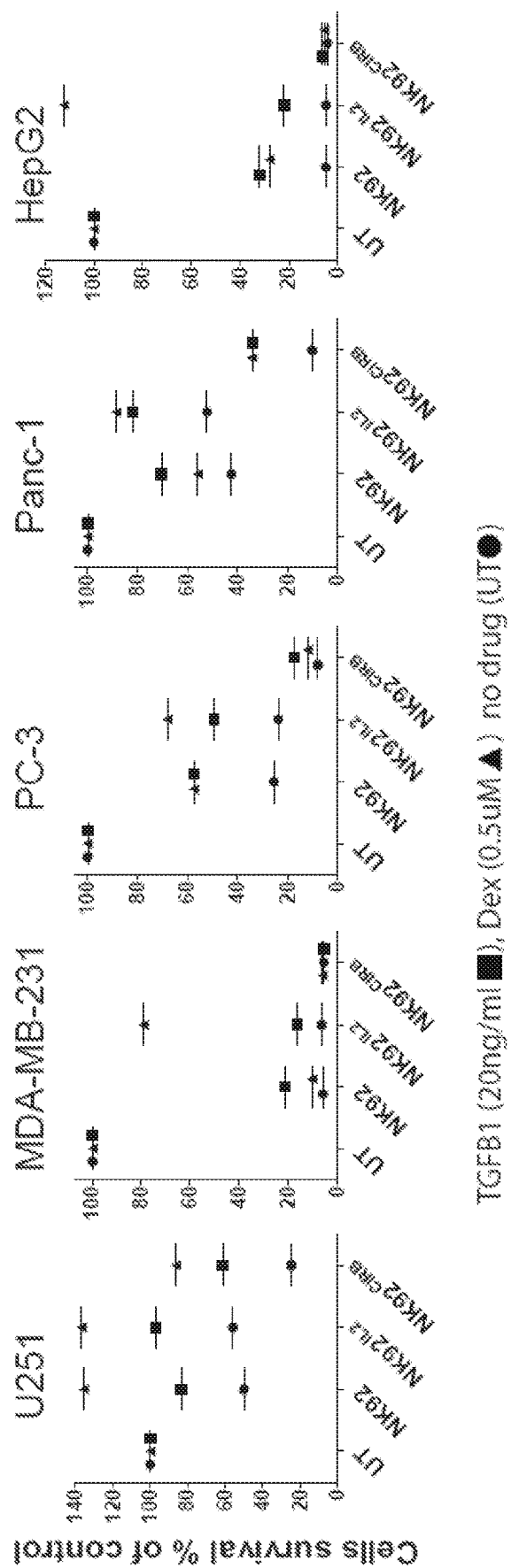

The effects of TGFβ1 and dex pre-treatments on NK cell cytotoxicity were then evaluated using the panel of five cancer cell lines at an E/T ratio of 2:1 (FIG. 4C). NK cells affected more killing in these experimental conditions since cancer cells were added to already plated NK92 cells and are more vulnerable if not already attached. Additionally, the parental NK92 cells were plated with IL2 in the media (201 U/ml) and are therefore more active than in other experiments. NK92$^{CIRB}$ cytotoxicity against MDA-MB-231, PC-3 and HepG2 was not affected. Dex severely reduced cytotoxicity of NK92$^{IL2}$ cells towards all cancer cell lines. Similarly, TGFβ1 significantly reduced NK92$^{IL2}$ cytotoxicity against most cancer cell lines except for MDA-MB-231 and HepG2. Surprisingly, NK92 cells also showed resistance to dex inhibition in MDA-MB-231 and HepG2. Overall immunosuppression of NK92$^{CIRB}$ cells was weaker than in the NK92 and NK92$^{IL2}$ lines and was also dependent on the target cancer cell line.

Figure 5B:
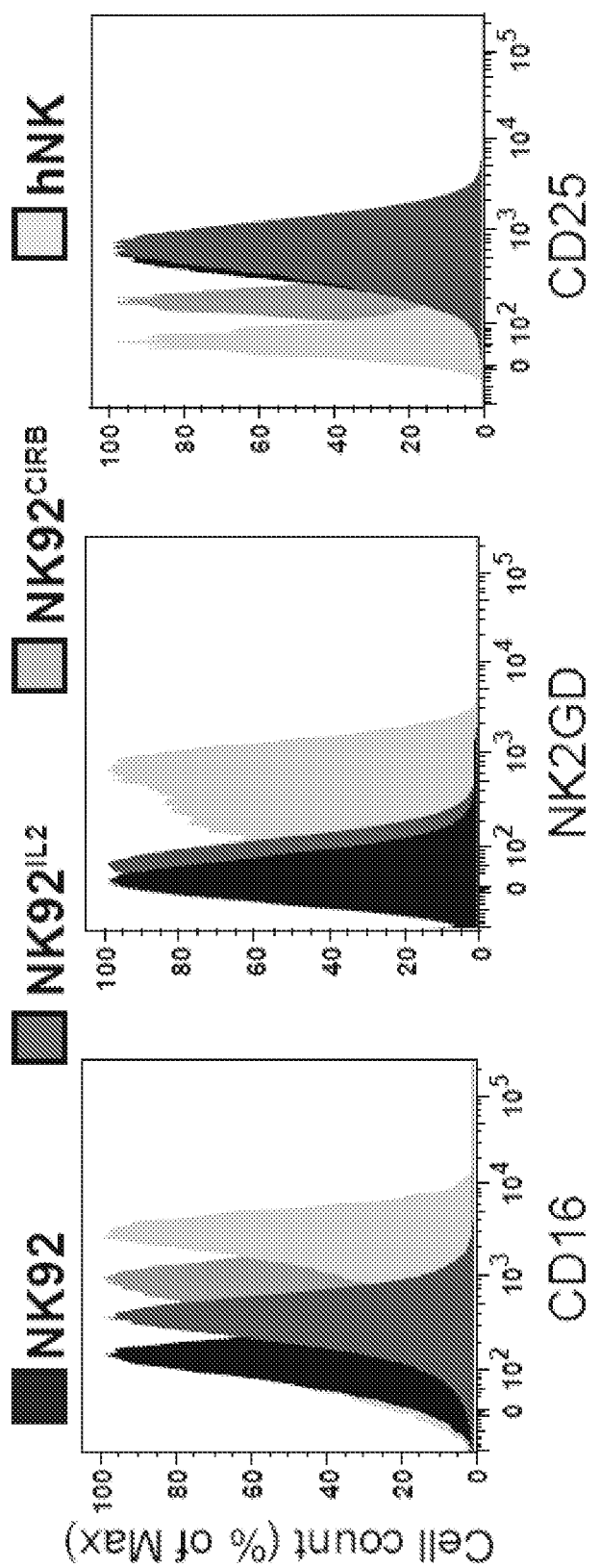
Figure 10A:
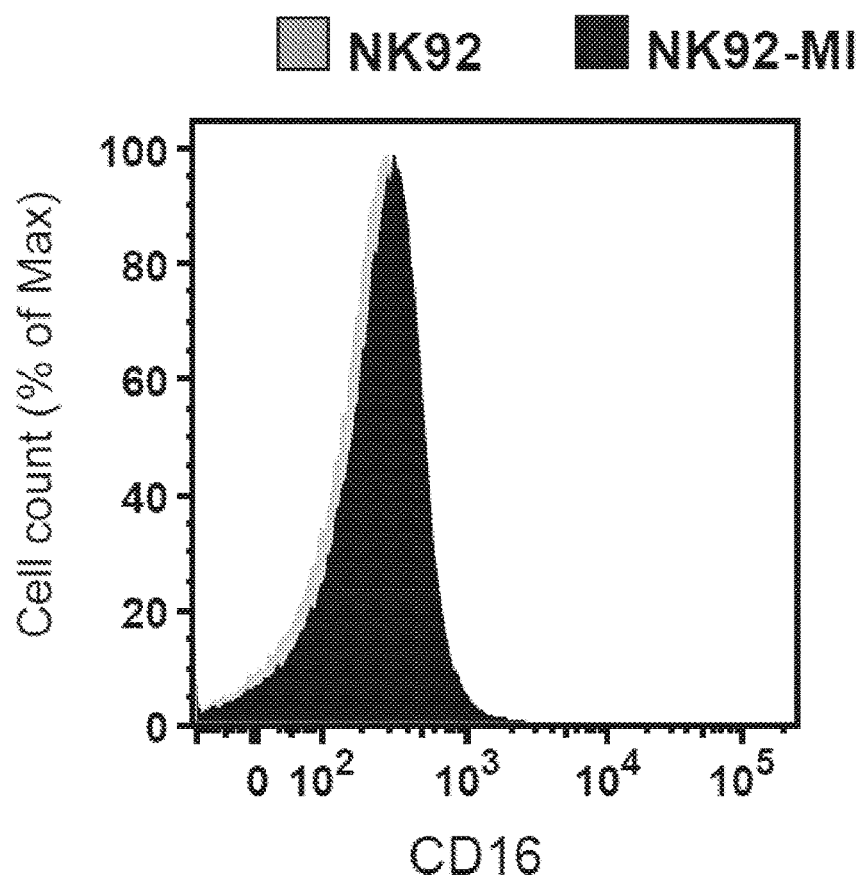
FIGS. 10A-B—Expression of CD 16 in NK92-MI and NK92. A, Flow cytometry confirms the lack of expression of CD16 in NK92 and NK92-MI. B, shows the lack of expression of CD16 in NK92 activated with 100 or 10001 U/m of glycosylated (G) and non-glycosylated IL2.
Figure 10B:
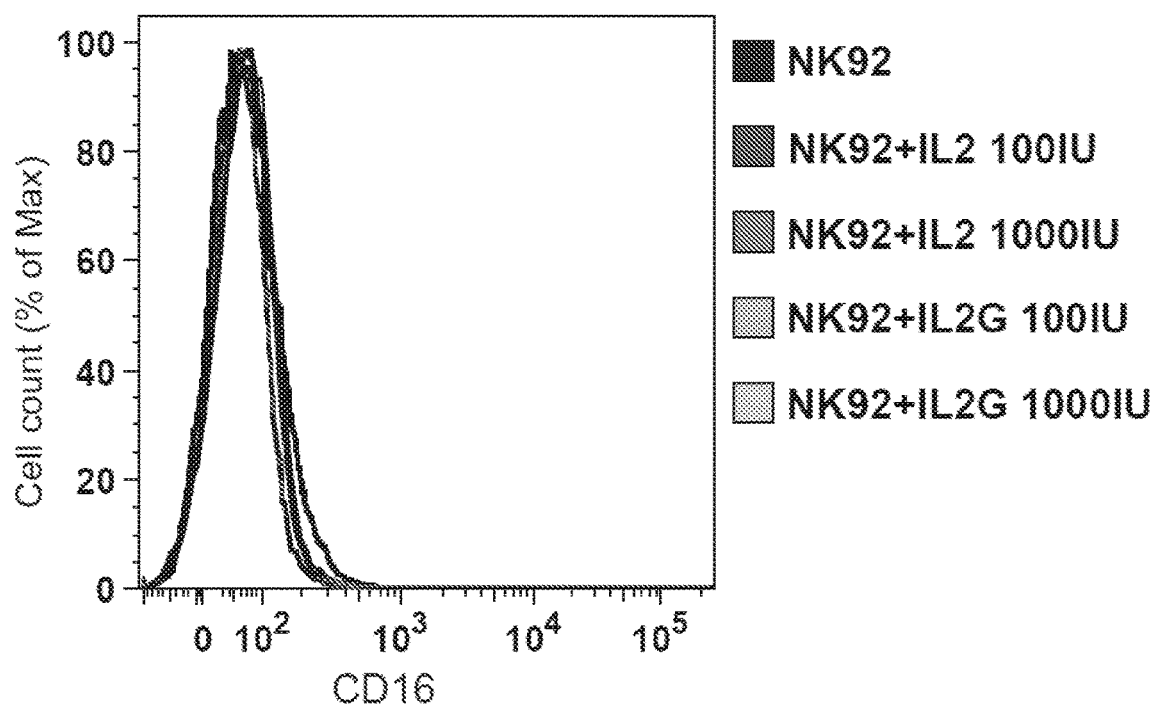

Example 5. CD16 is Substantially Induced by Endogenous Expression of the Chimera CIRB In accordance with the original characterization of NK92 cells (43), NK92 cells are CD56+, CD3-, CD16-, CD25+, CD45+ and NKg2D- (FIG. 5A), In comparison, NK92$^{IL2}$ cells, NK92$^{CIRB}$ cells, and freshly isolated human NK (hNK) cells display different patterns of marker expression. Unlike NK92, the cell lines NK92$^{IL2}$, NK92$^{CIRB}$, and hNK cells are all CD16+, with expression levels of hNK>NK92$^{CIRB}$>NK92$^{IL2}$ (FIG. 5B). We also examined the IL2-independent NK92-MI, and in accordance with a previous report (38), did not find any expression of CD16 (FIG. 10A). We also found no CD16 expression in NK92 cells treated with glycosylated or non-glycosylated IL2 (FIG. 10B). Human NK (hNK) cells express much higher levels of CD16 and NKG2D (FIG. 5B), than all NK92 cell lines and are virtually CD25-negative, while NK92$^{CIRB}$ cells expressed lower amounts of CD25 than both IL2-stimulated NK92 or NK92$^{IL2}$. Of the NK92 cell lines, NK92$^{CIRB}$ expression for CD25 and CD16 were most similar to hNK.

Example 6. ADCC of NK92$^{IL2}$ and NK92$^{CIRB}$ Against HER2 Positive Breast Cancer Cell Line BT474

Figure 5C:
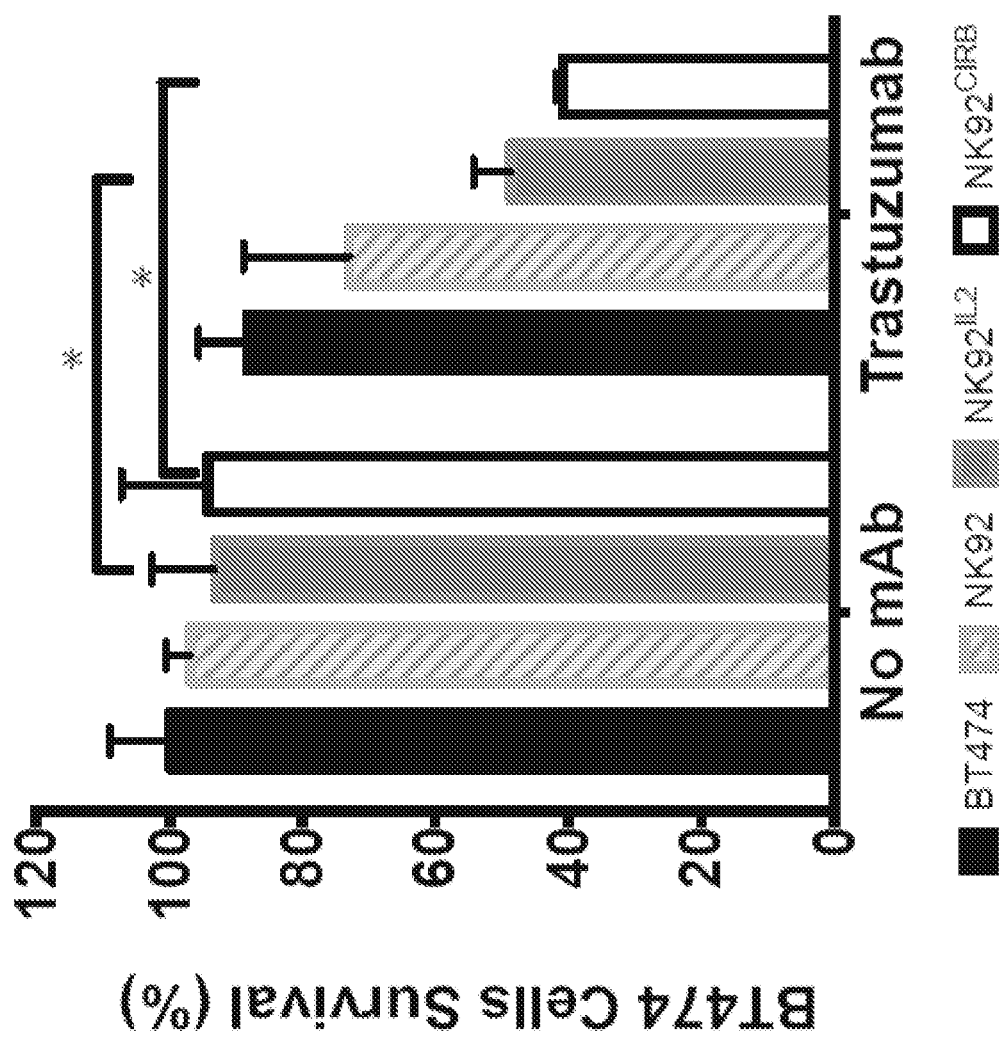
Figure 5D:
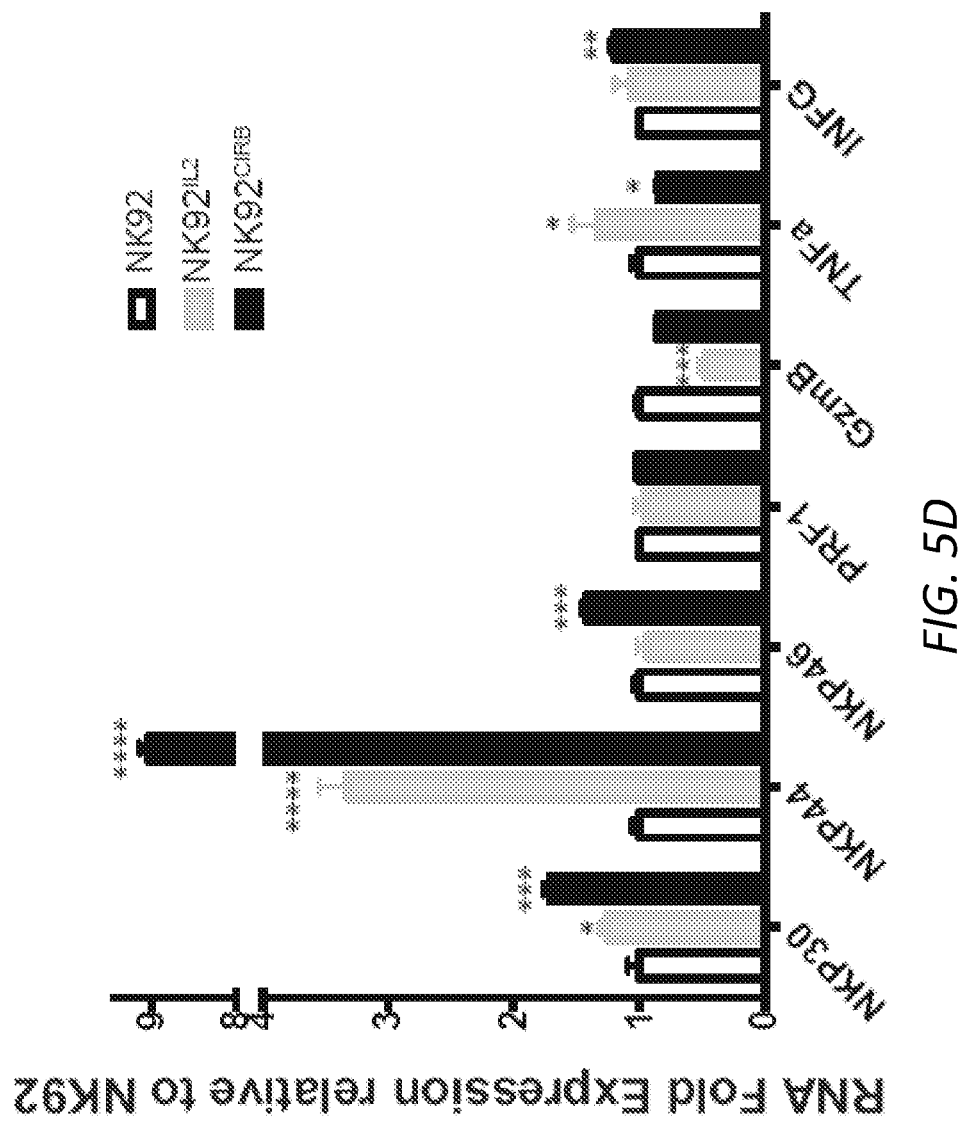

We next examined the impact of CD16 expression on ADCC using Trastuzumab against an HER2 positive breast cancer cell line BT474. FIG. 5C shows that in the absence Trastuzumab and when using an E/T ratio of 2:1, BT474 cells were not affected by the direct cytotoxicity of NK cells. However, in the presence of 1 ug/ml Trastuzumab both NK92$^{CIRB}$ and NK92$^{IL2}$ exerted substantial cytotoxicity of about 60% and 50%, respectively. Trastuzumab alone at 1 ug/ml did not affect significantly the survival of BT474. Similarly, parental NK92 did not provoke any significant cytotoxicity against BT474 in the presence of Tratstuzumab.

Example 7. Expression Profiles of Cytotoxicity Effectors in NK92, NK92$^{IL2}$ and NK92CIRB qPCR analysis of NK92$^{CIRB}$ cells revealed dramatic increases of natural cytotoxicity receptor (NCRs), NKP30 (1.7 fold), NKP44 (9 fold) and NKP46 (1.4 fold), compared to NK92$^{IL2}$ and parental NK92 stimulated with IL2 for 48 hours. In NK92$^{IL2}$, NKP44 expression also increased (3.3 fold). While Perforin-1 expression was similar in all cell lines, Granzyme-B expression declined and TNF-α increased in NK92$^{IL2}$ and both declined marginally while IFN-gamma increased in NK92CIRB

Figure 6A:
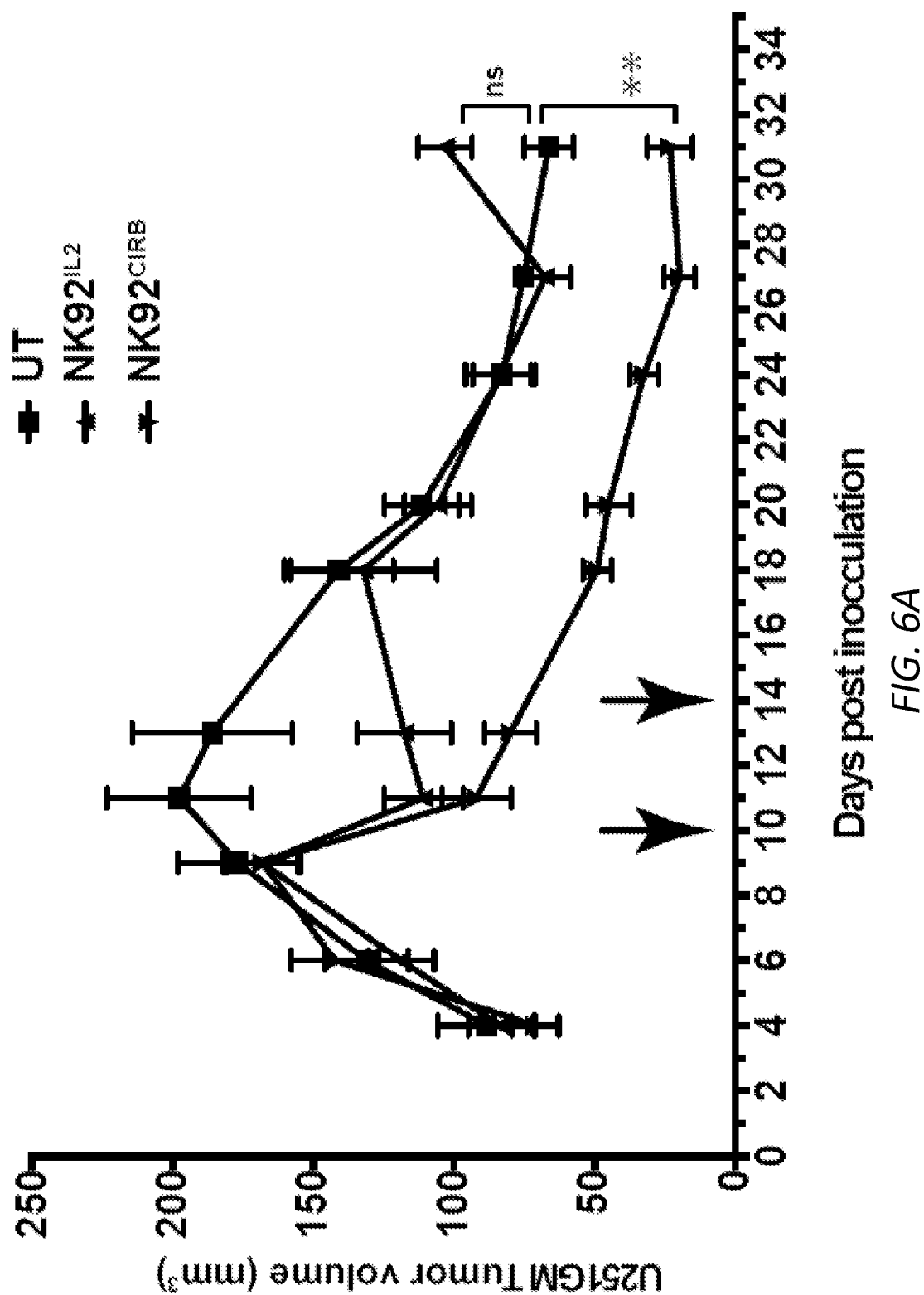
FIGS. 6A-B—Non-irradiated NK92$^{IL2}$ and NK92$^{CIRB}$ cells evaluation in vivo. A, When U251 tumor volume reached ~160 mm³, non-irradiated NK92$^{IL2}$ and NK92$^{CIRB}$ cells ($10^7$ cells) were injected into mice (arrows), via the tail vein. A second injection of non-irradiated NK cells ($5 \times 10^6$ cells) was carried out 4 days later. Tumor sizes were monitored until 31 days post tumor implantation. B, 17 days after the last NK cells injection, animals were sacrificed and blood was collected from 3 animals in each group. Blood samples (0.5 ml) were processed and analyzed by flow cytometry using human specific marker CD45 and the mCherry fluorescence marker, which is co-expressed with IL2 or CIRB in NK92$^{IL2}$ and NK92$^{CIRB}$, respectively. NK92$^{CIRB}$ cells detected (circled)
Figure 6B:
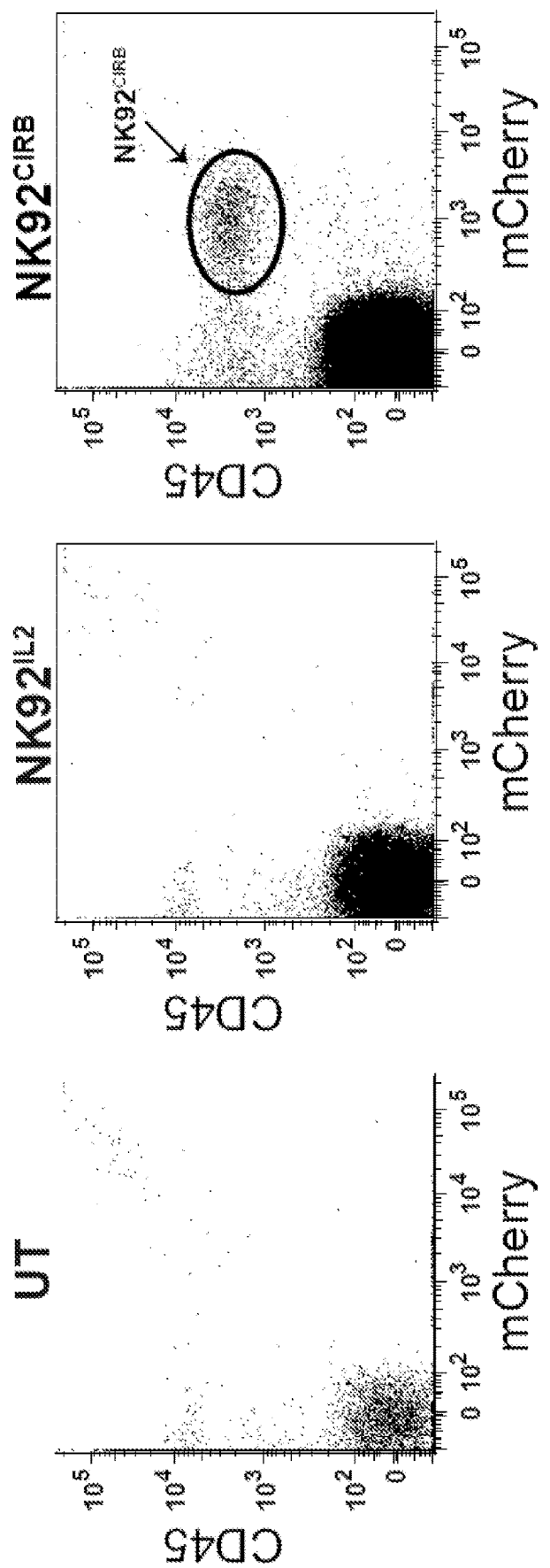

Example 8. In Vivo Detection of Circulating NK92$^{IL2}$ and NK92$^{CIRB}$ Cells The Survival and systemic circulation of NK92$^{IL2}$ and NK92$^{CIRB}$ in vivo, were evaluated in the context of tumor-bearing animals. U251MG tumor cells were grown s.c. in Nod/scid mice. When tumor size reached an average of 160 mm$^3$, animals received, within 4 days, two injections of non-irradiated NK92$^{IL2}$ and NK92CIRB cells via the tail vein. FIG. 6A shows that within 24 hours of the first injection of live NK92$^{CIRB}$ cells, rapid tumor volume regression of 46% was observed, while NK92IL2 cells caused 35% reduction. In contrast, tumors continued to grow in untreated animals to reach a maximal limit size nearing 200 mm$^3$ before regressing. This size-dependent limited growth was previously shown to be due to the poor angiogenesis of these tumors, which can be improved by VEGF expression (49). Tumor regression for NK92$^{CIRB}$-treated group continued after the second injection while the tumors in NK92$^{IL2}$-treated animals resumed growth and did not respond until day 18. Three weeks later, the untreated and NK92$^{IL2}$ groups showed a similar tumor size. In comparison the NK92$^{CIRB}$-treated group displayed a significant tumor volume reduction of 86%, 17 days post-NK cells injections, blood (0.5 ml) was collected from the three groups of mice and analyzed with cytometry for circulating cells expressing both mCherry, and human CD45. FIG. 6B shows that circulating NK cells can only be detected in the NK92$^{CIRB}$-treated group. This result suggests that CIRB expression but not IL2 secretion endows NK cells with the ability to persist in tumor bearing animals.

Example 9. Survival of Irradiated NK92$^{IL2}$ and NK92$^{CIRB}$ Cells

Figure 7A:
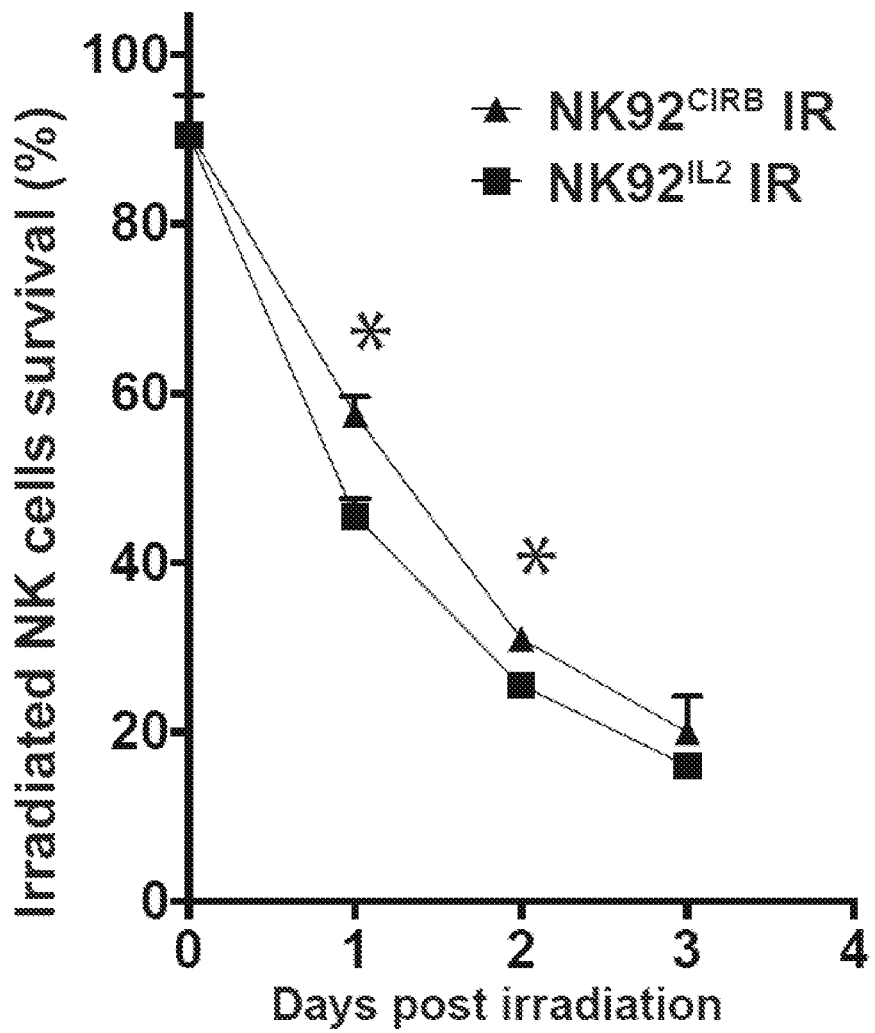
FIGS. 7A-B—Cell survival in vitro and anti-tumor efficacy of irradiated NK92$^{IL2}$ and NK92$^{CIRB}$ cells in vivo. A, NK cells were irradiated at 10 Gy (0.83 gy for 12 min) and then plated in complete NK92 media to determine their survival using Trypan Blue every 24 hours. The survival advantage of NK92$^{CIRB}$ cells was statistically significant at days 1 and 2 (One-way Anova test *P<0.05). B, PC-3 tumors were grown in 5 week-old male Nod/Scid mice. When tumor reached ~200 mm³ NK cells were irradiated with 500 cGy were administered, as four weekly injections of $15 \times 10^6$ cells in 200 ul per mouse, via the tail vein (arrows). After the last NK92$^{CIRB}$ cells injection, a significant tumor growth delay of 17 days was recorded (**P<0.01), comparatively to the untreated group. NK92$^{IL2}$ treated group tumors produced a tumor delay of only 7 days (*P<0.05). Statistical differences were determined using One-way Anova test.

NK92 cell line was isolated from an aggressive non-Hodgkin lymphoma patient (43). Therefore, FDA requires NK92 cells irradiation between 5 and 10 Gy prior to infusion to prevent proliferation. Under these conditions irradiated NK92 cells viability declines dramatically within 2 days. NK92$^{IL2}$ and NK92$^{CIRB}$ were irradiated at 10 Gy (0.83 gy for 12 min) and then plated in complete NK92 media to determine their survival using Trypan Blue every 24 hours. FIG. 7A shows that 24 hours post-irradiation, 57% of NK92$^{CIRB}$ cells and 45% of NK92$^{IL2}$ cells survive. The survival NK92$^{CIRB}$ advantage was statistically significant at days 1 and 2 (*P<0.05).

Figure 7B:
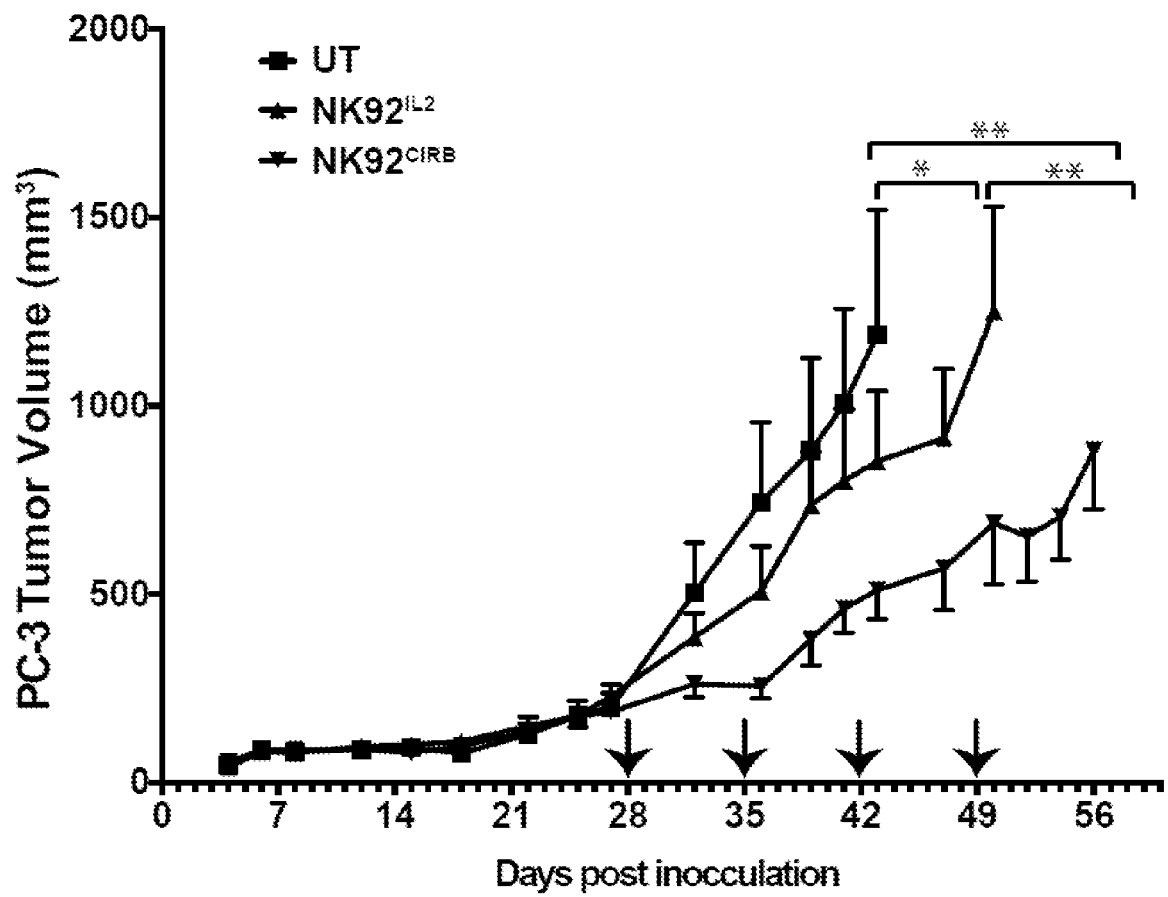
Figure 8:
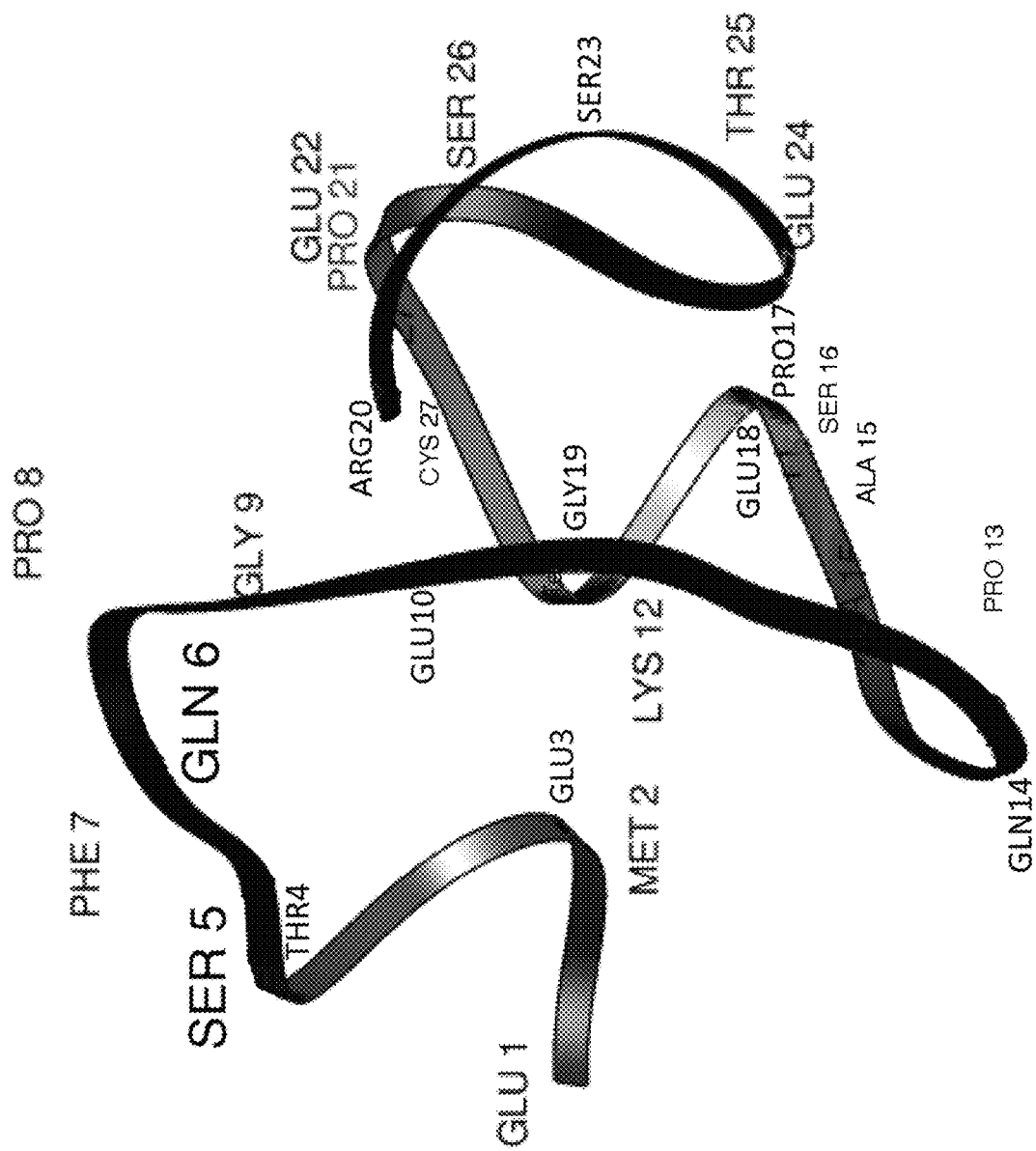
FIG. 8—Helix dominated predicted structure of the linker determined using the server(20). Figure discloses SEQ ID NO: 28.

Example 10. Anti-Tumor Efficacy of Irradiated NK92$^{IL2}$ and NK92$^{CIRB}$ Cells Prostate cancer cell line PC-3 (50) is androgen receptor and PSA negative and forms very aggressive tumors when grown in Nod/Scid mice. When tumor volumes reached ~200 mm$^3$ (day 28), irradiated NK cells (500 cGy) were administered as 4 weekly injections via the tail vein. FIG. 7B shows that the growth of PC-3 tumors in the NK92$^{CIRB}$-treated group was slowed after the first injection. After the last NK92$^{CIRB}$ cells injection, a significant tumor growth delay of about 17 days was recorded in the period between 1$^{st}$ and 4$^{th}$ NK92$^{CIRB}$ cells injections (**P<0.01), comparatively to the untreated group. In contrast, the NK92$^{IL2}$- treated group tumors produced only a tumor delay of 7 days from the untreated tumors group (*P<0.05).

Example 11. Design, Construction, and Testing of a CIRB21 Chimera

Figure 12:
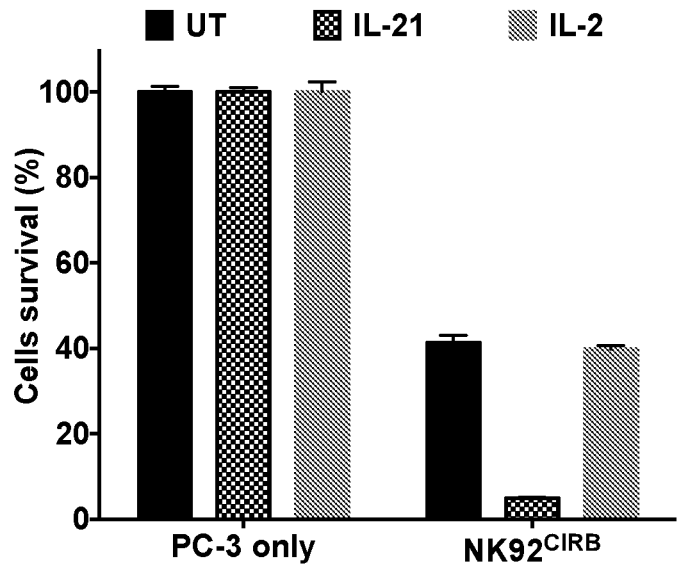
FIG. 12. NK92CIRB killing of PC-3 at a ratio of 1:1, when stimulated with IL21 or IL2.

Interleukins IL4, IL7, IL9, IL15 and IL21 belong to the same family as IL2, and use the same common IL2Rg. They all have their own private receptors, except for IL2 and IL15, which use IL2Rβ in addition to their own alpha receptors (FIG. 11). We examined the impact of added cytokines (IL2, IL4, IL7, and IL21) on the cytotoxicity of NK92 cells expressing the chimera NK92$^{CIRB}$, against PC-3 cells. We found that only IL21 was able to enhance dramatically their cytotoxicity (FIG. 12, shows only IL21 and IL2 impact). This prompted us to ask whether, if IL2 and IL21 use the same IL2Rg, it would be possible to combine the signaling of both in one chimeric cytokine receptor. To answer that, the entire cytoplasmic domain of IL21R was cloned then added Head-to-Tail to the C-terminal of IL2Rβ in the chimera CIRB. This resulted in a novel IL2-IL2Rβ-IL21R chimera (called CIRB21, exemplified in FIG. 13), which was then introduced in NK92 cells to yield NK92$^{CIRB21}$.

```
Nucleotide Sequence of IL2-IL2Rβ-IL21R (CIRB21)
                                    (SEQ ID NO: 32)
ATGTACAGGATGCAACTCCTGTCTTGCATTGCACTAAGTCTTGCACTTG

TCACAAACAGTGCACCTACTTCAAGTTCTACAAAGAAAACACAGCTACA

ACTGGAGCATTTACTGCTGGATTTACAGATGATTTTGAATGGAATTAAT

AATTACAAGAATCCCAAACTCACCAGGATGCTCACATTTAAGTTTTACA

TGCCCAAGAAGGCCACAGAACTGAAACATCTTCAGTGCCTAGAAGAAGA

ACTCAAACCTCTGGAGGAAGTGCTAAATTTAGCTCAAAGCAAAAACTTT

CACTTAAGACCCAGGGACTTAATCAGCAATATCAACGTAATAGTTCTGG

AACTAAAGGGATCTGAAACAACATTCATGTGTGAATATGCTGATGAGAC

AGCAACCATTGTAGAATTTCTGAACAGATGGATTACCTTTTGTCAAAGC

ATCATCTCAACACTGACTGAGCAGAAGCTCATTTCGGAAGAAGACCTTG

AAATGGAGACCAGTCAGTTTCCAGGTGAAGAGAAGCCTCAGGCAAGCCC

CGAAGGCCGTCCTGAGAGTGAGACTTCCTGCGCGGTGAATGGCACTTCC

CAGTTCACATGCTTCTACAACTCGCGAGCCAACATCTCCTGTGTCTGGA

GCCAAGATGGGGCTCTGCAGGACACTTCCTGCCAAGTCCATGCCTGGCC

GGACAGACGGCGGTGGAACCAAACCTGTGAGCTGCTCCCCGTGAGTCAA

GCATCCTGGGCCTGCAACCTGATCCTCGGAGCCCCAGATTCTCAGAAAC

TGACCACAGTTGACATCGTCACCCTGAGGGTGCTGTGTCGTGAGGGGGT

GCGATGGAGGGTGATGGCCATCCAGGACTTCAAGCCCTTTGAGAACCTT

CGCCTGATGGCCCCCATCTCCCTCCAAGTTGTCCACGTGGAGACCCACA

GATGCAACATAAGCTGGGAAATCTCCCAAGCCTCCCACTACTTTGAAAG

ACACCTGGAGTTCGAGGCCCGGACGCTGTCCCAGGCCACACCTGGGAG

GAGGCCCCCTGCTGACTCTCAAGCAGAAGCAGGAATGGATCTGCCTGG

AGACGCTCACCCCAGACACCCAGTATGAGTTTCAGGTGCGGGTCAAGCC

TCTGCAAGGCGAGTTCACGACCTGGAGCCCCTGGAGCCAGCCCCTGCC

TTCAGGACAAAGCCTGCAGCCCTTGGGAAGGACACCATTCCGTGGCTCG

GCCACCTCCTCGTGGGTCTCAGCGGGGCTTTTGGCTTCATCATCTTAGT

GTACTTGCTGATCAACTGCAGGAACACCGGGCCATGGCTGAAGAAGGTC

CTGAAGTGTAACACCCCAGACCCCTCGAAGTTCTTTTCCCAGCTGAGCT

CAGAGCATGGAGGAGACGTCCAGAAGTGGCTCTCTTCGCCCTTCCCCTC

ATCGTCCTTCAGCCCTGGCGGCCTGGCACCTGAGATCTCGCCACTAGAA

GTGCTGGAGAGGGACAAGGTGACGCAGCTGCTCCTGCAGCAGGACAAGG

TGCCTGAGCCCGCATCCTTAAGCAGCAACCACTCGCTGACCAGCTGCTT

CACCAACCAGGGTTACTTCTTCTTCCACCTCCCGGATGCCTTGGAGATA

GAGGCCTGCCAGGTGTACTTTACTTACGACCCCTACTCAGAGGAAGACC

CTGATGAGGGTGTGGCCGGGGCACCCACAGGGTCTTCCCCCCAACCCCT

GCAGCCTCTGTCAGGGGAGGACGACGCCTACTGCACCTTCCCCTCCAGG

GATGACCTGCTGCTCTTCTCCCCCAGTCTCCTCGGTGGCCCCAGCCCCC

CAAGCACTGCCCCTGGGGCAGTGGGGCCGGTGAAGAGAGGATGCCCCC

TTCTTTGCAAGAAAGAGTCCCCAGAGACTGGGACCCCCAGCCCCTGGGG

CCTCCCACCCCAGGAGTCCCAGACCTGGTGGATTTTCAGCCACCCCTG

AGCTGGTGCTGCGAGAGGCTGGGGAGGAGGTCCCTGACGCTGGCCCCAG

GGAGGGAGTCAGTTTCCCCTGGTCCAGGCCTCCTGGGCAGGGGGAGTTC

AGGGCCCTTAATGCTCGCCTGCCCCTGAACACTGATGCCTACTTGTCCC

TCCAAGAACTCCAGGGTCAGGACCCAACTCACTTGGTGAGCCTGAAGAC

CCATCCATTGTGGAGGCTATGAAGAAGATATGGGCCGTCCCCAGCCCT

GAGCGGTTCTTCATGCCCCTGTACAAGGGCTGCAGCGGAGACTTCAAGA

AATGGGTGGGTGCACCCTTCACTGGCTCCAGCCTGGAGCTGGGACCCTG

GAGCCCAGAGGTGCCCTCCACCCTGGAGGTGTACAGCTGCCACCCACCA

CGGAGCCCGGCCAAGAGGCTGCAGCTCACGGAGCTACAAGAACCAGCAG

AGCTGGTGGAGTCTGACGGTGTGCCCAAGCCCAGCTTCTGGCCGACAGC

CCAGAACTCGGGGGGCTCAGCTTACAGTGAGGAGAGGGATCGGCCATAC

GGCCTGGTGTCCATTGACACAGTGACTGTGCTAGATGCAGAGGGCCAT

GCACCTGGCCCTGCAGCTGTGAGGATGACGGCTACCCAGCCCTGGACCT

GGATGCTGGCCTGGAGCCCAGCCCAGGCCTAGAGGACCCACTCTTGGAT

GCAGGGACCACAGTCCTGTCCTGTGGCTGTGTCTCAGCTGGCAGCCCTG

GGCTAGGAGGGCCCCTGGGAAGCCTCCTGGACAGACTAAAGCCACCCCT

TGCAGATGGGGAGGACTGGGCTGGGGGACTGCCCTGGGGTGGCCGGTCA

CCTGGAGGGGTCTCAGAGAGTGAGGCGGGCTCACCCCTGGCCGGCCTGG

ATATGGACACGTTTGACAGTGGCTTTGTGGGCTCTGACTGCAGCAGCCC

TGTGGAGTGTGACTTCACCAGCCCCGGGGACGAAGGACCCCCCCGGAGC

TACCTCCGCCAGTGGGTGGTCATTCCTCCGCCACTTTCGAGCCCTGGAC

CCCAGGCCAGCTAA

Protein Sequence of IL2-IL2Rβ-IL21R (CIRB21)
                                    (SEQ ID NO: 33)
MYRMQLLSCIALSLALVTNSAPTSSSTKKTQLQLEHLLLDLQMILNGIN

NYKNPKLTRMLTFKFYMPKKATELKHLQCLEEELKPLEEVLNLAQSKNF
```

-continued

```
HLRPRDLISNINVIVLELKGSETTFMCEYADETATIVEFLNRWITFCQS

IISTLTEQKLISEEDLEMETSQFPGEEKPQASPEGRPESETSCAVNGTS

QFTCFYNSRANISCVWSQDGALQDTSCQVHAWPDRRRWNQTCELLPVSQ

ASWACNLILGAPDSQKLTTVDIVTLRVLCREGVRWRVMAIQDFKPFENL

RLMAPISLQVVHVETHRCNISWEISQASHYFERHLEFEARTLSPGHTWE

EAPLLTLKQKQEWICLETLTPDTQYEFQVRVKPLQGEFTTWSPWSQPLA

FRTKPAALGKDTIPWLGHLLVGLSGAFGFIILVYLLINCRNTGPWLKKV

LKCNTPDPSKFFSQLSSEHGGDVQKWLSSPFPSSSFSPGGLAPEISPLE

VLERDKVTQLLLQQDKVPEPASLSSNHSLTSCFTNQGYFFFHLPDALEI

EACQVYFTYDPYSEEDPDEGVAGAPTGSSPQPLQPLSGEDDAYCTFPSR

DDLLLFSPSLLGGPSPPSTAPGGSGAGEERMPPSLQERVPRDWDPQPLG

PPTPGVPDLVDFQPPPELVLREAGEEVPDAGPREGVSFPWSRPPGQGEF

RALNARLPLNTDAYLSLQELQGQDPTHLVSLKTHPLWRLWKKIWAVPSP

ERFFMPLYKGCSGDFKKWVGAPFTGSSLELGPWSPEVPSTLEVYSCHPP

RSPAKRLQLTELQEPAELVESDGVPKPSFWPTAQNSGGSAYSEERDRPY

GLVSIDTVTVLDAEGPCTWPCSCEDDGYPALDLDAGLEPSPGLEDPLLD

AGTTVLSCGCVSAGSPGLGGPLGSLLDRLKPPLADGEDWAGGLPWGGRS

PGGVSESEAGSPLAGLDMDTFDSGFVGSDCSSPVECDFTSPGDEGPPRS

YLRQWVVIPPPLSSPGPQAS*
```

Figure 14:
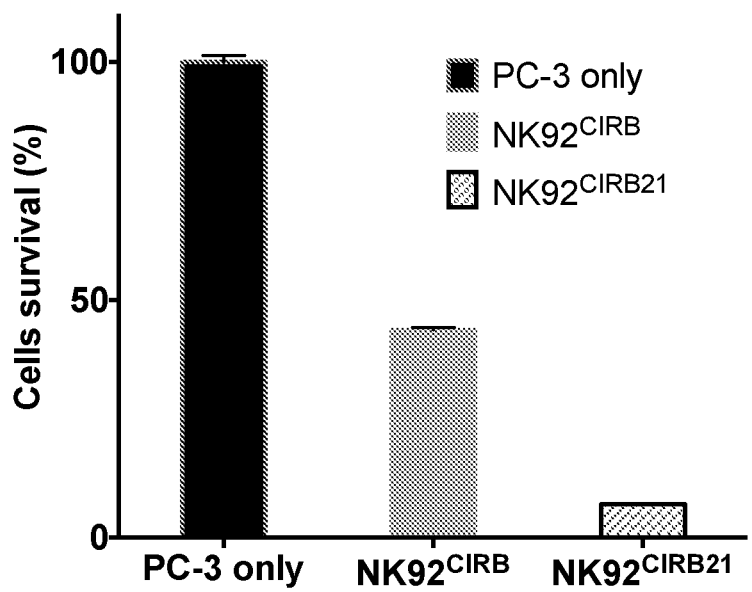
FIG. 14. Graph showing the cytotoxicity of NK92CIRB and NK92CIRB21 vs. PC-3 cells at a ratio of 1:1.

FIG. 14 shows that the new hybrid receptor confers substantial cytotoxicity against PC-3 cancer cells that is 5 fold better than the original chimera CIRB and also produces CD16. They also had slower growth, which could be enhanced by exogenous IL2 addition to the media.

Figure 15:
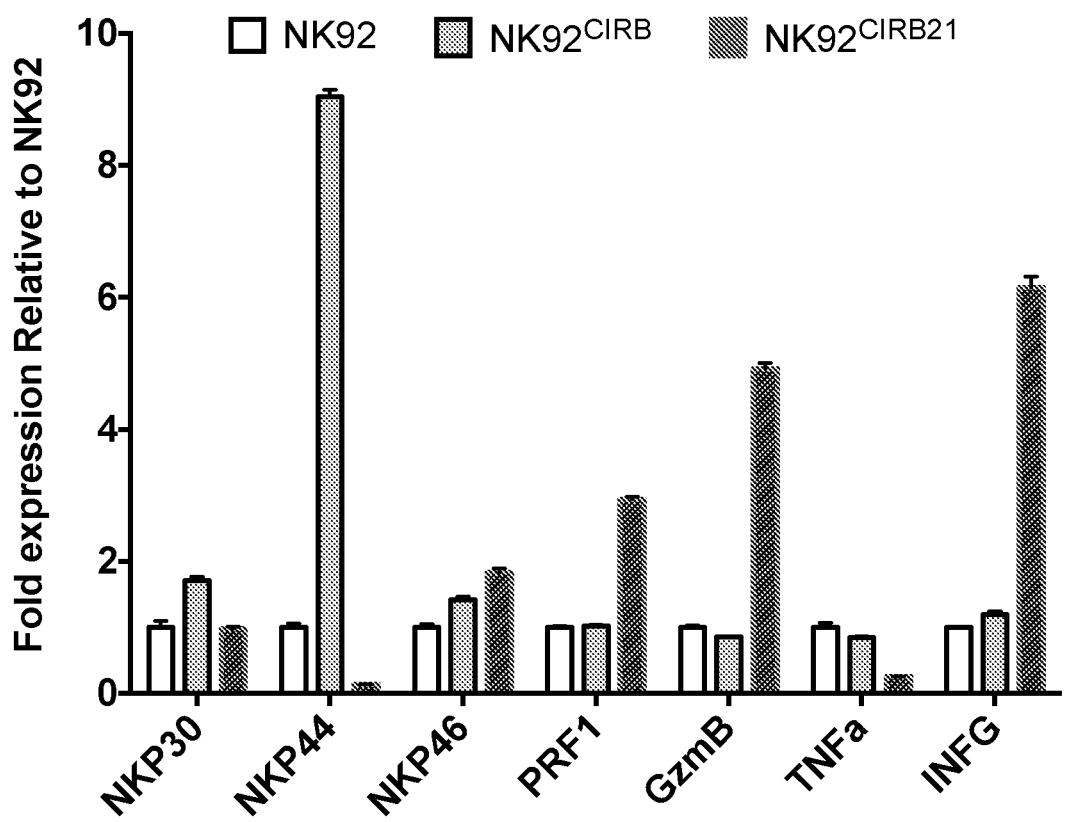
FIG. 15. Graph showing folds expression of activators and cytokines in NK92CIRB and NK92CIRB21 relative to NK92.

While IL2 has been shown to mainly activate STAT5 (51), IL21 preferentially activates STAT3 (52,53) and STAT1 (54). It has been shown that this activation leads to Interferon-gamma (IFN-g) production (55) and this might explain the dramatic enhancement in cancer cell killing we saw (FIG. 14). RNA expression analysis by qPCR revealed the remarkable extent of activation driven by the hybrid receptor CIRB21 compared to CIRB. FIG. 15 shows that IFN-g, Granzyme-B and Perform-1 were increased in CIRB21 by 5, 6 and 3 fold, respectively, above the levels in CIRB and NK92. These data confirm that this novel platform of IL2 signaling through hybrid receptors holds a therapeutic promise for superior NK cells activation.

However, IL-21 signaling also induces the transcription of many other genes (reviewed in (56)) including suppressor of cytokine signaling 1 (SOCS1) and SOCS3 proteins, which down regulate the JAK-STAT pathway and inhibit signaling by IL2 (57,58). This inhibition could be behind the slower growth of NK92 expressing the chimera CIRB21.

It was first hypothesized that in the chimera CIRB21, the activation of STAT3 mediated by IL21R may be in conflict with the activation of STAT5 mediated by IL2Rβ, resulting in slower NK92CIRB21 cell growth. STAT3 is a major byproduct of IL21R signaling and its transcriptional activity could be behind the down regulation of JAK-STAT signaling mediated by IL2 in our cell line. Among STAT3 potent and selective inhibitors, 5,15-Diphenylporphyrin (5,15-DPP) acts in the nanomolar range and prevents STAT3 nuclear translocation. However, when we inhibited the dimerization of STAT3 using specific with 5,15-DPP, we did not improve NK92CIRB21 cell growth. This result suggests either the absence of STAT3 homodimers and the possible heterodimerization of STAT1 and STAT3 or a predominance of STAT1 homodimers. STAT1 and STAT3 have usually opposing biological effects. While STAT3 is an oncogene (59,60), STAT1 acts as a tumor suppressor (61,62). STAT1 phosphorylation can be mediated by IFNg (63), which is highly produced in NK92CIRB21. Therefore, it is possible that the slower growth of NK92CIRB21 cells is caused by STAT1 tumor suppressor activity.

Figure 16:
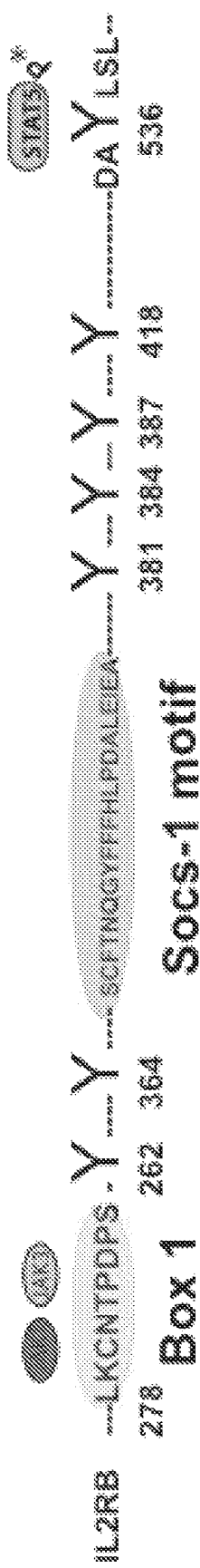
FIG. 16. IL2Rβ receptor cytoplasmic domain with the activation regions depicted. Box 1 is required for JAK-STAT interaction with Socs 1 inhibitory motif. Y536 is required for STAT5 binding and phosphorylation. Figure discloses SEQ ID NOS 41-43, respectively in order of appearance.
Figure 17:
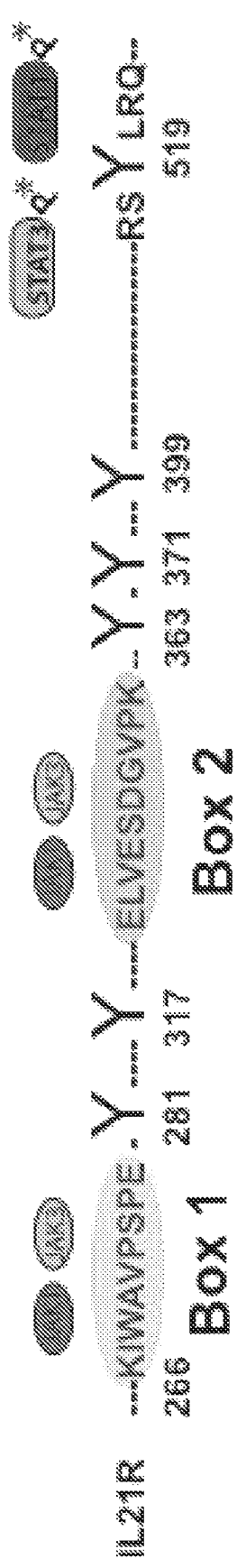
FIG. 17. IL21 receptor cytoplasmic domain with the activation regions depicted. Box 1 is required for JAK-STAT interaction with Box 2 contribution. Y519 is required for STAT3 and STAT1 binding and phosphorylation. Figure discloses SEQ ID NOS 44-46, respectively in order of appearance.

Three methodologies are used to restore faster growth of NK92CIRB21 without affecting their current dramatic cytotoxicity. First, it is possible that the current configuration of CIRB21 is sterically unfavorable to IL2Rβ due to lack of a spacer between the two cytoplasmic domains of IL2Rβ and IL21R in the exemplary construct. Therefore, the CIRB21 chimera is modified to add a flexible linker, e.g., a (GGGS)$_n$ linker, between IL2Rβ and IL21R. This is done using high fidelity PCR using the method of overlapping extension. The impact of the linker is examined by stable expression of the resulting chimera in NK92 cells. Second, if the addition of a linker does not restore NK92 cells growth then the Socs1 motif, which down regulates the JAK-STAT pathway and inhibits signaling by IL2 (57,58), is removed from the receptor IL2Rβ (FIG. 16). This is achieved by site mutagenic high fidelity PCR using primers sense 5'-GCAGCAAC-CACTCGCTGACCGCCTGCCAGGTGTACTTTAC-3' (SEQ ID NO:34) and reverse 5'-GTAAAGTA-CACCTGGCAGGCGGTCAGCGAGTGG TTGCTGC-3' (SEQ ID NO:35). We also weaken the signal transduction of IL21R by deleting Box-2 region of IL21R cytoplasmic domain (FIG. 17). Box-1, and to a lesser degree Box-2, are both involved in the signal transduction of IL21 ((64)). Separately, we also remove Box-2 along with the region comprised between tyrosine Y317 and Y399, which was shown to contribute marginally to the overall strength of the IL21 signaling (53). Third, if these genetic modifications do not restore NK92 cells growth, then the DNA shuffling of the cytoplasmic domains of IL2Rβ and IL21R may yield a novel chimera which enables faster growth of NK cells.

REFERENCES

1. Caligiuri M A. Human natural killer cells. Blood 2008; 112(3):461-9.
2. Vidal S M, Khakoo S I, Biron C A. Natural killer cell responses during viral infections: flexibility and conditioning of innate immunity by experience. Curr Opin Virol 2011; 1(6):497-512.
3. Orr M T, Lanier L L. Natural killer cell education and tolerance. Cell 2010; 142(6):847-56.
4. Malek T R. The biology of interleukin-2. Annu Rev Immunol 2008; 26:453-79.
5. Dahlberg C I, Sarhan D, Chrobok M, Duru A D, Alici E. Natural Killer Cell-Based Therapies Targeting Cancer: Possible Strategies to Gain and Sustain Anti-Tumor Activity. Front Immunol 2015; 6:605.
6. Maas R A, Dullens H F, Den Otter W. Interleukin-2 in cancer treatment: disappointing or (still) promising? A review. Cancer Immunol Immunother 1993; 36(3):141-8.
7. Glauser F L, DeBlois G, Bechard D, Fowler A A, Merchant R, Fairman R P. Cardiopulmonary toxicity of adoptive immunotherapy. Am J Med Sci 1988; 296(6): 406-12.
8. Ardizzoni A, Bonavia M, Viale M, Baldini E, Mereu C, Verna A, et al. Biologic and clinical effects of continuous infusion interleukin-2 in patients with non-small cell lung cancer. Cancer 1994; 73(5):1353-60.
9. Donohue J H, Rosenberg S A. The fate of interleukin-2 after in vivo administration. J Immunol 1983; 130(5): 2203-8.
10. Shevach E M. Regulatory T cells in autoimmmunity*. Annu Rev Immunol 2000; 18:423-49.
11. Parkhurst M R, Riley J P, Dudley M E, Rosenberg S A. Adoptive transfer of autologous natural killer cells leads to high levels of circulating natural killer cells but does not mediate tumor regression. Clin Cancer Res 2011; 17(19):6287-97.
12. Rubnitz J E, Inaba H, Ribeiro R C, Pounds S, Rooney B, Bell T, et al. NKAML: a pilot study to determine the safety and feasibility of haploidentical natural killer cell transplantation in childhood acute myeloid leukemia. J Clin Oncol 2010; 28(6):955-9.
13. Vales-Gomez M, Reyburn H T, Mandelboim M, Strominger J L. Kinetics of interaction of HLA-C ligands with natural killer cell inhibitory receptors. Immunity 1998; 9(3):337-44.
14. Miller J S, Soignier Y, Panoskaltsis-Mortari A, McNeamey S A, Yun G H, Fautsch S K, et al. Successful adoptive transfer and in vivo expansion of human haploidentical NK cells in patients with cancer. Blood 2005; 105(8):3051-7.
15. Geller M A, Cooley S, Judson P L, Ghebre R, Carson L F, Argenta P A, et al. A phase I I study of allogeneic natural killer cell therapy to treat patients with recurrent ovarian and breast cancer. Cytotherapy 2011; 13(1):98-107.
16. Nagashima S, Mailliard R, Kashii Y, Reichert T E, Herberman R B, Robbins P, et al. Stable transduction of the interleukin-2 gene into human natural killer cell lines and their phenotypic and functional characterization in vitro and in vivo. Blood 1998; 91(10):3850-61.
17. Konstantinidis K V, Alici E, Aints A, Christensson B, Ljunggren H G, Dilber M S. Targeting IL-2 to the endoplasmic reticulum confines autocrine growth stimulation to NK-92 cells. Exp Hematol 2005; 33(2):159-64.
18. Mao Y, Sarhan D, Steven A, Seliger B, Kiessling R, Lundqvist A. Inhibition of tumor-derived prostaglandin-e2 blocks the induction of myeloid-derived suppressor cells and recovers natural killer cell activity. Clin Cancer Res 2014; 20(15):4096-106.
19. Bluestone J A, Abbas A K. Natural versus adaptive regulatory T cells. Nat Rev Immunol 2003; 3(3):253-7.
20. Rickert M, Wang X, Boulanger M J, Goriatcheva N, Garcia K C. The structure of interleukin-2 complexed with its alpha receptor. Science 2005; 308(5727):1477-80.
21. Leonard W J, Depper J M, Crabtree G R, Rudikoff S, Pumphrey J, Robb R J, et al. Molecular cloning and expression of cDNAs for the human interleukin-2 receptor. Nature 1984; 311(5987):626-31.
22. Hatakeyama M, Tsudo M, Minamoto S, Kono T, Doi T, Miyata T, et al. Interleukin-2 receptor beta chain gene: generation of three receptor forms by cloned human alpha and beta chain cDNA's. Science 1989; 244(4904):551-6.
23. Takeshita T, Asao H, Ohtani K, Ishii N, Kumaki S, Tanaka N, et al. Cloning of the gamma chain of the human IL-2 receptor. Science 1992; 257(5068):379-82.
24. Stauber D J, Debler E W, Horton P A, Smith K A, Wilson I A. Crystal structure of the IL-2 signaling complex: paradigm for a heterotrimeric cytokine receptor. Proc Natl Acad Sci USA 2006; 103(8):2788-93.
25. Voss S D, Sondel P M, Robb R J. Characterization of the interleukin 2 receptors (IL-2R) expressed on human natural killer cells activated in vivo by IL-2: association of the p64 IL-2R gamma chain with the IL-2R beta chain in functional intermediate-affinity IL-2R. J Exp Med 1992; 176(2):531-41.
26. Caligiuri M A, Zmuidzinas A, Manley T J, Levine H, Smith K A, Ritz J. Functional consequences of interleukin 2 receptor expression on resting human lymphocytes. Identification of a novel natural killer cell subset with high affinity receptors. J Exp Med 1990; 171(5):1509-26.
27. Levin A M, Bates D L, Ring A M, Krieg C, Lin J T, Su L, et al. Exploiting a natural conformational switch to engineer an interleukin-2 'superkine'. Nature 2012; 484 (7395):529-33.
28. Vihinen M. Relationship of protein flexibility to thermostability. Protein Eng 1987; 1(6):477-80.
29. Lohr M, Schmidt C, Ringel J, Kluth M, Muller P, Nizze H, et al. Transforming growth factor-beta1 induces desmoplasia in an experimental model of human pancreatic carcinoma. Cancer Res 2001; 61(2):550-5.
30. Ghiringhelli F, Menard C, Terme M, Flament C, Taieb J, Chaput N, et al. CD4+CD25+ regulatory T cells inhibit natural killer cell functions in a transforming growth factor-beta-dependent manner. J Exp Med 2005; 202(8): 1075-85.
31. Li H, Han Y, Guo Q, Zhang M, Cao X. Cancer-expanded myeloid-derived suppressor cells induce anergy of NK cells through membrane-bound TGF-beta 1. J Immunol 2009; 182(1):240-9.
32. Clayton A, Mitchell J P, Court J, Linnane S, Mason M D, Tabi Z. Human tumor-derived exosomes down-modulate NKG2D expression. J Immunol 2008; 180(11):7249-58.
33. Clayton A, Mitchell J P, Court J, Mason M D, Tabi Z. Human tumor-derived exosomes selectively impair lymphocyte responses to interleukin-2. Cancer Res 2007; 67(15):7458-66.
34. Donatelli S S, Zhou J M, Gilvary D L, Eksioglu E A, Chen X, Cress W D, et al. TGF-beta-inducible microRNA-183 silences tumor-associated natural killer cells. Proc Natl Acad Sci USA 2014; 111(11):4203-8.
35. Hsu A K, Quach H, Tai T, Prince H M, Harrison S J, Trapani J A, et al. The immunostimulatory effect of lenalidomide on N K-cell function is profoundly inhibited by concurrent dexamethasone therapy. Blood 2011; 117 (5):1605-13.
36. Barnes P J. Anti-inflammatory actions of glucocorticoids: molecular mechanisms. Clin Sci (Lond) 1998; 94(6):557-72.
37. Boumpas D T, Anastassiou E D, Older S A, Tsokos G C, Nelson D L, Balow J E. Dexamethasone inhibits human interleukin 2 but not interleukin 2 receptor gene expression in vitro at the level of nuclear transcription. J Clin Invest 1991; 87(5):1739-47.
38. Tam Y K, Maki G, Miyagawa B, Hennemann B, Tonn T, Klingemann H G. Characterization of genetically altered, interleukin 2-independent natural killer cell lines suitable for adoptive cellular immunotherapy. Hum Gene Ther 1999; 10(8):1359-73.
39. Tai Y T, Dillon M, Song W, Leiba M, Li X F, Burger P, et al. Anti-CS1 humanized monoclonal antibody HuLuc63 inhibits myeloma cell adhesion and induces antibody-dependent cellular cytotoxicity in the bone marrow milieu. Blood 2008; 112(4):1329-37.
40. Glienke W, Esser R, Priesner C, Suerth J D, Schambach A, Wels W S, et al. Advantages and applications of CAR-expressing natural killer cells. Front Pharmacol 2015; 6:21.

41. Tonn T, Schwabe D, Klingemann H G, Becker S, Esser R, Koehl U, et al. Treatment of patients with advanced cancer with the natural killer cell line NK-92. Cytotherapy 2013; 15(12):1563-70.
42. Arai S, Meagher R, Swearingen M, Myint H, Rich E, Martinson J, et al. Infusion of the allogeneic cell line NK-92 in patients with advanced renal cell cancer or melanoma: a phase I trial. Cytotherapy 2008; 10(6):625-32.
43. Gong J H, Maki G, Klingemann H G. Characterization of a human cell line (NK-92) with phenotypical and functional characteristics of activated natural killer cells. Leukemia 1994; 8(4):652-8.
44. Suerth J D, Schambach A, Baum C. Genetic modification of lymphocytes by retrovirus-based vectors. Curr Opin Immunol 2012; 24(5):598-608.
45. Terme M, Ullrich E, Delahaye N F, Chaput N, Zitvogel L. Natural killer cell-directed therapies: moving from unexpected results to successful strategies. Nat Immunol 2008; 9(5):486-94.
46. Yang X O, Nurieva R, Martinez G J, Kang H S, Chung Y, Pappu B P, et al. Molecular antagonism and plasticity of regulatory and inflammatory T cell programs. Immunity 2008; 29(1):44-56.
47. Vihinen M, Torkkila E, Riikonen P. Accuracy of protein flexibility predictions. Proteins 1994; 19(2):141-9.
48. Nagler A, Lanier L L, Phillips J H. The effects of IL-4 on human natural killer cells. A potent regulator of IL-2 activation and proliferation. J Immunol 1988; 141(7):2349-51.
49. Ke L D, Shi Y X, Yung W K. VEGF(121), VEGF(165) overexpression enhances tumorigenicity in U251 M G but not in NG-1 glioma cells. Cancer Res 2002; 62(6):1854-61.
50. Kaighn M E, Narayan K S, Ohnuki Y, Lechner J F, Jones L W. Establishment and characterization of a human prostatic carcinoma cell line (PC-3). Invest Urol 1979; 17(1):16-23.
51. Fujii H, Nakagawa Y, Schindler U, Kawahara A, Mori H, Gouilleux F, et al. Activation of Stat5 by interleukin 2 requires a carboxyl-terminal region of the interleukin 2 receptor beta chain but is not essential for the proliferative signal transmission. Proc Natl Acad Sci USA 1995; 92(12):5482-6.
52. Asao H, Okuyama C, Kumaki S, Ishii N, Tsuchiya S, Foster D, et al. Cutting edge: the common gamma-chain is an indispensable subunit of the IL-21 receptor complex. J Immunol 2001; 167(1):1-5.
53. Strengell M, Sareneva T, Foster D, Julkunen I, Matikainen S. IL-21 up-regulates the expression of genes associated with innate immunity and Th1 response. J Immunol 2002; 169(7):3600-5.
54. Zeng R, Spolski R, Casas E, Zhu W, Levy D E, Leonard W J. The molecular basis of IL-21-mediated proliferation. Blood 2007; 109(10):4135-42.
55. Strengell M, Matikainen S, Siren J, Lehtonen A, Foster D, Julkunen I, et al. IL-21 in synergy with IL-15 or IL-18 enhances IFN-gamma production in human N K and T cells. J Immunol 2003; 170(11):5464-9.
56. Spolski R, Leonard W J. Interleukin-21: a double-edged sword with therapeutic potential. Nat Rev Drug Discov 2014; 13(5):379-95.
57. Endo T A, Masuhara M, Yokouchi M, Suzuki R, Sakamoto H, Mitsui K, et al. A new protein containing an SH2 domain that inhibits JAK kinases. Nature 1997; 387(6636):921-4.
58. Cohney S J, Sanden D, Cacalano N A, Yoshimura A, Mui A, Migone T S, et al. SOCS-3 is tyrosine phosphorylated in response to interleukin-2 and suppresses STAT5 phosphorylation and lymphocyte proliferation. Mol Cell Biol 1999; 19(7):4980-8.
59. Bromberg J F, Wrzeszczynska M H, Devgan G, Zhao Y, Pestell R G, Albanese C, et al. Stat3 as an oncogene. Cell 1999; 98(3):295-303.
60. Bromberg J. Stat proteins and oncogenesis. J Clin Invest 2002; 109(9):1139-42.
61. Chin Y E, Kitagawa M, Su W C, You Z H, Iwamoto Y, Fu X Y. Cell growth arrest and induction of cyclin-dependent kinase inhibitor p21 WAF1/CIP1 mediated by STAT1. Science 1996; 272(5262):719-22.
62. Kaplan D H, Shankaran V, Dighe A S, Stockert E, Aguet M, Old L J, et al. Demonstration of an interferon gamma-dependent tumor surveillance system in immunocompetent mice. Proc Natl Acad Sci USA 1998; 95(13):7556-61.
63. Qing Y, Stark G R. Alternative activation of STAT1 and STAT3 in response to interferon-gamma. J Biol Chem 2004; 279(40):41679-85.
64. Parrish-Novak J, Dillon S R, Nelson A, Hammond A, Sprecher C, Gross J A, et al. Interleukin 21 and its receptor are involved in NK cell expansion and regulation of lymphocyte function. Nature 2000; 408(6808):57-63.

OTHER EMBODIMENTS

It is to be understood that while the invention has been described in conjunction with the detailed description thereof, the foregoing description is intended to illustrate and not limit the scope of the invention, which is defined by the scope of the appended claims. For example, although human cells and sequences are exemplified herein, e.g., for use in treating human subjects, sequences and NK cells from other species can also be used. Other aspects, advantages, and modifications are within the scope of the following claims.

What is claimed is:

1. A fusion protein comprising interleukin 2 (IL2) fused to the N-terminus of full-length interleukin 2 receptor beta (IL2Rβ) without a signal peptide, with an intervening linker comprising an extracellular domain of IL2Rα, and a cytoplasmic domain of interleukin 21 receptor (IL21R) at the C-terminus of IL2Rβ, optionally with an intervening linker therebetween.

2. The fusion protein of claim 1, wherein:
the IL2 comprises SEQ ID NO:34, and/or
the IL2Rβ comprises amino acids 27-551 of SEQ ID NO:35.

3. The fusion protein of claim 1, wherein the extracellular domain of IL2Rα comprises SEQ ID NO:28.

4. The fusion protein of claim 1, wherein the cytoplasmic domain of IL21R comprises amino acids 254-538 of SEQ ID NO:36.

5. A nucleic acid encoding the fusion protein of claim 1.

6. An expression vector comprising the nucleic acid of claim 5, with one or more regulatory regions for expression of the fusion protein.

7. An isolated natural killer (NK) cell expressing a fusion protein of claim 1, optionally wherein the NK cell also expresses CD16 and optionally NKP44, NKP46 and NKP30.

* * * * *

SEQUENCE LISTING

```
<160> NUMBER OF SEQ ID NOS: 48

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```
tgcaggatcc actcacagta acctcaactc c                                31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgcactcgag agtgaaacca ttttagagcc                                  30

<210> SEQ ID NO 3
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggattacctt tgtcaaagc atcatctcaa cactgactga gcagaagctc atttcggaag    60
aagaccttga aatggagacc agtcagtttc cagg                              94

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cctgatatgt tttaagtggg aagcacttaa ttatcagatt gttcttctac tcttcctctg   60
tctcc                                                              65

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgcaggatcc actcacagta acctcaactc c                                 31

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggaagtgcc attcaccgcg caggaagtct cactctcagg a                      41

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggctctcgag ttgtagaagc atgtgaactg ggaagtgcca ttcaccgc                48

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catcttcagt gcctagaaga agaactc                                        27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagttcttct tctaggcact gaagatg                                        27

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcccagttc acatgcttct acaagtcgac agccaacatc tcctg                    45

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agcttctaga ctcgagttat cacaccaagt gagttgggtc ctgaccctgg               50

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctggtggtg gagaaagaac                                                20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 13
ggacctttcc aggtcagaca                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcacagccac agaactccac                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctgagctcc atcatggttt                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgccgtctag acactgcaac                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccaaaacatc ggtatgtccc                                                20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcctacctc aggcttatct c                                              21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
```

```
cctcgacagt caggcagtc                                              19
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ccctgggaaa acactcacac a                                           21
```

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
cacaactcaa tggtactgtc gt                                          22
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
cccagggacc tctctctaat ca                                          22
```

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
agctgcccct cagcttgag                                              19
```

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
tcggtaactg acttgaatgt cca                                         23
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
tccttttttcg cttccctgtt tt                                              22
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
atggggaagg tgaaggtcg                                                   19
```

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
ggggtcattg atggcaacaa ta                                               22
```

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Glu Met Glu Thr Ser Gln Phe Pro Gly Glu Glu Lys Pro Gln Ala Ser
1               5                   10                  15

Pro Glu Gly Arg Pro Glu Ser Glu Thr Ser Cys
            20                  25
```

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Glu Gln Lys Leu Ile Ser Glu Glu Asp Leu
1               5                   10
```

<210> SEQ ID NO 30
<211> LENGTH: 2148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat acaagaatc ccaaactcac caggatgctc     180
acatttaagt tttacatgcc caagaaggcc acagaactga acatcttca gtgcctagaa     240 gaagaactca aacctctgga ggaagtgcta aatttagctc aaagcaaaaa ctttcactta    300
```

```
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactg agcagaagct catttcggaa    480
gaagaccttg aaatggagac cagtcagttt ccaggtgaag agaagcctca ggcaagcccc    540
gaaggccgtc ctgagagtga acttcctgc gcggtgaatg gcacttccca gttcacatgc     600
ttctacaact cgcgagccaa catctcctgt gtctggagcc aagatggggc tctgcaggac    660
acttcctgcc aagtccatgc ctggccggac agacggcggt ggaaccaaac ctgtgagctg    720
ctccccgtga gtcaagcatc ctgggcctgc aacctgatcc tcggagcccc agattctcag    780
aaactgacca cagttgacat cgtcaccctg agggtgctgt gtcgtgaggg ggtgcgatgg    840
agggtgatgg ccatccagga cttcaagccc tttgagaacc ttcgcctgat ggccccccatc   900
tccctccaag ttgtccacgt ggagacccac agatgcaaca taagctggga aatctcccaa    960
gcctcccact actttgaaag acacctggag ttcgaggccc ggacgctgtc ccaggccac   1020
acctgggagg aggcccccct gctgactctc aagcagaagc aggaatggat ctgcctggag   1080
acgctcaccc cagacaccca gtatgagttt caggtgcggg tcaagcctct gcaaggcgag   1140
ttcacgacct ggagcccctg gagccagccc ctggccttca ggacaaagcc tgcagccctt   1200
ggaaggaca ccattccgtg gctcggccac ctcctcgtgg gtctcagcgg ggcttttggc    1260
ttcatcatct tagtgtactt gctgatcaac tgcaggaaca ccgggccatg gctgaagaag   1320
gtcctgaagt gtaacacccc agaccctcg aagttctttt cccagctgag ctcagagcat    1380
ggaggagacg tccagaagtg gctctcttcg cccttcccct catcgtcctt cagccctggc   1440
ggcctggcac ctgagatctc gccactagaa gtgctggaga gggacaaggt gacgcagctg   1500
ctcctgcagc aggacaaggt gcctgagccc gcatccttaa gcagcaacca ctcgctgacc   1560
agctgcttca ccaaccaggg ttacttcttc ttccacctcc cggatgcctt ggagatagag   1620
gcctgccagg tgtactttac ttacgacccc tactcagagg aagaccctga tgagggtgtg   1680
gccggggcac ccacagggtc tttcccccaa cccctgcagc ctctgtcagg gaggacgac    1740
gcctactgca ccttccctc cagggatgac ctgctgctct tctcccccag tctcctcggt    1800
ggccccagcc ccccaagcac tgcccctggg ggcagtgggg ccggtgaaga gaggatgccc   1860
ccttctttgc aagaaagagt cccccagaga ctgggaccccc agccctggg gcctcccacc   1920
ccaggagtcc cagacctggt ggattttcag ccaccccctg agctggtgct gcgagaggct   1980
ggggaggagg tccctgacgc tggccccagg gagggagtca gtttcccctg gtccaggcct   2040
cctgggcagg gggagttcag ggcccttaat gctcgcctgc ccctgaacac tgatgcctac   2100
ttgtccctcc aagaactcca gggtcaggac ccaactcact ggtgtga              2148
```

<210> SEQ ID NO 31
<211> LENGTH: 715
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

```
Gln Leu Glu His Leu Leu Asp Leu Gln Met Ile Leu Asn Gly Ile
         35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Glu Gln Lys Leu Ile Ser Glu
145                 150                 155                 160

Glu Asp Leu Glu Met Glu Thr Ser Gln Phe Pro Gly Glu Glu Lys Pro
                165                 170                 175

Gln Ala Ser Pro Glu Gly Arg Pro Glu Ser Glu Thr Ser Cys Ala Val
        180                 185                 190

Asn Gly Thr Ser Gln Phe Thr Cys Phe Tyr Asn Ser Arg Ala Asn Ile
                195                 200                 205

Ser Cys Val Trp Ser Gln Asp Gly Ala Leu Gln Asp Thr Ser Cys Gln
        210                 215                 220

Val His Ala Trp Pro Asp Arg Arg Arg Trp Asn Gln Thr Cys Glu Leu
225                 230                 235                 240

Leu Pro Val Ser Gln Ala Ser Trp Ala Cys Asn Leu Ile Leu Gly Ala
                245                 250                 255

Pro Asp Ser Gln Lys Leu Thr Thr Val Asp Ile Val Thr Leu Arg Val
        260                 265                 270

Leu Cys Arg Glu Gly Val Arg Trp Arg Val Met Ala Ile Gln Asp Phe
        275                 280                 285

Lys Pro Phe Glu Asn Leu Arg Leu Met Ala Pro Ile Ser Leu Gln Val
290                 295                 300

Val His Val Glu Thr His Arg Cys Asn Ile Ser Trp Glu Ile Ser Gln
305                 310                 315                 320

Ala Ser His Tyr Phe Glu Arg His Leu Glu Phe Glu Ala Arg Thr Leu
                325                 330                 335

Ser Pro Gly His Thr Trp Glu Glu Ala Pro Leu Leu Thr Leu Lys Gln
        340                 345                 350

Lys Gln Glu Trp Ile Cys Leu Glu Thr Leu Thr Pro Asp Thr Gln Tyr
        355                 360                 365

Glu Phe Gln Val Arg Val Lys Pro Leu Gln Gly Glu Phe Thr Thr Trp
370                 375                 380

Ser Pro Trp Ser Gln Pro Leu Ala Phe Arg Thr Lys Pro Ala Ala Leu
385                 390                 395                 400

Gly Lys Asp Thr Ile Pro Trp Leu Gly His Leu Leu Val Gly Leu Ser
                405                 410                 415

Gly Ala Phe Gly Phe Ile Ile Leu Val Tyr Leu Leu Ile Asn Cys Arg
        420                 425                 430

Asn Thr Gly Pro Trp Leu Lys Lys Val Leu Lys Cys Asn Thr Pro Asp
        435                 440                 445
```

```
Pro Ser Lys Phe Phe Ser Gln Leu Ser Ser Glu His Gly Gly Asp Val
    450                 455                 460
Gln Lys Trp Leu Ser Ser Pro Phe Pro Ser Ser Phe Ser Pro Gly
465                 470                 475                 480
Gly Leu Ala Pro Glu Ile Ser Pro Leu Glu Val Leu Glu Arg Asp Lys
                485                 490                 495
Val Thr Gln Leu Leu Gln Gln Asp Lys Val Pro Glu Pro Ala Ser
            500                 505                 510
Leu Ser Ser Asn His Ser Leu Thr Ser Cys Phe Thr Asn Gln Gly Tyr
            515                 520                 525
Phe Phe Phe His Leu Pro Asp Ala Leu Glu Ile Glu Ala Cys Gln Val
530                 535                 540
Tyr Phe Thr Tyr Asp Pro Tyr Ser Glu Glu Asp Pro Asp Glu Gly Val
545                 550                 555                 560
Ala Gly Ala Pro Thr Gly Ser Ser Pro Gln Pro Leu Gln Pro Leu Ser
                565                 570                 575
Gly Glu Asp Asp Ala Tyr Cys Thr Phe Pro Ser Arg Asp Asp Leu Leu
            580                 585                 590
Leu Phe Ser Pro Ser Leu Leu Gly Gly Pro Ser Pro Pro Ser Thr Ala
        595                 600                 605
Pro Gly Gly Ser Gly Ala Gly Glu Glu Arg Met Pro Pro Ser Leu Gln
    610                 615                 620
Glu Arg Val Pro Arg Asp Trp Asp Pro Gln Pro Leu Gly Pro Pro Thr
625                 630                 635                 640
Pro Gly Val Pro Asp Leu Val Asp Phe Gln Pro Pro Pro Glu Leu Val
                645                 650                 655
Leu Arg Glu Ala Gly Glu Glu Val Pro Asp Ala Gly Pro Arg Glu Gly
            660                 665                 670
Val Ser Phe Pro Trp Ser Arg Pro Pro Gly Gln Gly Glu Phe Arg Ala
        675                 680                 685
Leu Asn Ala Arg Leu Pro Leu Asn Thr Asp Ala Tyr Leu Ser Leu Gln
    690                 695                 700
Glu Leu Gln Gly Gln Asp Pro Thr His Leu Val
705                 710                 715

<210> SEQ ID NO 32
<211> LENGTH: 3003
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgtacagga tgcaactcct gtcttgcatt gcactaagtc ttgcacttgt cacaaacagt        60
gcacctactt caagttctac aaagaaaaca cagctacaac tggagcattt actgctggat       120
ttacagatga ttttgaatgg aattaataat tacaagaatc ccaaactcac caggatgctc       180
acatttaagt tttacatgcc aagaaggcc acagaactga acatcttca gtgcctagaa         240 gaagaactca aacctctgga ggaagtgcta aatttagctc aaagcaaaaa ctttcactta       300
agacccaggg acttaatcag caatatcaac gtaatagttc tggaactaaa gggatctgaa       360
acaacattca tgtgtgaata tgctgatgag acagcaacca ttgtagaatt tctgaacaga       420
tggattacct tttgtcaaag catcatctca cactgactg agcagaagct catttcggaa        480
gaagaccttg aaatggagac cagtcagttt ccaggtgaag agaagcctca ggcaagcccc       540
```

```
gaaggccgtc ctgagagtga gacttcctgc gcggtgaatg gcacttccca gttcacatgc      600
ttctacaact cgcgagccaa catctcctgt gtctggagcc aagatggggc tctgcaggac      660
acttcctgcc aagtccatgc ctggccggac agacggcggt ggaaccaaac ctgtgagctg      720
ctccccgtga gtcaagcatc ctgggcctgc aacctgatcc tcggagcccc agattctcag      780
aaactgacca cagttgacat cgtcaccctg agggtgctgt gtcgtgaggg ggtgcgatgg      840
agggtgatgg ccatccagga cttcaagccc tttgagaacc ttcgcctgat ggcccccatc      900
tccctccaag ttgtccacgt ggagaccac agatgcaaca taagctggga aatctcccaa       960
gcctcccact actttgaaag acacctggag ttcgaggccc ggacgctgtc cccaggccac     1020
acctgggagg aggccccct gctgactctc aagcagaagc aggaatggat ctgcctggag      1080
acgctcaccc cagacaccca gtatgagttt caggtgcggg tcaagcctct gcaaggcgag     1140
ttcacgacct ggagcccctg agccagccc ctggccttca ggacaaagcc tgcagcccctt     1200
gggaaggaca ccattccgtg gctcggccac ctcctcgtgg gtctcagcgg ggcttttggc     1260
ttcatcatct tagtgtactt gctgatcaac tgcaggaaca ccgggccatg gctgaagaag     1320
gtcctgaagt gtaacacccc agaccctcg aagttcttt cccagctgag ctcagagcat      1380
ggaggagacg tccagaagtg gctctcttcg cccttcccct catcgtcctt cagccctggc     1440
ggcctggcac ctgagatctc gccactagaa gtgctggaga gggacaaggt gacgcagctg     1500
ctcctgcagc aggacaaggt gcctgagccc gcatccttaa gcagcaacca ctcgctgacc     1560
agctgcttca ccaaccaggg ttacttcttc ttccacctcc cggatgcctt ggagatagag     1620
gcctgccagg tgtactttac ttacgacccc tactcagagg aagaccctga tgagggtgtg     1680
gccggggcac ccacagggtc ttcccccaa cccctgcagc ctctgtcagg ggaggacgac      1740
gcctactgca ccttcccctc cagggatgac ctgctgctct ctccccccag tctcctcggt     1800
ggccccagcc cccaagcac tgcccctggg ggcagtgggg ccggtgaaga gaggatgccc      1860
ccttctttgc aagaaagagt ccccagagac tgggaccccc agccctggg gcctcccacc      1920
ccaggagtcc cagacctggt ggattttcag ccacccctg agctggtgct gcgagaggct     1980
ggggaggagg tccctgacgc tggccccagg gagggagtca gtttccctg gtccaggcct     2040
cctgggcagg gggagttcag ggcccttaat gctcgcctgc ccctgaacac tgatgcctac     2100
ttgtccctcc aagaactcca gggtcaggac ccaactcact tggtgagcct gaagacccat     2160
ccattgtgga ggctatggaa gaagatatgg gccgtcccca gccctgagcg gttcttcatg     2220
cccctgtaca agggctgcag cggagacttc aagaaatggg tgggtgcacc cttcactggc     2280
tccagcctgg agctgggacc ctggagccca gaggtgccct ccaccctgga ggtgtacagc     2340
tgccacccac cacggagccc ggccaagagg ctgcagctca cggagctaca agaaccagca     2400
gagctggtgg agtctgacgg tgtgcccaag cccagcttct ggccgacagc ccagaactcg     2460
gggggctcag cttacagtga ggagagggat cggccatacg gctgtgtc cattgacaca       2520
gtgactgtgc tagatgcaga ggggccatgc acctggccct gcagctgtga ggatgacggc     2580
tacccagccc tggacctgga tgctggcctg gagcccagcc caggcctaga ggacccactc     2640
ttggatgcag gaccacagt cctgtcctgt ggctgtgtct cagctggcag ccctgggcta     2700
ggagggcccc tgggaagcct cctggacaga ctaaagccac cccttgcaga tggggaggac     2760
tgggctgggg gactgccctg gggtggccgg tcacctggag gggtctcaga gagtgaggcg     2820
ggctcacccc tggccggcct ggatatggac acgtttgaca gtggctttgt gggctctgac     2880
```

```
tgcagcagcc ctgtggagtg tgacttcacc agccccgggg acgaaggacc ccccggagc    2940 tacctccgcc agtgggtggt cattcctccg ccactttcga gccctggacc ccaggccagc    3000
taa                                                                   3003
```

<210> SEQ ID NO 33
<211> LENGTH: 1000
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Glu Gln Lys Leu Ile Ser Glu
145                 150                 155                 160

Glu Asp Leu Glu Met Glu Thr Ser Gln Phe Pro Gly Glu Glu Lys Pro
                165                 170                 175

Gln Ala Ser Pro Glu Gly Arg Pro Glu Ser Glu Thr Ser Cys Ala Val
            180                 185                 190

Asn Gly Thr Ser Gln Phe Thr Cys Phe Tyr Asn Ser Arg Ala Asn Ile
        195                 200                 205

Ser Cys Val Trp Ser Gln Asp Gly Ala Leu Gln Asp Thr Ser Cys Gln
    210                 215                 220

Val His Ala Trp Pro Asp Arg Arg Trp Asn Gln Thr Cys Glu Leu
225                 230                 235                 240

Leu Pro Val Ser Gln Ala Ser Trp Ala Cys Asn Leu Ile Leu Gly Ala
                245                 250                 255

Pro Asp Ser Gln Lys Leu Thr Thr Val Asp Ile Val Thr Leu Arg Val
            260                 265                 270

Leu Cys Arg Glu Gly Val Arg Trp Arg Val Met Ala Ile Gln Asp Phe
        275                 280                 285

Lys Pro Phe Glu Asn Leu Arg Leu Met Ala Pro Ile Ser Leu Gln Val
    290                 295                 300

Val His Val Glu Thr His Arg Cys Asn Ile Ser Trp Glu Ile Ser Gln
305                 310                 315                 320

Ala Ser His Tyr Phe Glu Arg His Leu Glu Phe Glu Ala Arg Thr Leu
                325                 330                 335
```

```
Ser Pro Gly His Thr Trp Glu Glu Ala Pro Leu Leu Thr Leu Lys Gln
            340                 345                 350

Lys Gln Glu Trp Ile Cys Leu Glu Thr Leu Thr Pro Asp Thr Gln Tyr
        355                 360                 365

Glu Phe Gln Val Arg Val Lys Pro Leu Gln Gly Glu Phe Thr Thr Trp
    370                 375                 380

Ser Pro Trp Ser Gln Pro Leu Ala Phe Arg Thr Lys Pro Ala Ala Leu
385                 390                 395                 400

Gly Lys Asp Thr Ile Pro Trp Leu Gly His Leu Leu Val Gly Leu Ser
                405                 410                 415

Gly Ala Phe Gly Phe Ile Ile Leu Val Tyr Leu Leu Ile Asn Cys Arg
            420                 425                 430

Asn Thr Gly Pro Trp Leu Lys Lys Val Leu Lys Cys Asn Thr Pro Asp
        435                 440                 445

Pro Ser Lys Phe Phe Ser Gln Leu Ser Ser Glu His Gly Gly Asp Val
    450                 455                 460

Gln Lys Trp Leu Ser Ser Pro Phe Pro Ser Ser Ser Phe Ser Pro Gly
465                 470                 475                 480

Gly Leu Ala Pro Glu Ile Ser Pro Leu Glu Val Leu Glu Arg Asp Lys
                485                 490                 495

Val Thr Gln Leu Leu Leu Gln Gln Asp Lys Val Pro Glu Pro Ala Ser
            500                 505                 510

Leu Ser Ser Asn His Ser Leu Thr Ser Cys Phe Thr Asn Gln Gly Tyr
        515                 520                 525

Phe Phe Phe His Leu Pro Asp Ala Leu Glu Ile Glu Ala Cys Gln Val
    530                 535                 540

Tyr Phe Thr Tyr Asp Pro Tyr Ser Glu Glu Asp Pro Asp Glu Gly Val
545                 550                 555                 560

Ala Gly Ala Pro Thr Gly Ser Ser Pro Gln Pro Leu Gln Pro Leu Ser
                565                 570                 575

Gly Glu Asp Asp Ala Tyr Cys Thr Phe Pro Ser Arg Asp Asp Leu Leu
            580                 585                 590

Leu Phe Ser Pro Ser Leu Leu Gly Gly Pro Ser Pro Ser Thr Ala
        595                 600                 605

Pro Gly Gly Ser Gly Ala Gly Glu Glu Arg Met Pro Pro Ser Leu Gln
    610                 615                 620

Glu Arg Val Pro Arg Asp Trp Asp Pro Gln Pro Leu Gly Pro Pro Thr
625                 630                 635                 640

Pro Gly Val Pro Asp Leu Val Asp Phe Gln Pro Pro Pro Glu Leu Val
                645                 650                 655

Leu Arg Glu Ala Gly Glu Glu Val Pro Asp Ala Gly Pro Arg Glu Gly
            660                 665                 670

Val Ser Phe Pro Trp Ser Arg Pro Pro Gly Gln Gly Glu Phe Arg Ala
        675                 680                 685

Leu Asn Ala Arg Leu Pro Leu Asn Thr Asp Ala Tyr Leu Ser Leu Gln
    690                 695                 700

Glu Leu Gln Gly Gln Asp Pro Thr His Leu Val Ser Leu Lys Thr His
705                 710                 715                 720

Pro Leu Trp Arg Leu Trp Lys Lys Ile Trp Ala Val Pro Ser Pro Glu
                725                 730                 735

Arg Phe Phe Met Pro Leu Tyr Lys Gly Cys Ser Gly Asp Phe Lys Lys
            740                 745                 750
```

```
Trp Val Gly Ala Pro Phe Thr Gly Ser Ser Leu Glu Leu Gly Pro Trp
            755                 760                 765

Ser Pro Glu Val Pro Ser Thr Leu Glu Val Tyr Ser Cys His Pro Pro
770                 775                 780

Arg Ser Pro Ala Lys Arg Leu Gln Leu Thr Glu Leu Gln Glu Pro Ala
785                 790                 795                 800

Glu Leu Val Glu Ser Asp Gly Val Pro Lys Pro Ser Phe Trp Pro Thr
                805                 810                 815

Ala Gln Asn Ser Gly Gly Ser Ala Tyr Ser Glu Glu Arg Asp Arg Pro
            820                 825                 830

Tyr Gly Leu Val Ser Ile Asp Thr Val Thr Val Leu Asp Ala Glu Gly
            835                 840                 845

Pro Cys Thr Trp Pro Cys Ser Cys Glu Asp Asp Gly Tyr Pro Ala Leu
    850                 855                 860

Asp Leu Asp Ala Gly Leu Glu Pro Ser Pro Gly Leu Glu Asp Pro Leu
865                 870                 875                 880

Leu Asp Ala Gly Thr Thr Val Leu Ser Cys Gly Cys Val Ser Ala Gly
                885                 890                 895

Ser Pro Gly Leu Gly Gly Pro Leu Gly Ser Leu Leu Asp Arg Leu Lys
            900                 905                 910

Pro Pro Leu Ala Asp Gly Glu Asp Trp Ala Gly Gly Leu Pro Trp Gly
            915                 920                 925

Gly Arg Ser Pro Gly Gly Val Ser Glu Ser Glu Ala Gly Ser Pro Leu
        930                 935                 940

Ala Gly Leu Asp Met Asp Thr Phe Asp Ser Gly Phe Val Gly Ser Asp
945                 950                 955                 960

Cys Ser Ser Pro Val Glu Cys Asp Phe Thr Ser Pro Gly Asp Glu Gly
                965                 970                 975

Pro Pro Arg Ser Tyr Leu Arg Gln Trp Val Val Ile Pro Pro Pro Leu
            980                 985                 990

Ser Ser Pro Gly Pro Gln Ala Ser
            995                 1000

<210> SEQ ID NO 34
<211> LENGTH: 153
<212> TYPE: PRT
<213> ORGANISM: Homo sapiens

<400> SEQUENCE: 34

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125
```

```
Asp Glu Thr Ala Thr Ile Val Glu Phe Leu Asn Arg Trp Ile Thr Phe
        130                 135                 140

Cys Gln Ser Ile Ile Ser Thr Leu Thr
145                 150
```

<210> SEQ ID NO 35
<211> LENGTH: 551
<212> TYPE: PRT
<213> ORGANISM: Homo sapiens

<400> SEQUENCE: 35

```
Met Ala Ala Pro Ala Leu Ser Trp Arg Leu Pro Leu Leu Ile Leu Leu
1               5                   10                  15

Leu Pro Leu Ala Thr Ser Trp Ala Ser Ala Val Asn Gly Thr Ser
            20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
    290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
```

```
                    340                 345                 350
His Ser Leu Thr Ser Cys Phe Thr Asn Gln Gly Tyr Phe Phe His
            355                 360                 365

Leu Pro Asp Ala Leu Glu Ile Glu Ala Cys Gln Val Tyr Phe Thr Tyr
370                 375                 380

Asp Pro Tyr Ser Glu Glu Asp Pro Asp Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
            435                 440                 445

Gly Ala Gly Glu Glu Arg Met Pro Pro Ser Leu Gln Glu Arg Val Pro
            450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
            515                 520                 525

Leu Pro Leu Asn Thr Asp Ala Tyr Leu Ser Leu Gln Glu Leu Gln Gly
            530                 535                 540

Gln Asp Pro Thr His Leu Val
545                 550

<210> SEQ ID NO 36
<211> LENGTH: 538
<212> TYPE: PRT
<213> ORGANISM: Homo sapiens

<400> SEQUENCE: 36

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
            130                 135                 140

Pro Ala Phe Tyr Met Leu Lys Gly Lys Leu Gln Tyr Glu Leu Gln Tyr
145                 150                 155                 160
```

```
Arg Asn Arg Gly Asp Pro Trp Ala Val Ser Pro Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
            210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
            405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
            450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
            485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
            530                 535
```

<210> SEQ ID NO 37

<400> SEQUENCE: 37

000

```
<210> SEQ ID NO 38
<211> LENGTH: 220
<212> TYPE: PRT
<213> ORGANISM: Homo sapiens

<400> SEQUENCE: 38

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 39
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Gly Gly Gly Ser
1

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Lys Cys Asn Thr Pro Asp Pro Ser
1               5

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Cys Phe Thr Asn Gln Gly Tyr Phe Phe His Leu Pro Asp Ala
1               5                   10                  15

Leu Glu Ile Glu Ala
            20

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ala Tyr Leu Ser Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Ile Trp Ala Val Pro Ser Pro Glu
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Leu Val Glu Ser Asp Gly Val Pro Lys
1               5                   10
```

```
<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Tyr Leu Arg Gln
1               5

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcagcaacca ctcgctgacc gcctgccagg tgtactttac                             40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtaaagtaca cctggcaggc ggtcagcgag tggttgctgc                             40
```